US006977074B2

(12) United States Patent
Kündig et al.

(10) Patent No.: US 6,977,074 B2
(45) Date of Patent: Dec. 20, 2005

(54) METHOD OF INDUCING A CTL RESPONSE

(75) Inventors: Thomas M. Kündig, Zurich (CH); John J. L. Simard, Northridge, CA (US)

(73) Assignee: Mannkind Corporation, Valencia, CA (US)

( * ) Notice: Subject to any disclaimer, the term of this patent is extended or adjusted under 35 U.S.C. 154(b) by 553 days.

(21) Appl. No.: 09/776,232

(22) Filed: Feb. 2, 2001

(65) Prior Publication Data

US 2002/0007173 A1 Jan. 17, 2002

Related U.S. Application Data

(63) Continuation-in-part of application No. 09/380,534, filed as application No. PCT/US98/14289 on Jul. 10, 1998, which is a continuation-in-part of application No. 08/988,320, filed on Dec. 10, 1997, now abandoned.

(30) Foreign Application Priority Data

Jul. 10, 1997 (CA) ............................................. 2209815

(51) Int. Cl.[7] ........................ A61K 39/00; A61K 39/02; A61K 39/12; C12N 7/01; C12N 1/21
(52) U.S. Cl. ................ 424/93.7; 424/184.1; 424/186.1; 424/190.1; 424/199.1; 424/200.1; 424/534; 435/7.23; 435/7.24; 435/7.93; 435/236; 435/252; 435/325; 514/44; 530/300; 530/350; 530/351; 536/23.5
(58) Field of Search ............................. 424/93.7, 184.1, 424/186.1, 190.1, 199.1, 200.1, 534; 435/325, 252, 5, 6, 320; 514/44; 530/300, 350, 351; 536/23.5

(56) References Cited

U.S. PATENT DOCUMENTS

| | | | |
|---|---|---|---|
| 3,604,417 A | 9/1971 | Stolzenberg et al. |
| 3,732,865 A | 5/1973 | Higuchi et al. |
| 3,760,804 A | 9/1973 | Higuchi et al. |
| 3,760,805 A | 9/1973 | Higuchi |
| 3,760,984 A | 9/1973 | Theeuwes |
| 3,929,132 A | 12/1975 | Higuchi |
| 3,987,790 A | 10/1976 | Eckenhoff et al. |
| 3,995,631 A | 12/1976 | Higuchi et al. |
| 3,995,632 A | 12/1976 | Nakano et al. |
| 4,034,756 A | 7/1977 | Higuchi et al. |
| 4,203,440 A | 5/1980 | Theeuwes |
| 4,286,067 A | 8/1981 | Theeuwes |
| 4,300,558 A | 11/1981 | Eckenhoff et al. |
| 4,304,232 A | 12/1981 | Michaels |
| 4,340,048 A | 7/1982 | Eckenhoff |
| 4,340,054 A | 7/1982 | Michaels |
| 4,350,271 A | 9/1982 | Eckenhoff |
| 4,367,741 A | 1/1983 | Michaels |
| 4,435,173 A | 3/1984 | Siposs et al. |
| 4,439,199 A | 3/1984 | Amkraut et al. |
| 4,450,198 A | 5/1984 | Michaels |
| 4,455,145 A | 6/1984 | Theeuwes |
| 4,474,575 A | 10/1984 | Eckenhoff et al. |
| 4,498,843 A | 2/1985 | Schneider et al. |
| 4,526,569 A | 7/1985 | Bernardi |
| 4,552,651 A | 11/1985 | Sandbrook et al. |
| 4,561,856 A | 12/1985 | Cochran |
| 4,619,652 A | 10/1986 | Eckenhoff et al. |
| 4,643,723 A | 2/1987 | Smit |
| 4,753,651 A | 6/1988 | Eckenhoff |
| 4,767,628 A | 8/1988 | Hutchinson |
| 4,838,862 A | 6/1989 | Baker et al. |
| 4,855,141 A | 8/1989 | Eckenhoff et al. |
| 4,865,598 A | 9/1989 | Eckenhoff |
| 4,865,845 A | 9/1989 | Eckenhoff et al. |
| 4,872,873 A | 10/1989 | Zingerman |
| 4,898,582 A | 2/1990 | Faste |
| 4,908,433 A | 3/1990 | Mertelsmann et al. |
| 4,929,233 A | 5/1990 | Roth et al. |
| 4,963,141 A | 10/1990 | Eckenhoff |
| 4,976,966 A | 12/1990 | Theeuwes et al. |
| 5,017,381 A | 5/1991 | Maruyama et al. |
| 5,023,088 A | 6/1991 | Wong et al. |
| 5,030,216 A | 7/1991 | Theeuwes et al. |
| 5,034,229 A | 7/1991 | Magruder et al. |
| 5,037,420 A | 8/1991 | Magruder et al. |
| 5,057,318 A | 10/1991 | Magruder et al. |
| 5,059,423 A | 10/1991 | Magruder et al. |
| 5,110,596 A | 5/1992 | Magruder et al. |
| 5,110,597 A | 5/1992 | Wong et al. |

(Continued)

FOREIGN PATENT DOCUMENTS

| | | |
|---|---|---|
| CA | 2147863 | 5/1994 |
| IE | 74899 | 8/1997 |
| WO | WO 92/21033 | 11/1992 |
| WO | 93/03175 | 4/1995 |
| WO | WO 95/17167 | 6/1995 |
| WO | WO 96/01429 | 1/1996 |
| WO | WO 96/27008 | 9/1996 |
| WO | WO 96/40209 | 12/1996 |

(Continued)

OTHER PUBLICATIONS

Stryer et al, in Biochemistry, Third Edition, W H Freeman Company, New York, pp. 31–33, 1998.*
Ngo et al, 1994, The Protein Folding Problem and Tertiary Structure Prediction, pp. 492–495.*
Attwood et al, The Babel of Bioinformatics, 2000, Science vol. 290 No 5491: 471–473.*

*Primary Examiner*—Christina Chan
*Assistant Examiner*—Phuong Huynh
(74) *Attorney, Agent, or Firm*—Knobbe Martens Olson & Bear LLP

(57) ABSTRACT

Disclosed herein are methods for inducing an immunological CTL response to an antigen by sustained, regular delivery of the antigen to a mammal so that the antigen reaches the lymphatic system. Antigen is delivered at a level sufficient to induce an immunologic CTL response in a mammal and the level of the antigen in the mammal's lymphatic system is maintained over time sufficient to maintain the immunologic CTL response. Also disclosed is an article of manufacture for delivering an antigen that induces a CTL response in an animal.

32 Claims, 12 Drawing Sheets

U.S. PATENT DOCUMENTS

| | | | |
|---|---|---|---|
| 5,135,498 | A | 8/1992 | Kam et al. |
| 5,135,523 | A | 8/1992 | Magruder et al. |
| 5,137,727 | A | 8/1992 | Eckenhoff |
| 5,169,390 | A | 12/1992 | Athayde et al. |
| 5,174,999 | A | 12/1992 | Magruder et al. |
| 5,209,746 | A | 5/1993 | Balaban et al. |
| 5,221,278 | A | 6/1993 | Linkwitz et al. |
| 5,223,265 | A | 6/1993 | Wong |
| 5,257,987 | A | 11/1993 | Athayde et al. |
| 5,286,254 | A | 2/1994 | Shapland et al. |
| 5,304,165 | A | 4/1994 | Haber et al. |
| 5,368,562 | A | 11/1994 | Blomquist et al. |
| 5,478,556 | A | 12/1995 | Elliott et al. |
| 5,496,360 | A | 3/1996 | Hoffmann et al. |
| 5,580,859 | A | 12/1996 | Felgner et al. |
| 5,589,466 | A | 12/1996 | Felgner et al. |
| 5,679,647 | A | 10/1997 | Carson et al. |
| 5,696,079 | A * | 12/1997 | Lane et al. |
| 5,698,396 | A | 12/1997 | Pfreundschuh |
| 5,733,548 | A | 3/1998 | Restifo et al. |
| 5,744,316 | A | 4/1998 | Lethe et al. |
| 5,747,269 | A | 5/1998 | Rammensee et al. |
| 5,766,601 | A * | 6/1998 | Ennis ...................... 424/206.1 |
| 5,830,452 | A * | 11/1998 | Bauer et al. |
| 5,846,540 | A | 12/1998 | Restifo et al. |
| 5,853,719 | A * | 12/1998 | Nair et al. ................ 424/93.21 |
| 5,856,187 | A | 1/1999 | Restifo et al. |
| 5,962,428 | A | 10/1999 | Carrano et al. |
| 6,037,135 | A | 3/2000 | Kubo et al. |
| 6,204,250 | B1 * | 3/2001 | Bot et al. |
| 6,214,804 | B1 | 4/2001 | Felgner et al. |
| 6,419,931 | B1 * | 7/2002 | Vitiello et al. ............ 424/201.1 |

FOREIGN PATENT DOCUMENTS

| | | |
|---|---|---|
| WO | WO 98/13489 | 4/1998 |
| WO | WO 98/14464 | 4/1998 |
| WO | WO 98/27963 | 7/1998 |
| WO | WO 98/43611 | 10/1998 |
| WO | WO 99/02183 A | 1/1999 |

OTHER PUBLICATIONS

Skolnick et al, From genes to protein structure and function: novel applications of computational approaches in the genomic er Jan., 2000, TIBTECH 18:34–39.*

Koga et al, International Archives of Allergy and Applied Immunology 51(3): 359–67, 1976, Abstract.*

Klavinskis et al, J Immunol 157(6): 2521–7, Sep. 1996.*

Coupey et al, Cytokine 5(6): 564–9, Nov 1993.*

Zinkernagel et al, Immunol Rev 156: 199–209, Apr. 1997.*

Grohmann et al, J Immunol Methods 137(1): 9–15, Mar. 1991.*

Issekutz et al, Clin Exp Immunol 56(3): 515–23, Jun. 1984.*

Sadao et al, Biotherapy 9(7): 845–851, 1995; in Japanese with English Translation.*

Kundig, T.M., "A Method to increase the Immunogenicity of vaccines," *Schweiz. Rundsch. Med. Prax.*, 89(37):1477–1484 (Sep. 2000) (German with English Summary).

Schott, M. et al., "Induction of cellular immunity in a parathyroid carcinoma treated with tumor lysate-pulsed dendritic cells," *Eur. J. Endocrinology*, 142(3):300–306 (Mar. 2000).

Sedlik, C., et al., "Recombinant parvovirus-like particles as an antigen carrier: A novel nonreplicative exogenous antigen to elicit protective antiviral cytotoxic T cells," *Proc. Natl. Acad. Sci. USA*, vol. 94, pp. 7503–7508, (1997).

Bachmann, M.F., et al. (1994) In vitro vs. in vivo assays for the assessment of T–and B cell function. Curr. Opin. Immunol. 6:320–326.

Cleland, J.L., et al. (1994) Formulation and delivery of proteins and peptides. American Chemical Society, ACS Symposium Series No. 567.

Courvalian, P. et al. (1995) Life Sci. 316:1207–1212.

Dietrich, G. et al. (1998) Biotechnology 16:181–185.

Durrant LG (1997) Cancer vaccines. Anti-cancer drugs, 8:727–733.

Grohmann, U. et al. (1991) Intrasplenic immunization for the induction of humoral and cell–mediated immunity to nitrocellulose–bound antigen. Journal of Immunological Methods, 137:9–15.

Haynes, B. F. et al. (1996) Toward and understanding of the correlates of protective immunity to HIV infection. Science, 271:324–327.

Inaba, K., et al. (1992) Identification of proliferating dendritic cell precursors in mouse blood. Journal of Experimental Medicine. 175:1157–1167.

Jager, E., et al. (1996) Granulocyte–macrophage–colony–stimulating factor enhances Immune responses to melanoma–associated peptides In vivo. Int. J. Cancer, 67:54–62.

Jager, E. et al. (1996) Simultaneous humoral and cellular immune response against cancer–testis antigen NY–ESO–1: definition of human histocompatibility leukocyte antigen (HLA)–A2–binding Peptide Epitopes. J.Exp.Med. 187:265–270.

Kundig, T.M. et al, (1992) Skin test to assess virus–specific cytotoxic T–cell activity. Proc. Natl. Acad. Sci. 89:7757–7761.

Kundig, T.M. et al. (1995) Fibroblasts as efficient antigen–presenting cells in lymphoid organs. Science. 266:1343–1347.

Kundig, T.M. et al. (1996) On the role of antigen in maintaining cytotoxid T cell memory. Proc. Natl. Acad. Sci. 93:9716–9723.

Moskophidis D. et al. (1995) Immunobiology of Cytotoxic T–cell escape mutants of lymphocytic choriomeningitis virus. Journal of Virology, 69:4:2187–2193.

Oehen S. et al. (1992) Antivirally protective cytotoxic T cell memory to lymphocytic choriomeningitis virus is governed by persisting antigen. J.Exp.Med. 176:1273–1281.

Oldstone, M. et al. (1995) Discriminated selection among viral peptides with the appropriate anchor residues: Implications for the size of the cytotoxic T–lymphocyte repertoire and control of viral infection. Journal of Virology, 69:12:7423–7429.

Pantaleo G. et al. (1997) Evidence for rapid disappearance of initially expanded HIV–specific CD8+ T cell clones during primary HIV infection. Proc. Natl. Acad. Sci. 94:9848–9853.

Peters, R.I. et al. (1984) Tryptohan and serotonin metabolism after sustained tryptophan infusion. Neurochem. Int. 6:6:685–691.

Pfeiffer, et al. "Insulin Pump Therapy" 3.1 to 3.2.4 p. 14–33.

Puccetti P. et al. (1994) Use of skin test assay to determine tumor–specific CD8+ T cell reactivity. Eur. J. Immunol. 24:1446–1452.

Rammensee, H.G. et al. (1995) MHC ligands and peptide motifs: first listing. Immunogenetics,41:176–228.

Rammensee, H.G. et al. (1997) MHC ligands and peptide motifs. Landes Bioscience Austin Texas. Chapter 4:217–369.

Remington (1985) The science and practice of pharmacy, Nineteenth Edition: Chapters 86–88.

Santus G. et al. (1995) Osmotic drug deliver: a review of patent literature. Journal of Controlled Release. 35:1–21.

Simard, John J.L. et al.; 09/560,465; Apr. 28, 2000; Epitope Synchronization in Antigen Presenting Cells.

Simard, John J.L., et al.; 09/561,074; Apr. 26, 2000; Method of Epitope Discovery.

Simard, John J.L., et al.; 09/581,571; Apr. 28, 2000; Epitope Clusters.

Simard, John J.L., et al.; 09/581,572; Apr. 28, 2000; Expression Vectors Encoding Epitopes of Target–Associated Antigens.

Sizemore, D.R. et al. (1995) Science 270:299–302.

Speiser, D.E. et al. (1997) Self antigens expressed by solid tumors do not efficiently stimulate naive or activated T cells: implications for immunotherapy. J. Exp. Med. 186:645–653.

Steinman R.M. (1991) The dendritic cell system and its role in immunogenicity. Annu. Rev. Immunol. 9:271–296.

Wiseman C. et al. (193) Clinical responses to intralymphatic whole–cell melanoma vaccine augmented by in vitro incubation with alpha–interferon. Annals of the New York Academy of Sciences. 690:388–391.

Wiseman C.L. et al, (1989) Clinical responses with active specific intralymphatic immunotherapy for cancer—A phase I–II trial. The Western Journal of Medicine. 151:283–288.

Young J. W. et al. (1996) Dendritic cells as adjuvants for class I major histocompatibility complex–restricted antitumor immunity. J.Exp.Med. 183:7–11.

Zipkin I. (1998) Cancer vaccines. BioCentury, 6:A1–A6.

Brown et al., "Adenovirus–Transduced Dendritic Cells Injected into Skin or Lymph Node Prime Potent Simlan Immunodeficiency Virus–Specific T Cell Immunity in Monkeys," *The Journal of Immunology*, 171:6875–6882 (2003).

Fong et al., "Dendritic Cells Injected Via Different Routes Induce Immunity in Cancer Patients," *The Journal of Immunology*, 168: 4254–4259 (2001).

Nestle et al., "Vaccination of melanoma patients with peptide or tumor lysate–pulsed dendritic cells," *Nature Medicine*, 4:328–332 (1998).

Timmerman et al., "Melanoma vaccines: Prim and proper presentation," *Nature Medicine*, 4:269–270 (1998).

* cited by examiner

Graphs show lysis of unpulsed EL4 cells (open circles) and EL4 cells pulsed with gp33 peptide (solid triangles). Symbols represent individual mice.

Graphs show lysis of unpulsed EL4 cells (open circles) and EL4 cells pulsed with gp33 peptide (solid triangles). Symbols represent individual mice.

Figure 8.

Graphs show systemic LCMV titers (A), and vaccinia titers in ovaries (B). Symbols represent individual mice.

Mean tumor volumes ±1SD are shown for mice immunized with pEFGPL33A DNA (solid circles) or control pEGFP-N3 DNA (open triangles). Numbers in brackets indicate number of mice with tumors / total number of mice in group.

Figure 11.

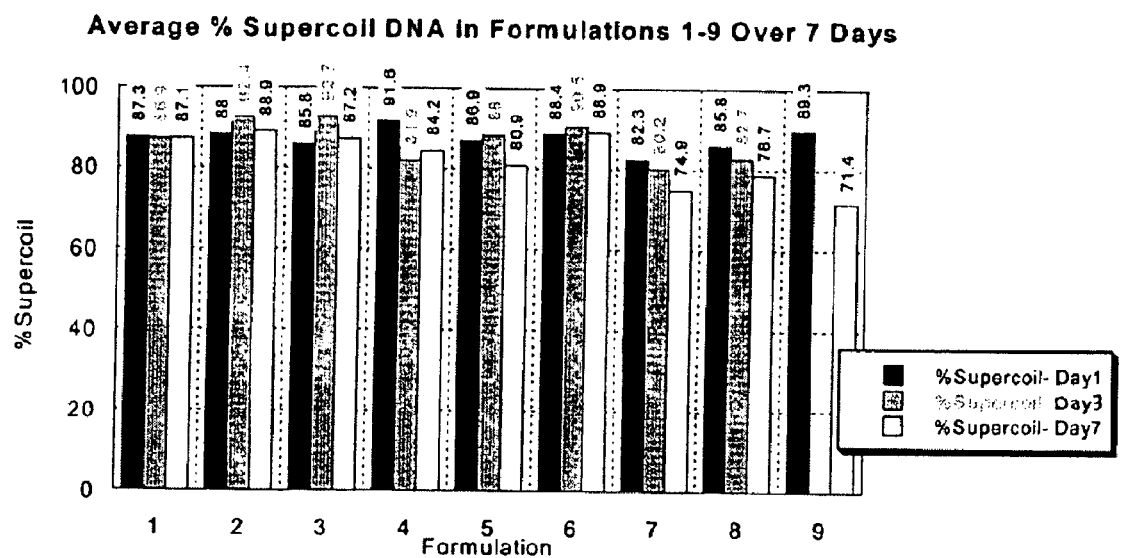

Formulations
1. 10% Ethanol, 0.25mM EDTA, Citrate Phosphate pH 7.6
2. 10% Ethanol, 0.25mM EDTA, Citrate Phosphate pH 7.4
3. 1% Ethanol, 0.5mM EDTA, Citrate Phosphate pH 7.4
4. 1% Ethanol, 0.5mM EDTA, 1X PBS pH 7.4
5. 0.5% Benzyl Alcohol, 0.25mM EDTA, Citrate Phosphate pH 7.6
6. 1% Benzyl Alcohol, 1% Ethanol, 0.5mM EDTA, Citrate Phosphate pH 7.6
7. 1% Benzyl Alcohol, 1% Ethanol, 0.5mM EDTA, 0.1M TRIS pH 7.4
8. 1% Benzyl Alcohol, 1% Ethanol, 0.5mM EDTA, 0.1M TRIS pH 8.2
9. 1% Benzyl Alcohol, 1X PBS pH 8.2

SEQUENCE LISTING

<160> NUMBER OF SEQ ID NOS: 569

<210> SEQ ID NO 1
<211> LENGTH: 9
<212> TYPE: PRT
<213> ORGANISM: Adenovirus 3

<400> SEQUENCE: 1

Leu Ile Val Ile Gly Ile Leu Ile Leu
 1               5

<210> SEQ ID NO 2
<211> LENGTH: 10
<212> TYPE: PRT
<213> ORGANISM: Adenovirus 5

<400> SEQUENCE: 2

Ser Gly Pro Ser Asn Thr Pro Pro Glu Ile
 1               5                  10

<210> SEQ ID NO 3
<211> LENGTH: 9
<212> TYPE: PRT
<213> ORGANISM: Adenovirus 5

<400> SEQUENCE: 3

Val Asn Ile Arg Asn Cys Cys Tyr Ile
 1               5

<210> SEQ ID NO 4
<211> LENGTH: 10
<212> TYPE: PRT
<213> ORGANISM: Adenovirus 5

<400> SEQUENCE: 4

Ser Gly Pro Ser Asn Ile Pro Pro Glu Ile
 1               5                  10

<210> SEQ ID NO 5
<211> LENGTH: 9
<212> TYPE: PRT
<213> ORGANISM: CSFV

<400> SEQUENCE: 5

Glu Asn Ala Leu Leu Val Ala Leu Phe
 1               5

<210> SEQ ID NO 6
<211> LENGTH: 9
<212> TYPE: PRT
<213> ORGANISM: Dengue virus 4

<400> SEQUENCE: 6

Thr Pro Glu Gly Ile Ile Pro Thr Leu
 1               5

<210> SEQ ID NO 7
<211> LENGTH: 9
<212> TYPE: PRT
<213> ORGANISM: EEV

<400> SEQUENCE: 7

Cys Leu Gly Gly Leu Leu Thr Met Val

-continued

```
<210> SEQ ID NO 8
<211> LENGTH: 9
<212> TYPE: PRT
<213> ORGANISM: EBV

<400> SEQUENCE: 8

Asn Ile Ala Glu Gly Leu Arg Ala Leu
 1               5

<210> SEQ ID NO 9
<211> LENGTH: 9
<212> TYPE: PRT
<213> ORGANISM: EBV

<400> SEQUENCE: 9

Asn Leu Arg Arg Gly Thr Ala Leu Ala
 1               5

<210> SEQ ID NO 10
<211> LENGTH: 9
<212> TYPE: PRT
<213> ORGANISM: EBV

<400> SEQUENCE: 10

Ala Leu Ala Ile Pro Gln Cys Arg Leu
 1               5

<210> SEQ ID NO 11
<211> LENGTH: 9
<212> TYPE: PRT
<213> ORGANISM: EBV

<400> SEQUENCE: 11

Val Leu Lys Asp Ala Ile Lys Asp Leu
 1               5

<210> SEQ ID NO 12
<211> LENGTH: 9
<212> TYPE: PRT
<213> ORGANISM: EBV

<400> SEQUENCE: 12

Phe Met Val Phe Leu Gln Thr His Ile
 1               5

<210> SEQ ID NO 13
<211> LENGTH: 9
<212> TYPE: PRT
<213> ORGANISM: EBV

<400> SEQUENCE: 13

His Leu Ile Val Asp Thr Asp Ser Leu
 1               5

<210> SEQ ID NO 14
<211> LENGTH: 9
<212> TYPE: PRT
<213> ORGANISM: EBV

<400> SEQUENCE: 14

Ser Leu Gly Asn Pro Ser Leu Ser Val
 1               5
```

-continued

```
<210> SEQ ID NO 15
<211> LENGTH: 9
<212> TYPE: PRT
<213> ORGANISM: EBV

<400> SEQUENCE: 15

Pro Leu Ala Ser Ala Met Arg Met Leu
1               5

<210> SEQ ID NO 16
<211> LENGTH: 9
<212> TYPE: PRT
<213> ORGANISM: EBV

<400> SEQUENCE: 16

Arg Met Leu Trp Met Ala Asn Tyr Ile
1               5

<210> SEQ ID NO 17
<211> LENGTH: 9
<212> TYPE: PRT
<213> ORGANISM: EBV

<400> SEQUENCE: 17

Met Leu Trp Met Ala Asn Tyr Ile Val
1               5

<210> SEQ ID NO 18
<211> LENGTH: 9
<212> TYPE: PRT
<213> ORGANISM: EBV

<400> SEQUENCE: 18

Ile Leu Pro Gln Gly Pro Gln Thr Ala
1               5

<210> SEQ ID NO 19
<211> LENGTH: 9
<212> TYPE: PRT
<213> ORGANISM: EBV

<400> SEQUENCE: 19

Pro Leu Arg Pro Thr Ala Pro Thr Ile
1               5

<210> SEQ ID NO 20
<211> LENGTH: 9
<212> TYPE: PRT
<213> ORGANISM: EBV

<400> SEQUENCE: 20

Pro Leu Pro Pro Ala Thr Leu Thr Val
1               5

<210> SEQ ID NO 21
<211> LENGTH: 9
<212> TYPE: PRT
<213> ORGANISM: EBV

<400> SEQUENCE: 21

Arg Met His Leu Pro Val Leu His Val
1               5

<210> SEQ ID NO 22
```

-continued

```
<211> LENGTH: 9
<212> TYPE: PRT
<213> ORGANISM: EBV

<400> SEQUENCE: 22

Pro Met Pro Leu Pro Pro Ser Gln Leu
1               5

<210> SEQ ID NO 23
<211> LENGTH: 9
<212> TYPE: PRT
<213> ORGANISM: EBV

<400> SEQUENCE: 23

Gln Leu Pro Pro Pro Ala Ala Pro Ala
1               5

<210> SEQ ID NO 24
<211> LENGTH: 9
<212> TYPE: PRT
<213> ORGANISM: EBV

<400> SEQUENCE: 24

Ser Met Pro Glu Leu Ser Pro Val Leu
1               5

<210> SEQ ID NO 25
<211> LENGTH: 9
<212> TYPE: PRT
<213> ORGANISM: EBV

<400> SEQUENCE: 25

Asp Leu Asp Glu Ser Trp Asp Tyr Ile
1               5

<210> SEQ ID NO 26
<211> LENGTH: 9
<212> TYPE: PRT
<213> ORGANISM: EBV

<400> SEQUENCE: 26

Pro Leu Pro Cys Val Leu Trp Pro Val
1               5

<210> SEQ ID NO 27
<211> LENGTH: 9
<212> TYPE: PRT
<213> ORGANISM: EBV

<400> SEQUENCE: 27

Ser Leu Glu Glu Cys Asp Ser Glu Leu
1               5

<210> SEQ ID NO 28
<211> LENGTH: 9
<212> TYPE: PRT
<213> ORGANISM: EBV

<400> SEQUENCE: 28

Glu Ile Lys Arg Tyr Lys Asn Arg Val
1               5

<210> SEQ ID NO 29
<211> LENGTH: 9
<212> TYPE: PRT
```

<213> ORGANISM: EBV

<400> SEQUENCE: 29

Gln Leu Leu Gln His Tyr Arg Glu Val
1               5

<210> SEQ ID NO 30
<211> LENGTH: 9
<212> TYPE: PRT
<213> ORGANISM: HCV-1

<400> SEQUENCE: 30

Leu Leu Gln His Tyr Arg Glu Val Ala
1               5

<210> SEQ ID NO 31
<211> LENGTH: 9
<212> TYPE: PRT
<213> ORGANISM: EBV

<400> SEQUENCE: 31

Leu Leu Lys Gln Met Cys Pro Ser Leu
1               5

<210> SEQ ID NO 32
<211> LENGTH: 9
<212> TYPE: PRT
<213> ORGANISM: EBV

<400> SEQUENCE: 32

Ser Ile Ile Pro Arg Thr Pro Asp Val
1               5

<210> SEQ ID NO 33
<211> LENGTH: 10
<212> TYPE: PRT
<213> ORGANISM: EBV

<400> SEQUENCE: 33

Leu Leu Asp Phe Val Arg Phe Met Gly Val
1               5                   10

<210> SEQ ID NO 34
<211> LENGTH: 9
<212> TYPE: PRT
<213> ORGANISM: EBV

<400> SEQUENCE: 34

Ser Val Arg Asp Arg Leu Ala Arg Leu
1               5

<210> SEQ ID NO 35
<211> LENGTH: 9
<212> TYPE: PRT
<213> ORGANISM: EBV

<400> SEQUENCE: 35

Ile Val Thr Asp Phe Ser Val Ile Lys
1               5

<210> SEQ ID NO 36
<211> LENGTH: 10
<212> TYPE: PRT
<213> ORGANISM: EBV

-continued

<400> SEQUENCE: 36

Ala Val Phe Asp Arg Lys Ser Asp Ala Lys
1               5                   10

<210> SEQ ID NO 37
<211> LENGTH: 8
<212> TYPE: PRT
<213> ORGANISM: EBV

<400> SEQUENCE: 37

Arg Tyr Ser Ile Phe Phe Asp Tyr
1               5

<210> SEQ ID NO 38
<211> LENGTH: 9
<212> TYPE: PRT
<213> ORGANISM: EBV

<400> SEQUENCE: 38

Gln Pro Arg Ala Pro Ile Arg Pro Ile
1               5

<210> SEQ ID NO 39
<211> LENGTH: 9
<212> TYPE: PRT
<213> ORGANISM: EBV

<400> SEQUENCE: 39

Arg Pro Pro Ile Phe Ile Arg Arg Leu
1               5

<210> SEQ ID NO 40
<211> LENGTH: 9
<212> TYPE: PRT
<213> ORGANISM: EBV

<400> SEQUENCE: 40

Glu Pro Asp Val Pro Pro Gly Ala Ile
1               5

<210> SEQ ID NO 41
<211> LENGTH: 9
<212> TYPE: PRT
<213> ORGANISM: EBV

<400> SEQUENCE: 41

Ile Pro Gln Cys Arg Leu Thr Pro Leu
1               5

<210> SEQ ID NO 42
<211> LENGTH: 9
<212> TYPE: PRT
<213> ORGANISM: EBV

<400> SEQUENCE: 42

Gly Pro Gly Pro Gln Pro Gly Pro Leu
1               5

<210> SEQ ID NO 43
<211> LENGTH: 9
<212> TYPE: PRT
<213> ORGANISM: EBV

<400> SEQUENCE: 43

```
Gln Pro Gly Pro Leu Glu Arg Ser Ile
 1               5

<210> SEQ ID NO 44
<211> LENGTH: 9
<212> TYPE: PRT
<213> ORGANISM: EBV

<400> SEQUENCE: 44

Arg Pro Gln Lys Arg Pro Ser Cys Ile
 1               5

<210> SEQ ID NO 45
<211> LENGTH: 9
<212> TYPE: PRT
<213> ORGANISM: EBV

<400> SEQUENCE: 45

Pro Pro Thr Pro Leu Leu Thr Val Leu
 1               5

<210> SEQ ID NO 46
<211> LENGTH: 9
<212> TYPE: PRT
<213> ORGANISM: EBV

<400> SEQUENCE: 46

Thr Pro Ser Pro Pro Arg Met His Leu
 1               5

<210> SEQ ID NO 47
<211> LENGTH: 9
<212> TYPE: PRT
<213> ORGANISM: EBV

<400> SEQUENCE: 47

Pro Pro Arg Met His Leu Pro Val Leu
 1               5

<210> SEQ ID NO 48
<211> LENGTH: 9
<212> TYPE: PRT
<213> ORGANISM: EBV

<400> SEQUENCE: 48

Val Pro Asp Gln Ser Met His Pro Leu
 1               5

<210> SEQ ID NO 49
<211> LENGTH: 9
<212> TYPE: PRT
<213> ORGANISM: EBV

<400> SEQUENCE: 49

Pro Pro Ser Ile Asp Pro Ala Asp Leu
 1               5

<210> SEQ ID NO 50
<211> LENGTH: 9
<212> TYPE: PRT
<213> ORGANISM: EEV

<400> SEQUENCE: 50

Leu Pro Cys Val Leu Trp Pro Val Leu
 1               5
```

```
<210> SEQ ID NO 51
<211> LENGTH: 10
<212> TYPE: PRT
<213> ORGANISM: EBV

<400> SEQUENCE: 51

Cys Pro Ser Leu Asp Val Asp Ser Ile Ile
 1               5                  10

<210> SEQ ID NO 52
<211> LENGTH: 9
<212> TYPE: PRT
<213> ORGANISM: EBV

<400> SEQUENCE: 52

Thr Pro Asp Val Leu His Glu Asp Leu
 1               5

<210> SEQ ID NO 53
<211> LENGTH: 9
<212> TYPE: PRT
<213> ORGANISM: EBV

<400> SEQUENCE: 53

Phe Leu Arg Gly Arg Ala Tyr Gly Leu
 1               5

<210> SEQ ID NO 54
<211> LENGTH: 9
<212> TYPE: PRT
<213> ORGANISM: EBV

<400> SEQUENCE: 54

Gln Ala Lys Trp Arg Leu Gln Thr Leu
 1               5

<210> SEQ ID NO 55
<211> LENGTH: 9
<212> TYPE: PRT
<213> ORGANISM: EBV

<400> SEQUENCE: 55

Ala Tyr Pro Leu His Glu Gln His Gly
 1               5

<210> SEQ ID NO 56
<211> LENGTH: 9
<212> TYPE: PRT
<213> ORGANISM: EBV

<400> SEQUENCE: 56

Tyr Ile Lys Ser Phe Val Ser Asp Ala
 1               5

<210> SEQ ID NO 57
<211> LENGTH: 9
<212> TYPE: PRT
<213> ORGANISM: EBV

<400> SEQUENCE: 57

Arg Arg Arg Trp Arg Arg Leu Thr Val
 1               5
```

```
<210> SEQ ID NO 58
<211> LENGTH: 9
<212> TYPE: PRT
<213> ORGANISM: Hepatitus C virus

<400> SEQUENCE: 58

Arg Arg Ile Tyr Asp Leu Ile Glu Leu
1               5

<210> SEQ ID NO 59
<211> LENGTH: 9
<212> TYPE: PRT
<213> ORGANISM: EBV

<400> SEQUENCE: 59

Tyr Pro Leu His Glu Gln His Gly Met
1               5

<210> SEQ ID NO 60
<211> LENGTH: 9
<212> TYPE: PRT
<213> ORGANISM: Hepatits C virus

<400> SEQUENCE: 60

His Ser Lys Lys Lys Cys Asp Glu Leu
1               5

<210> SEQ ID NO 61
<211> LENGTH: 8
<212> TYPE: PRT
<213> ORGANISM: Hepatitis C virus

<400> SEQUENCE: 61

Ala Ser Arg Cys Trp Val Ala Met
1               5

<210> SEQ ID NO 62
<211> LENGTH: 9
<212> TYPE: PRT
<213> ORGANISM: Hepatitis C virus

<400> SEQUENCE: 62

Gly Gln Ile Val Gly Gly Val Tyr Leu
1               5

<210> SEQ ID NO 63
<211> LENGTH: 10
<212> TYPE: PRT
<213> ORGANISM: Hepatitis C virus

<400> SEQUENCE: 63

Arg Pro Leu Thr Asp Phe Asp Gln Gly Trp
1               5                   10

<210> SEQ ID NO 64
<211> LENGTH: 10
<212> TYPE: PRT
<213> ORGANISM: Hepatitis C virus

<400> SEQUENCE: 64

Leu Met Gly Tyr Ile Pro Leu Val Gly Ala
1               5                   10

<210> SEQ ID NO 65
<211> LENGTH: 10
```

<212> TYPE: PRT
<213> ORGANISM: Hepatitis C virus

<400> SEQUENCE: 65

Ala Asp Leu Met Gly Tyr Ile Pro Leu Val
1 5 10

<210> SEQ ID NO 66
<211> LENGTH: 16
<212> TYPE: PRT
<213> ORGANISM: Hepatitis C virus

<400> SEQUENCE: 66

Met Ser Tyr Ser Trp Thr Gly Ala Leu Val Thr Pro Cys Ala Glu Glu
 1 5 10 15

<210> SEQ ID NO 67
<211> LENGTH: 9
<212> TYPE: PRT
<213> ORGANISM: Hepatitis C virus

<400> SEQUENCE: 67

Lys His Pro Asp Ala Thr Tyr Ser Arg
 1 5

<210> SEQ ID NO 68
<211> LENGTH: 10
<212> TYPE: PRT
<213> ORGANISM: Hepatitis C virus

<400> SEQUENCE: 68

Lys Leu Val Ala Leu Gly Ile Asn Ala Val
 1 5 10

<210> SEQ ID NO 69
<211> LENGTH: 9
<212> TYPE: PRT
<213> ORGANISM: Hepatitis C virus

<400> SEQUENCE: 69

Gly Asp Phe Asp Ser Val Ile Asp Cys
 1 5

<210> SEQ ID NO 70
<211> LENGTH: 9
<212> TYPE: PRT
<213> ORGANISM: Hepatitis C virus

<400> SEQUENCE: 70

Gly Asn Ala Ser Arg Cys Trp Val Ala
 1 5

<210> SEQ ID NO 71
<211> LENGTH: 9
<212> TYPE: PRT
<213> ORGANISM: Hepatitis C virus

<400> SEQUENCE: 71

Thr Arg Pro Pro Leu Gly Asn Trp Phe
 1 5

<210> SEQ ID NO 72
<211> LENGTH: 9
<212> TYPE: PRT
<213> ORGANISM: Hepatitis C virus

```
<400> SEQUENCE: 72

Val Pro His Pro Asn Ile Glu Glu Val
1               5

<210> SEQ ID NO 73
<211> LENGTH: 9
<212> TYPE: PRT
<213> ORGANISM: Hepatitis C virus

<400> SEQUENCE: 73

Tyr Thr Gly Asp Phe Asp Ser Val Ile
1               5

<210> SEQ ID NO 74
<211> LENGTH: 8
<212> TYPE: PRT
<213> ORGANISM: Hepatitis C virus

<400> SEQUENCE: 74

Ser Trp Ala Ile Lys Trp Glu Tyr
1               5

<210> SEQ ID NO 75
<211> LENGTH: 9
<212> TYPE: PRT
<213> ORGANISM: Homo Sapiens

<400> SEQUENCE: 75

Lys His Pro Asp Ala Thr Tyr Ser Arg
1               5

<210> SEQ ID NO 76
<211> LENGTH: 9
<212> TYPE: PRT
<213> ORGANISM: Hepatitis C virus

<400> SEQUENCE: 76

Gly Asp Phe Asp Ser Val Ile Asp Cys
1               5

<210> SEQ ID NO 77
<211> LENGTH: 9
<212> TYPE: PRT
<213> ORGANISM: Homo sapiens immunodeficiency virus

<400> SEQUENCE: 77

Arg Tyr Leu Lys Asp Gln Gln Leu Leu
1               5

<210> SEQ ID NO 78
<211> LENGTH: 9
<212> TYPE: PRT
<213> ORGANISM: Homo sapiens immunodeficiency virus

<400> SEQUENCE: 78

Ile Val Gly Leu Asn Lys Ile Val Arg
1               5

<210> SEQ ID NO 79
<211> LENGTH: 9
<212> TYPE: PRT
<213> ORGANISM: Homo sapiens immunodeficiency virus

<400> SEQUENCE: 79
```

Glu Ile Tyr Lys Arg Trp Ile Ile Leu
 1               5

<210> SEQ ID NO 80
<211> LENGTH: 9
<212> TYPE: PRT
<213> ORGANISM: Homo sapiens immunodeficiency virus

<400> SEQUENCE: 80

Gly Glu Ile Tyr Lys Arg Trp Ile Ile
 1               5

<210> SEQ ID NO 81
<211> LENGTH: 9
<212> TYPE: PRT
<213> ORGANISM: Homo sapiens immunodeficiency virus

<400> SEQUENCE: 81

Glu Ile Lys Asp Thr Lys Glu Ala Leu
 1               5

<210> SEQ ID NO 82
<211> LENGTH: 8
<212> TYPE: PRT
<213> ORGANISM: Homo sapiens immunodeficiency virus

<400> SEQUENCE: 82

Tyr Leu Lys Asp Gln Gln Leu Leu
 1               5

<210> SEQ ID NO 83
<211> LENGTH: 11
<212> TYPE: PRT
<213> ORGANISM: Homo sapiens immunodeficiency virus

<400> SEQUENCE: 83

Ile Leu Gly Leu Asn Lys Ile Val Arg Met Tyr
 1               5                   10

<210> SEQ ID NO 84
<211> LENGTH: 9
<212> TYPE: PRT
<213> ORGANISM: Homo sapiens immunodeficiency virus

<400> SEQUENCE: 84

Glu Arg Tyr Leu Lys Asp Gln Gln Leu
 1               5

<210> SEQ ID NO 85
<211> LENGTH: 11
<212> TYPE: PRT
<213> ORGANISM: Homo sapiens immunodeficiency virus

<400> SEQUENCE: 85

Tyr His Thr Gln Gly Tyr Phe Pro Gln Trp Gln
 1               5                   10

<210> SEQ ID NO 86
<211> LENGTH: 12
<212> TYPE: PRT
<213> ORGANISM: Homo sapiens immunodeficiency virus

<400> SEQUENCE: 86

Thr Gln Gly Tyr Phe Pro Gln Trp Gln Asn Tyr Thr

-continued 1 5 10

<210> SEQ ID NO 87
<211> LENGTH: 9
<212> TYPE: PRT
<213> ORGANISM: Homo sapiens immunodeficiency virus

<400> SEQUENCE: 87

Gly Arg Ala Phe Val Thr Ile Gly Lys
1 5

<210> SEQ ID NO 88
<211> LENGTH: 9
<212> TYPE: PRT
<213> ORGANISM: Homo sapiens immunodeficiency virus

<400> SEQUENCE: 88

Lys Arg Trp Ile Ile Leu Gly Leu Asn
1 5

<210> SEQ ID NO 89
<211> LENGTH: 10
<212> TYPE: PRT
<213> ORGANISM: Homo sapiens immunodeficiency virus

<400> SEQUENCE: 89

Gln Val Pro Leu Arg Pro Met Thr Tyr Lys
1 5 10

<210> SEQ ID NO 90
<211> LENGTH: 9
<212> TYPE: PRT
<213> ORGANISM: Homo sapiens immunodeficiency virus

<400> SEQUENCE: 90

Thr Gln Gly Tyr Phe Pro Gln Trp Gln
1 5

<210> SEQ ID NO 91
<211> LENGTH: 9
<212> TYPE: PRT
<213> ORGANISM: Homo sapiens immunodeficiency virus

<400> SEQUENCE: 91

His Gln Ala Ile Ser Pro Arg Thr Leu
1 5

<210> SEQ ID NO 92
<211> LENGTH: 12
<212> TYPE: PRT
<213> ORGANISM: Homo sapiens immunodeficiency virus

<400> SEQUENCE: 92

Gln Met Val His Gln Ala Ile Ser Pro Arg Thr Leu
1 5 10

<210> SEQ ID NO 93
<211> LENGTH: 10
<212> TYPE: PRT
<213> ORGANISM: Homo sapiens immunodeficiency virus

<400> SEQUENCE: 93

Met Tyr Ala Pro Pro Ile Gly Gly Gln Ile
1 5 10

```
<210> SEQ ID NO 94
<211> LENGTH: 10
<212> TYPE: PRT
<213> ORGANISM: Homo sapiens immunodeficiency virus

<400> SEQU

```
<211> LENGTH: 9
<212> TYPE: PRT
<213> ORGANISM: Homo sapiens immunodeficiency virus type 1

<400> SEQUENCE: 101

Ser Leu Tyr Asn Thr Val Ala Thr Leu
 1               5

<210> SEQ ID NO 102
<211> LENGTH: 10
<212> TYPE: PRT
<213> ORGANISM: Homo sapiens immunodeficiency virus type 1

<400> SEQUENCE: 102

Arg Gly Pro Gly Arg Ala Phe Val Thr Ile
 1               5                  10

<210> SEQ ID NO 103
<211> LENGTH: 11
<212> TYPE: PRT
<213> ORGANISM: Homo sapiens immunodeficiency virus type 1

<400> SEQUENCE: 103

Arg Leu Arg Asp Leu Leu Leu Ile Val Thr Arg
 1               5                  10

<210> SEQ ID NO 104
<211> LENGTH: 10
<212> TYPE: PRT
<213> ORGANISM: Homo sapiens immunodeficiency virus type 1

<400> SEQUENCE: 104

Gln Val Pro Leu Arg Pro Met Thr Tyr Lys
 1               5                  10

<210> SEQ ID NO 105
<211> LENGTH: 10
<212> TYPE: PRT
<213> ORGANISM: Homo sapiens immunodeficiency virus type 1

<400> SEQUENCE: 105

Thr Val Tyr Tyr Gly Val Pro Val Trp Lys
 1               5                  10

<210> SEQ ID NO 106
<211> LENGTH: 9
<212> TYPE: PRT
<213> ORGANISM: Homo sapiens immunodeficiency virus type 1

<400> SEQUENCE: 106

Arg Leu Arg Pro Gly Gly Lys Lys Lys
 1               5

<210> SEQ ID NO 107
<211> LENGTH: 9
<212> TYPE: PRT
<213> ORGANISM: Homo sapiens immunodeficiency virus type 1

<400> SEQUENCE: 107

Val Tyr Tyr Gly Val Pro Val Trp Lys
 1               5

<210> SEQ ID NO 108
<211> LENGTH: 9
<212> TYPE: PRT
```

-continued

<213> ORGANISM: Homo sapiens immunodeficiency virus type 1

<400> SEQUENCE: 108

Val Pro Leu Arg Pro Met Thr Tyr Lys
1               5

<210> SEQ ID NO 109
<211> LENGTH: 9
<212> TYPE: PRT
<213> ORGANISM: Homo sapiens immunodeficiency virus type 1

<400> SEQUENCE: 109

Ala Ile Phe Gln Ser Ser Met Thr Lys
1               5

<210> SEQ ID NO 110
<211> LENGTH: 12
<212> TYPE: PRT
<213> ORGANISM: Homo sapiens immunodeficiency virus type 1

<400> SEQUENCE: 110

Ala Ala Val Asp Leu Ser His Phe Leu Lys Glu Lys
1               5                   10

<210> SEQ ID NO 111
<211> LENGTH: 12
<212> TYPE: PRT
<213> ORGANISM: Homo sapiens immunodeficiency virus type 1

<400> SEQUENCE: 111

Ala Cys Gln Gly Val Gly Gly Pro Gly Gly His Lys
1               5                   10

<210> SEQ ID NO 112
<211> LENGTH: 10
<212> TYPE: PRT
<213> ORGANISM: Homo sapiens immunodeficiency virus type 1

<400> SEQUENCE: 112

Glu Thr Ile Asn Glu Glu Ala Ala Glu Trp
1               5                   10

<210> SEQ ID NO 113
<211> LENGTH: 10
<212> TYPE: PRT
<213> ORGANISM: Homo sapiens immunodeficiency virus type 1

<400> SEQUENCE: 113

Thr Pro Gly Pro Gly Val Arg Tyr Pro Leu
1               5                   10

<210> SEQ ID NO 114
<211> LENGTH: 8
<212> TYPE: PRT
<213> ORGANISM: Homo sapiens immunodeficiency virus type 1

<400> SEQUENCE: 114

Gly Gly Lys Lys Lys Tyr Lys Leu
1               5

<210> SEQ ID NO 115
<211> LENGTH: 9
<212> TYPE: PRT
<213> ORGANISM: Homo sapiens immunodeficiency virus type 1

```
<400> SEQUENCE: 115

Arg Val Lys Glu Lys Tyr Gln His Leu
  1               5

<210> SEQ ID NO 116
<211> LENGTH: 9
<212> TYPE: PRT
<213> ORGANISM: Homo sapiens immunodeficiency virus type 1

<400> SEQUENCE: 116

Asp Arg Phe Tyr Lys Thr Leu Arg Ala
  1               5

<210> SEQ ID NO 117
<211> LENGTH: 16
<212> TYPE: PRT
<213> ORGANISM: Homo sapiens immunodeficiency virus type 1

<400> SEQUENCE: 117

Gly Val Arg Tyr Pro Leu Thr Phe Gly Trp Cys Tyr Lys Leu Val Pro
  1               5                  10                  15

<210> SEQ ID NO 118
<211> LENGTH: 10
<212> TYPE: PRT
<213> ORGANISM: Homo sapiens immunodeficiency virus type 1

<400> SEQUENCE: 118

Lys Arg Trp Ile Ile Leu Gly Leu Asn Lys
  1               5                  10

<210> SEQ ID NO 119
<211> LENGTH: 9
<212> TYPE: PRT
<213> ORGANISM: EBV

<400> SEQUENCE: 119

Lys Glu His Val Ile Gln Asn Ala Phe
  1               5

<210> SEQ ID NO 120
<211> LENGTH: 10
<212> TYPE: PRT
<213> ORGANISM: EBV

<400> SEQUENCE: 120

Glu Glu Asn Leu Leu Asp Phe Val Arg Phe
  1               5                  10

<210> SEQ ID NO 121
<211> LENGTH: 10
<212> TYPE: PRT
<213> ORGANISM: EBV

<400> SEQUENCE: 121

Asp Thr Pro Leu Ile Pro Leu Thr Ile Phe
  1               5                  10

<210> SEQ ID NO 122
<211> LENGTH: 10
<212> TYPE: PRT
<213> ORGANISM: EBV

<400> SEQUENCE: 122
```

Gln Asn Gly Ala Leu Ala Ile Asn Thr Phe
1               5                   10

<210> SEQ ID NO 123
<211> LENGTH: 9
<212> TYPE: PRT
<213> ORGANISM: EBV

<400> SEQUENCE: 123

Arg Leu Arg Ala Glu Ala Gly Val Lys
1               5

<210> SEQ ID NO 124
<211> LENGTH: 10
<212> TYPE: PRT
<213> ORGANISM: Hepatitis B virus

<400> SEQUENCE: 124

Gly Leu Ser Pro Thr Val Trp Leu Ser Val
1               5                   10

<210> SEQ ID NO 125
<211> LENGTH: 9
<212> TYPE: PRT
<213> ORGANISM: Hepatitis B virus

<400> SEQUENCE: 125

Trp Leu Ser Leu Leu Val Pro Phe Val
1               5

<210> SEQ ID NO 126
<211> LENGTH: 10
<212> TYPE: PRT
<213> ORGANISM: Hepatitis B virus

<400> SEQUENCE: 126

Phe Leu Pro Ser Asp Phe Phe Pro Ser Val
1               5                   10

<210> SEQ ID NO 127
<211> LENGTH: 9
<212> TYPE: PRT
<213> ORGANISM: Hepatitis B virus

<400> SEQUENCE: 127

Phe Leu Leu Ser Leu Gly Ile His Leu
1               5

<210> SEQ ID NO 128
<211> LENGTH: 9
<212> TYPE: PRT
<213> ORGANISM: Hepatitis B virus

<400> SEQUENCE: 128

Ser Leu Tyr Ala Asp Ser Pro Ser Val
1               5

<210> SEQ ID NO 129
<211> LENGTH: 9
<212> TYPE: PRT
<213> ORGANISM: Hepatitis B virus

<400> SEQUENCE: 129

Gly Leu Ser Arg Tyr Val Ala Arg Leu
1               5

```
<210> SEQ ID NO 130
<211> LENGTH: 10
<212> TYPE: PRT
<213> ORGANISM: Hepatitis B virus

<400> SEQUENCE: 130

Leu Leu Val Pro Phe Val Gln Trp Phe Val
 1               5                  10

<210> SEQ ID NO 131
<211> LENGTH: 9
<212> TYPE: PRT
<213> ORGANISM: Hepatitis B virus

<400> SEQUENCE: 131

Ala Leu Met Pro Leu Tyr Ala Cys Ile
 1               5

<210> SEQ ID NO 132
<211> LENGTH: 10
<212> TYPE: PRT
<213> ORGANISM: Hepatitis B virus

<400> SEQUENCE: 132

Leu Leu Pro Ile Phe Phe Cys Leu Trp Val
 1               5                  10

<210> SEQ ID NO 133
<211> LENGTH: 9
<212> TYPE: PRT
<213> ORGANISM: Hepatitis B virus

<400> SEQUENCE: 133

Tyr Met Asp Asp Val Val Leu Gly Ala
 1               5

<210> SEQ ID NO 134
<211> LENGTH: 9
<212> TYPE: PRT
<213> ORGANISM: Hepatitis B virus

<400> SEQUENCE: 134

Leu Leu Leu Cys Leu Ile Phe Leu Leu
 1               5

<210> SEQ ID NO 135
<211> LENGTH: 10
<212> TYPE: PRT
<213> ORGANISM: Hepatitis B virus

<400> SEQUENCE: 135

Leu Leu Asp Tyr Gln Gly Met Leu Pro Val
 1               5                  10

<210> SEQ ID NO 136
<211> LENGTH: 10
<212> TYPE: PRT
<213> ORGANISM: Hepatitis B virus

<400> SEQUENCE: 136

Ser Ile Val Ser Pro Phe Ile Pro Leu Leu
 1               5                  10
```

```
<210> SEQ ID NO 137
<211> LENGTH: 9
<212> TYPE: PRT
<213> ORGANISM: Hepatitis B virus

<400> SEQUENCE: 137

Phe Leu Leu Thr Arg Ile Leu Thr Ile
1               5

<210> SEQ ID NO 138
<211> LENGTH: 9
<212> TYPE: PRT
<213> ORGANISM: Hepatitis B virus

<400> SEQUENCE: 138

Tyr Val Asn Val Asn Met Gly Leu Lys
1               5

<210> SEQ ID NO 139
<211> LENGTH: 11
<212> TYPE: PRT
<213> ORGANISM: Hepatitis B virus

<400> SEQUENCE: 139

Ser Thr Leu Pro Glu Thr Thr Val Val Arg Arg
1               5                   10

<210> SEQ ID NO 140
<211> LENGTH: 12
<212> TYPE: PRT
<213> ORGANISM: Hepatitis B virus

<400> SEQUENCE: 140

Ile Pro Gln Ser Leu Asp Ser Trp Trp Thr Ser Leu
1               5                   10

<210> SEQ ID NO 141
<211> LENGTH: 8
<212> TYPE: PRT
<213> ORGANISM: Hepatitis B virus

<400> SEQUENCE: 141

Met Gly Leu Lys Phe Arg Gln Leu
1               5

<210> SEQ ID NO 142
<211> LENGTH: 9
<212> TYPE: PRT
<213> ORGANISM: Hepatitis B virus
<220> FEATURE:
<221> NAME/KEY: VARIANT
<222> LOCATION: (1)...(9)
<223> OTHER INFORMATION: Xaa = Any Amino Acid

<400> SEQUENCE: 142

Ser Thr Asx Xaa Gln Ser Gly Xaa Gln
1               5

<210> SEQ ID NO 143
<211> LENGTH: 11
<212> TYPE: PRT
<213> ORGANISM: Homo Sapiens cytomegalovirus

<400> SEQUENCE: 143

Phe Ile Ala Gly Asn Ser Ala Tyr Glu Tyr Val
1               5                   10
```

<210> SEQ ID NO 144
<211> LENGTH: 12
<212> TYPE: PRT
<213> ORGANISM: Homo Sapiens cytomegalovirus

<400> SEQUENCE: 144

Ser Asp Glu Glu Glu Ala Ile Val Ala Tyr Thr Leu
1               5                   10

<210> SEQ ID NO 145
<211> LENGTH: 15
<212> TYPE: PRT
<213> ORGANISM: Homo Sapiens cytomegalovirus

<400> SEQUENCE: 145

Asp Asp Val Trp Thr Ser Gly Ser Asp Ser Asp Glu Glu Leu Val
1               5                   10                  15

<210> SEQ ID NO 146
<211> LENGTH: 9
<212> TYPE: PRT
<213> ORGANISM: Homo Sapiens cytomegalovirus

<400> SEQUENCE: 146

Ile Pro Ser Ile Asn Val His His Tyr
1               5

<210> SEQ ID NO 147
<211> LENGTH: 10
<212> TYPE: PRT
<213> ORGANISM: Homo Sapiens cytomegalovirus

<400> SEQUENCE: 147

Asn Leu Val Pro Met Val Ala Thr Val Gln
1               5                   10

<210> SEQ ID NO 148
<211> LENGTH: 15
<212> TYPE: PRT
<213> ORGANISM: Homo Sapiens cytomegalovirus

<400> SEQUENCE: 148

Arg Lys Thr Pro Arg Val Thr Gly Gly Gly Ala Met Ala Gly Ala
1               5                   10                  15

<210> SEQ ID NO 149
<211> LENGTH: 9
<212> TYPE: PRT
<213> ORGANISM: Hepatitis C virus

<400> SEQUENCE: 149

Asp Leu Met Gly Tyr Ile Pro Leu Val
1               5

<210> SEQ ID NO 150
<211> LENGTH: 10
<212> TYPE: PRT
<213> ORGANISM: Hepatitis C virus

<400> SEQUENCE: 150

Leu Leu Ala Leu Leu Ser Cys Leu Thr Val
1               5                   10

```
<210> SEQ ID NO 151
<211> LENGTH: 8
<212> TYPE: PRT
<213> ORGANISM: Hepatitis C virus

<400> SEQUENCE: 151

Ile Leu His Thr Pro Gly Cys Val
 1               5

<210> SEQ ID NO 152
<211> LENGTH: 10
<212> TYPE: PRT
<213> ORGANISM: Hepatitis C virus

<400> SEQUENCE: 152

Gln Leu Arg Arg His Ile Asp Leu Leu Val
 1               5                  10

<210> SEQ ID NO 153
<211> LENGTH: 9
<212> TYPE: PRT
<213> ORGANISM: Hepatitis C virus

<400> SEQUENCE: 153

Asp Leu Cys Gly Ser Val Phe Leu Val
 1               5

<210> SEQ ID NO 154
<211> LENGTH: 9
<212> TYPE: PRT
<213> ORGANISM: Hepatitis C virus

<400> SEQUENCE: 154

Ser Met Val Gly Asn Trp Ala Lys Val
 1               5

<210> SEQ ID NO 155
<211> LENGTH: 9
<212> TYPE: PRT
<213> ORGANISM: Hepatitis C virus

<400> SEQUENCE: 155

His Leu His Gln Asn Ile Val Asp Val
 1               5

<210> SEQ ID NO 156
<211> LENGTH: 9
<212> TYPE: PRT
<213> ORGANISM: Hepatitis C virus

<400> SEQUENCE: 156

Phe Leu Leu Leu Ala Asp Ala Arg Val
 1               5

<210> SEQ ID NO 157
<211> LENGTH: 13
<212> TYPE: PRT
<213> ORGANISM: Hepatitis C virus

<400> SEQUENCE: 157

Gly Leu Arg Asp Leu Ala Val Ala Val Glu Pro Val Val
 1               5                  10

<210> SEQ ID NO 158
<211> LENGTH: 11
```

<212> TYPE: PRT
<213> ORGANISM: Hepatitis C virus

<400> SEQUENCE: 158

Ser Leu Leu Ala Pro Gly Ala Lys Gln Asn Val
1 5 10

<210> SEQ ID NO 159
<211> LENGTH: 10
<212> TYPE: PRT
<213> ORGANISM: Hepatitis C virus

<400> SEQUENCE: 159

Leu Leu Ala Pro Gly Ala Lys Gln Asn Val
1 5 10

<210> SEQ ID NO 160
<211> LENGTH: 10
<212> TYPE: PRT
<213> ORGANISM: Hepatitis C virus

<400> SEQUENCE: 160

Leu Leu Phe Asn Ile Leu Gly Gly Trp Val
1 5 10

<210> SEQ ID NO 161
<211> LENGTH: 9
<212> TYPE: PRT
<213> ORGANISM: Hepatitis C virus

<400> SEQUENCE: 161

Tyr Leu Val Ala Tyr Gln Ala Thr Val
1 5

<210> SEQ ID NO 162
<211> LENGTH: 10
<212> TYPE: PRT
<213> ORGANISM: Hepatitis C virus

<400> SEQUENCE: 162

Tyr Leu Leu Pro Arg Arg Gly Pro Arg Leu
1 5 10

<210> SEQ ID NO 163
<211> LENGTH: 10
<212> TYPE: PRT
<213> ORGANISM: Hepatitis C virus

<400> SEQUENCE: 163

Leu Leu Ala Leu Leu Ser Cys Leu Thr Ile
1 5 10

<210> SEQ ID NO 164
<211> LENGTH: 9
<212> TYPE: PRT
<213> ORGANISM: Hepatitis C virus

<400> SEQUENCE: 164

Ser Leu Met Ala Phe Thr Ala Ala Val
1 5

<210> SEQ ID NO 165
<211> LENGTH: 9
<212> TYPE: PRT
<213> ORGANISM: Hepatitis C virus

```
<400> SEQUENCE: 165

Cys Ile Asn Gly Val Cys Trp Thr Val
 1               5

<210> SEQ ID NO 166
<211> LENGTH: 9
<212> TYPE: PRT
<213> ORGANISM: Hepatitis C virus

<400> SEQUENCE: 166

Leu Leu Cys Pro Ala Gly His Ala Val
 1               5

<210> SEQ ID NO 167
<211> LENGTH: 9
<212> TYPE: PRT
<213> ORGANISM: Hepatitis C virus

<400> SEQUENCE: 167

Ile Leu Asp Ser Phe Asp Pro Leu Val
 1               5

<210> SEQ ID NO 168
<211> LENGTH: 9
<212> TYPE: PRT
<213> ORGANISM: Hepatitis C virus

<400> SEQUENCE: 168

Ile Leu Ala Gly Tyr Gly Ala Gly Val
 1               5

<210> SEQ ID NO 169
<211> LENGTH: 9
<212> TYPE: PRT
<213> ORGANISM: Hepatitis C virus

<400> SEQUENCE: 169

Gly Leu Gln Asp Cys Thr Met Leu Val
 1               5

<210> SEQ ID NO 170
<211> LENGTH: 10
<212> TYPE: PRT
<213> ORGANISM: Hepatitis C virus

<400> SEQUENCE: 170

Thr Gly Ala Pro Val Thr Tyr Ser Thr Tyr
 1               5                  10

<210> SEQ ID NO 171
<211> LENGTH: 9
<212> TYPE: PRT
<213> ORGANISM: Hepatitis C virus

<400> SEQUENCE: 171

His Met Trp Asn Phe Ile Ser Gly Ile
 1               5

<210> SEQ ID NO 172
<211> LENGTH: 9
<212> TYPE: PRT
<213> ORGANISM: Hepatitis C virus

<400> SEQUENCE: 172
```

Arg Val Cys Glu Lys Met Ala Leu Tyr
1               5

<210> SEQ ID NO 173
<211> LENGTH: 8
<212> TYPE: PRT
<213> ORGANISM: Hepatitis C virus

<400> SEQUENCE: 173

Thr Ile Asn Tyr Thr Ile Phe Lys
1               5

<210> SEQ ID NO 174
<211> LENGTH: 8
<212> TYPE: PRT
<213> ORGANISM: Hepatitis C virus

<400> SEQUENCE: 174

Tyr Ile Ser Trp Cys Leu Trp Trp
1               5

<210> SEQ ID NO 175
<211> LENGTH: 9
<212> TYPE: PRT
<213> ORGANISM: Hepatitis C virus

<400> SEQUENCE: 175

Gly Pro Arg Leu Gly Val Arg Ala Thr
1               5

<210> SEQ ID NO 176
<211> LENGTH: 9
<212> TYPE: PRT
<213> ORGANISM: Homo Sapiens immunodeficiency virus type 1

<400> SEQUENCE: 176

Ser Phe Asn Cys Gly Gly Glu Phe Phe
1               5

<210> SEQ ID NO 177
<211> LENGTH: 9
<212> TYPE: PRT
<213> ORGANISM: Homo Sapiens immunodeficiency virus type 1

<400> SEQUENCE: 177

Thr Glu Met Glu Lys Glu Gly Lys Ile
1               5

<210> SEQ ID NO 178
<211> LENGTH: 9
<212> TYPE: PRT
<213> ORGANISM: Homo Sapiens immunodeficiency virus type 1

<400> SEQUENCE: 178

Lys Ile Arg Leu Arg Pro Gly Gly Lys
1               5

<210> SEQ ID NO 179
<211> LENGTH: 10
<212> TYPE: PRT
<213> ORGANISM: Homo Sapiens immunodeficiency virus type 1

<400> SEQUENCE: 179

Arg Leu Arg Pro Gly Gly Lys Lys Lys Tyr

-continued

<210> SEQ ID NO 180
<211> LENGTH: 9
<212> TYPE: PRT
<213> ORGANISM: Homo Sapiens immunodeficiency virus type 1

<400> SEQUENCE: 180

Ala Ile Phe Gln Ser Ser Met Thr Lys
 1               5

<210> SEQ ID NO 181
<211> LENGTH: 9
<212> TYPE: PRT
<213> ORGANISM: Homo Sapiens immunodeficiency virus type 1

<400> SEQUENCE: 181

Thr Leu Tyr Cys Val His Gln Arg Ile
 1               5

<210> SEQ ID NO 182
<211> LENGTH: 10
<212> TYPE: PRT
<213> ORGANISM: Homo Sapiens immunodeficiency virus type 1

<400> SEQUENCE: 182

Ile Tyr Gln Glu Pro Phe Lys Asn Leu Lys
 1               5                   10

<210> SEQ ID NO 183
<211> LENGTH: 9
<212> TYPE: PRT
<213> ORGANISM: Homo Sapiens immunodeficiency virus type 1

<400> SEQUENCE: 183

Lys Tyr Lys Leu Lys His Ile Val Trp
 1               5

<210> SEQ ID NO 184
<211> LENGTH: 10
<212> TYPE: PRT
<213> ORGANISM: Homo Sapiens immunodeficiency virus type 1

<400> SEQUENCE: 184

Leu Phe Cys Ala Ser Asp Ala Lys Ala Tyr
 1               5                   10

<210> SEQ ID NO 185
<211> LENGTH: 11
<212> TYPE: PRT
<213> ORGANISM: Homo Sapiens immunodeficiency virus type 1

<400> SEQUENCE: 185

Gln Ala Ile Ser Pro Arg Thr Leu Asn Ala Trp
 1               5                   10

<210> SEQ ID NO 186
<211> LENGTH: 9
<212> TYPE: PRT
<213> ORGANISM: Homo Sapiens immunodeficiency virus type 1

<400> SEQUENCE: 186

Glu Val Ile Pro Met Phe Ser Ala Leu
 1               5

```
<210> SEQ ID NO 187
<211> LENGTH: 11
<212> TYPE: PRT
<213> ORGANISM: Homo Sapiens immunodeficiency virus type 1

<400> SEQUENCE: 187

Glu Thr Phe Tyr Val Asp Gly Ala Ala Asn Arg
 1               5                  10

<210> SEQ ID NO 188
<211> LENGTH: 11
<212> TYPE: PRT
<213> ORGANISM: Homo Sapiens immunodeficiency virus type 1

<400> SEQUENCE: 188

Arg Leu Arg Asp Leu Leu Leu Ile Val Thr Arg
 1               5                  10

<210> SEQ ID NO 189
<211> LENGTH: 10
<212> TYPE: PRT
<213> ORGANISM: Homo Sapiens immunodeficiency virus type 1

<400> SEQUENCE: 189

Pro Ile Gln Lys Glu Thr Trp Glu Thr Trp
 1               5                  10

<210> SEQ ID NO 190
<211> LENGTH: 9
<212> TYPE: PRT
<213> ORGANISM: Homo Sapiens immunodeficiency virus type 1

<400> SEQUENCE: 190

Arg Ile Lys Gln Ile Ile Asn Met Trp
 1               5

<210> SEQ ID NO 191
<211> LENGTH: 9
<212> TYPE: PRT
<213> ORGANISM: Homo Sapiens immunodeficiency virus type 1

<400> SEQUENCE: 191

Ile Thr Leu Trp Gln Arg Pro Leu Val
 1               5

<210> SEQ ID NO 192
<211> LENGTH: 9
<212> TYPE: PRT
<213> ORGANISM: Homo Sapiens immunodeficiency virus type 1

<400> SEQUENCE: 192

Asp Thr Val Leu Glu Glu Met Asn Leu
 1               5

<210> SEQ ID NO 193
<211> LENGTH: 9
<212> TYPE: PRT
<213> ORGANISM: Homo Sapiens immunodeficiency virus type 1

<400> SEQUENCE: 193

Ile Thr Leu Trp Gln Arg Pro Leu Val
 1               5

<210> SEQ ID NO 194
```

-continued

<211> LENGTH: 9
<212> TYPE: PRT
<213> ORGANISM: Homo Sapiens immunodeficiency virus type 1

<400> SEQUENCE: 194

Ser Pro Arg Thr Leu Asn Ala Trp Val
1 5

<210> SEQ ID NO 195
<211> LENGTH: 9
<212> TYPE: PRT
<213> ORGANISM: Homo Sapiens immunodeficiency virus type 1

<400> SEQUENCE: 195

Ala Thr Pro Gln Asp Leu Asn Thr Met
1 5

<210> SEQ ID NO 196
<211> LENGTH: 10
<212> TYPE: PRT
<213> ORGANISM: Homo Sapiens immunodeficiency virus type 1

<400> SEQUENCE: 196

Arg Pro Asn Asn Asn Thr Arg Lys Ser Ile
1 5 10

<210> SEQ ID NO 197
<211> LENGTH: 9
<212> TYPE: PRT
<213> ORGANISM: Homo Sapiens immunodeficiency virus type 1

<400> SEQUENCE: 197

Ile Pro Arg Arg Ile Arg Gln Gly Leu
1 5

<210> SEQ ID NO 198
<211> LENGTH: 9
<212> TYPE: PRT
<213> ORGANISM: Homo Sapiens immunodeficiency virus type 1

<400> SEQUENCE: 198

Glu Leu Arg Ser Leu Tyr Asn Thr Val
1 5

<210> SEQ ID NO 199
<211> LENGTH: 8
<212> TYPE: PRT
<213> ORGANISM: Homo Sapiens immunodeficiency virus type 1

<400> SEQUENCE: 199

Trp Pro Thr Val Arg Glu Arg Met
1 5

<210> SEQ ID NO 200
<211> LENGTH: 8
<212> TYPE: PRT
<213> ORGANISM: Homo Sapiens immunodeficiency virus type 1

<400> SEQUENCE: 200

Phe Leu Lys Glu Lys Gly Gly Leu
1 5

<210> SEQ ID NO 201
<211> LENGTH: 10
<212> TYPE: PRT

-continued

<213> ORGANISM: Homo Sapiens immunodeficiency virus type 1

<400> SEQUENCE: 201

Lys Ile Arg Leu Arg Pro Gly Gly Lys Lys
1 5 10

<210> SEQ ID NO 202
<211> LENGTH: 9
<212> TYPE: PRT
<213> ORGANISM: Homo Sapiens immunodeficiency virus type 1

<400> SEQUENCE: 202

Ile Arg Leu Arg Pro Gly Gly Lys Lys
1 5

<210> SEQ ID NO 203
<211> LENGTH: 10
<212> TYPE: PRT
<213> ORGANISM: Homo Sapiens immunodeficiency virus type 1

<400> SEQUENCE: 203

Gly Arg Arg Gly Trp Glu Ala Leu Lys Tyr
1 5 10

<210> SEQ ID NO 204
<211> LENGTH: 10
<212> TYPE: PRT
<213> ORGANISM: Homo Sapiens immunodeficiency virus type 1

<400> SEQUENCE: 204

Gln Val Pro Leu Arg Pro Met Thr Tyr Lys
1 5 10

<210> SEQ ID NO 205
<211> LENGTH: 8
<212> TYPE: PRT
<213> ORGANISM: Homo Sapiens immunodeficiency virus type 1

<400> SEQUENCE: 205

Arg Tyr Leu Lys Asp Gln Gln Leu
1 5

<210> SEQ ID NO 206
<211> LENGTH: 10
<212> TYPE: PRT
<213> ORGANISM: Homo Sapiens immunodeficiency virus type 1

<400> SEQUENCE: 206

Arg Arg Gln Asp Ile Leu Asp Leu Trp Ile
1 5 10

<210> SEQ ID NO 207
<211> LENGTH: 8
<212> TYPE: PRT
<213> ORGANISM: Homo Sapiens immunodeficiency virus type 1

<400> SEQUENCE: 207

Arg Tyr Pro Leu Thr Phe Gly Trp
1 5

<210> SEQ ID NO 208
<211> LENGTH: 9
<212> TYPE: PRT
<213> ORGANISM: Homo Sapiens immunodeficiency virus type 1

```
<400> SEQUENCE: 208

Trp Ala Ser Arg Glu Leu Glu Arg Phe
 1               5

<210> SEQ ID NO 209
<211> LENGTH: 9
<212> TYPE: PRT
<213> ORGANISM: Homo Sapiens immunodeficiency virus type 1

<400> SEQUENCE: 209

Thr Val Leu Asp Val Gly Asp Ala Tyr
 1               5

<210> SEQ ID NO 210
<211> LENGTH: 11
<212> TYPE: PRT
<213> ORGANISM: Homo Sapiens immunodeficiency virus type 1

<400> SEQUENCE: 210

Val Pro Val Trp Lys Glu Ala Thr Thr Thr Leu
 1               5                  10

<210> SEQ ID NO 211
<211> LENGTH: 9
<212> TYPE: PRT
<213> ORGANISM: Homo Sapiens immunodeficiency virus type 1

<400> SEQUENCE: 211

Asn Ser Ser Lys Val Ser Gln Asn Tyr
 1               5

<210> SEQ ID NO 212
<211> LENGTH: 9
<212> TYPE: PRT
<213> ORGANISM: Homo Sapiens immunodeficiency virus type 1

<400> SEQUENCE: 212

Pro Pro Ile Pro Val Gly Asp Ile Tyr
 1               5

<210> SEQ ID NO 213
<211> LENGTH: 9
<212> TYPE: PRT
<213> ORGANISM: Homo Sapiens immunodeficiency virus type 1

<400> SEQUENCE: 213

His Pro Asp Ile Val Ile Tyr Gln Tyr
 1               5

<210> SEQ ID NO 214
<211> LENGTH: 9
<212> TYPE: PRT
<213> ORGANISM: Homo Sapiens immunodeficiency virus type 1

<400> SEQUENCE: 214

Thr Ala Val Pro Trp Asn Ala Ser Trp
 1               5

<210> SEQ ID NO 215
<211> LENGTH: 9
<212> TYPE: PRT
<213> ORGANISM: Homo Sapiens immunodeficiency virus type 1

<400> SEQUENCE: 215
```

```
Asn Pro Val Pro Val Gly Asn Ile Tyr
 1               5
```

<210> SEQ ID NO 216
<211> LENGTH: 9
<212> TYPE: PRT
<213> ORGANISM: Homo Sapiens immunodeficiency virus type 1

<400> SEQUENCE: 216

```
Tyr Phe Pro Asp Trp Gln Asn Tyr Thr
 1               5
```

<210> SEQ ID NO 217
<211> LENGTH: 9
<212> TYPE: PRT
<213> ORGANISM: Homo Sapiens immunodeficiency virus type 1

<400> SEQUENCE: 217

```
Gly His Gln Ala Ala Met Gln Met Leu
 1               5
```

<210> SEQ ID NO 218
<211> LENGTH: 10
<212> TYPE: PRT
<213> ORGANISM: Homo Sapiens immunodeficiency virus type 1

<400> SEQUENCE: 218

```
Arg Leu Arg Pro Gly Gly Lys Lys Lys Tyr
 1               5                  10
```

<210> SEQ ID NO 219
<211> LENGTH: 9
<212> TYPE: PRT
<213> ORGANISM: Homo Sapiens immunodeficiency virus type 1

<400> SEQUENCE: 219

```
Tyr Pro Gly Ile Lys Val Arg Gln Leu
 1               5
```

<210> SEQ ID NO 220
<211> LENGTH: 10
<212> TYPE: PRT
<213> ORGANISM: Homo Sapiens immunodeficiency virus type 1

<400> SEQUENCE: 220

```
Gly Ala Glu Thr Phe Tyr Val Asp Gly Ala
 1               5                  10
```

<210> SEQ ID NO 221
<211> LENGTH: 9
<212> TYPE: PRT
<213> ORGANISM: Homo Sapiens immunodeficiency virus type 1

<400> SEQUENCE: 221

```
Asn Ala Asn Pro Asp Cys Lys Thr Ile
 1               5
```

<210> SEQ ID NO 222
<211> LENGTH: 8
<212> TYPE: PRT
<213> ORGANISM: Homo Sapiens immunodeficiency virus type 1

<400> SEQUENCE: 222

```
Arg Met Tyr Ser Pro Thr Ser Ile
 1               5
```

<210> SEQ ID NO 223
<211> LENGTH: 10
<212> TYPE: PRT
<213> ORGANISM: Homo Sapiens immunodeficiency virus type 1

<400> SEQUENCE: 223

Val Pro Val Trp Lys Glu Ala Thr Thr Thr
1               5                   10

<210> SEQ ID NO 224
<211> LENGTH: 9
<212> TYPE: PRT
<213> ORGANISM: Homo Sapiens immunodeficiency virus type 1

<400> SEQUENCE: 224

Ile Ser Pro Arg Thr Leu Asn Ala Trp
1               5

<210> SEQ ID NO 225
<211> LENGTH: 10
<212> TYPE: PRT
<213> ORGANISM: Homo Sapiens immunodeficiency virus type 1

<400> SEQUENCE: 225

Thr Ser Thr Leu Gln Glu Gln Ile Gly Trp
1               5                   10

<210> SEQ ID NO 226
<211> LENGTH: 11
<212> TYPE: PRT
<213> ORGANISM: Homo Sapiens immunodeficiency virus type 1

<400> SEQUENCE: 226

Lys Ala Phe Ser Pro Glu Val Ile Pro Met Phe
1               5                   10

<210> SEQ ID NO 227
<211> LENGTH: 9
<212> TYPE: PRT
<213> ORGANISM: Homo Sapiens immunodeficiency virus type 1

<400> SEQUENCE: 227

Gln Ala Ser Gln Glu Val Lys Asn Trp
1               5

<210> SEQ ID NO 228
<211> LENGTH: 9
<212> TYPE: PRT
<213> ORGANISM: Homo Sapiens immunodeficiency virus type 1

<400> SEQUENCE: 228

Gln Ala Ser Gln Asp Val Lys Asn Trp
1               5

<210> SEQ ID NO 229
<211> LENGTH: 10
<212> TYPE: PRT
<213> ORGANISM: Homo Sapiens immunodeficiency virus type 1

<400> SEQUENCE: 229

His Thr Gln Gly Tyr Phe Pro Asp Trp Gln
1               5                   10

-continued

<210> SEQ ID NO 230
<211> LENGTH: 9
<212> TYPE: PRT
<213> ORGANISM: Homo Sapiens immunodeficiency virus type 1

<400> SEQUENCE: 230

Tyr Phe Pro Asp Trp Gln Asn Tyr Thr
1 5

<210> SEQ ID NO 231
<211> LENGTH: 10
<212> TYPE: PRT
<213> ORGANISM: Homo Sapiens immunodeficiency virus type 1

<400> SEQUENCE: 231

Thr Ser Thr Leu Gln Glu Gln Ile Gly Trp
1 5 10

<210> SEQ ID NO 232
<211> LENGTH: 10
<212> TYPE: PRT
<213> ORGANISM: Homo Sapiens immunodeficiency virus type 1

<400> SEQUENCE: 232

Arg Leu Arg Pro Gly Gly Lys Lys Lys Tyr
1 5 10

<210> SEQ ID NO 233
<211> LENGTH: 10
<212> TYPE: PRT
<213> ORGANISM: Homo Sapiens immunodeficiency virus type 1

<400> SEQUENCE: 233

Leu Gly Leu Asn Lys Ile Val Arg Met Tyr
1 5 10

<210> SEQ ID NO 234
<211> LENGTH: 12
<212> TYPE: PRT
<213> ORGANISM: Homo Sapiens immunodeficiency virus type 1

<400> SEQUENCE: 234

Leu Val Gly Lys Leu Asn Trp Ala Ser Gln Ile Tyr
1 5 10

<210> SEQ ID NO 235
<211> LENGTH: 10
<212> TYPE: PRT
<213> ORGANISM: Homo Sapiens immunodeficiency virus type 1

<400> SEQUENCE: 235

Ile Leu Lys Glu Pro Val His Gly Val Tyr
1 5 10

<210> SEQ ID NO 236
<211> LENGTH: 11
<212> TYPE: PRT
<213> ORGANISM: Homo Sapiens immunodeficiency virus type 1

<400> SEQUENCE: 236

Thr Gln Gly Tyr Phe Pro Asp Trp Gln Asn Tyr
1 5 10

<210> SEQ ID NO 237
<211> LENGTH: 8

```
<212> TYPE: PRT
<213> ORGANISM: Homo Sapiens immunodeficiency virus type 1

<400> SEQUENCE: 237

Ala Val Asp Leu Ser His Phe Leu
1

```
<400> SEQUENCE: 244

Thr Pro Gly Pro Gly Val Arg Tyr Pro Leu
1               5                   10

<210> SEQ ID NO 245
<211> LENGTH: 9
<212> TYPE: PRT
<213> ORGANISM: Homo Sapiens immunodeficiency virus type 1

<400> SEQUENCE: 245

Gln Ala Ser Gln Glu Val Lys Asn Trp
1               5

<210> SEQ ID NO 246
<211> LENGTH: 10
<212> TYPE: PRT
<213> ORGANISM: Homo Sapiens immunodeficiency virus type 1

<400> SEQUENCE: 246

Val Pro Leu Asp Glu Asp Phe Arg Lys Tyr
1               5                   10

<210> SEQ ID NO 247
<211> LENGTH: 9
<212> TYPE: PRT
<213> ORGANISM: Homo Sapiens immunodeficiency virus

<400> SEQUENCE: 247

Asn Pro Asp Ile Val Ile Tyr Gln Tyr
1               5

<210> SEQ ID NO 248
<211> LENGTH: 9
<212> TYPE: PRT
<213> ORGANISM: Homo Sapiens immunodeficiency virus

<400> SEQUENCE: 248

Arg Ala Ile Glu Ala Gln Ala His Leu
1               5

<210> SEQ ID NO 249
<211> LENGTH: 8
<212> TYPE: PRT
<213> ORGANISM: Homo Sapiens immunodeficiency virus

<400> SEQUENCE: 249

Thr Ala Phe Thr Ile Pro Ser Ile
1               5

<210> SEQ ID NO 250
<211> LENGTH: 10
<212> TYPE: PRT
<213> ORGANISM: Homo Sapiens immunodeficiency virus

<400> SEQUENCE: 250

Val His Pro Val His Ala Gly Pro Ile Ala
1               5                   10

<210> SEQ ID NO 251
<211> LENGTH: 10
<212> TYPE: PRT
<213> ORGANISM: Homo Sapiens immunodeficiency virus

<400> SEQUENCE: 251
```

```
Asn Cys Ser Phe Asn Ile Ser Thr Ser Ile
1               5                   10
```

<210> SEQ ID NO 252
<211> LENGTH: 9
<212> TYPE: PRT
<213> ORGANISM: Homo Sapiens immunodeficiency virus

<400> SEQUENCE: 252

```
Cys Thr Asn Val Ser Thr Val Gln Cys
1               5
```

<210> SEQ ID NO 253
<211> LENGTH: 9
<212> TYPE: PRT
<213> ORGANISM: Homo Sapiens immunodeficiency virus

<400> SEQUENCE: 253

```
Ile Gly Pro Gly Arg Ala Phe His Thr
1               5
```

<210> SEQ ID NO 254
<211> LENGTH: 9
<212> TYPE: PRT
<213> ORGANISM: Homo Sapiens immunodeficiency virus

<400> SEQUENCE: 254

```
Asn Pro Asp Ile Val Ile Tyr Gln Tyr
1               5
```

<210> SEQ ID NO 255
<211> LENGTH: 10
<212> TYPE: PRT
<213> ORGANISM: Homo Sapiens immunodeficiency virus

<400> SEQUENCE: 255

```
Glu Pro Ile Val Gly Ala Glu Thr Phe Tyr
1               5                   10
```

<210> SEQ ID NO 256
<211> LENGTH: 9
<212> TYPE: PRT
<213> ORGANISM: Homo Sapiens immunodeficiency virus

<400> SEQUENCE: 256

```
Glu Pro Ile Val Gly Ala Glu Thr Phe
1               5
```

<210> SEQ ID NO 257
<211> LENGTH: 9
<212> TYPE: PRT
<213> ORGANISM: Homo Sapiens immunodeficiency virus

<400> SEQUENCE: 257

```
Ser Pro Ala Ile Phe Gln Ser Ser Met
1               5
```

<210> SEQ ID NO 258
<211> LENGTH: 10
<212> TYPE: PRT
<213> ORGANISM: Homo Sapiens immunodeficiency virus

<400> SEQUENCE: 258

```
Val Pro Leu Asp Lys Asp Phe Arg Lys Tyr
```

-continued

<210> SEQ ID NO 259
<211> LENGTH: 9
<212> TYPE: PRT
<213> ORGANISM: Homo Sapiens immunodeficiency virus

<400> SEQUENCE: 259

Ile Pro Leu Thr Glu Glu Ala Glu Leu
 1               5

<210> SEQ ID NO 260
<211> LENGTH: 11
<212> TYPE: PRT
<213> ORGANISM: Homo Sapiens immunodeficiency virus

<400> SEQUENCE: 260

Arg Pro Gln Val Pro Leu Arg Pro Met Thr Tyr
 1               5                  10

<210> SEQ ID NO 261
<211> LENGTH: 9
<212> TYPE: PRT
<213> ORGANISM: Homo Sapiens immunodeficiency virus

<400> SEQUENCE: 261

Phe Pro Val Arg Pro Gln Val Pro Leu
 1               5

<210> SEQ ID NO 262
<211> LENGTH: 9
<212> TYPE: PRT
<213> ORGANISM: Homo Sapiens immunodeficiency virus

<400> SEQUENCE: 262

Asp Pro Asn Pro Gln Glu Val Val Leu
 1               5

<210> SEQ ID NO 263
<211> LENGTH: 9
<212> TYPE: PRT
<213> ORGANISM: Homo Sapiens immunodeficiency virus

<400> SEQUENCE: 263

Arg Pro Ile Val Ser Thr Gln Leu Leu
 1               5

<210> SEQ ID NO 264
<211> LENGTH: 9
<212> TYPE: PRT
<213> ORGANISM: Homo Sapiens immunodeficiency virus

<400> SEQUENCE: 264

Ile Pro Leu Thr Glu Glu Ala Glu Leu
 1               5

<210> SEQ ID NO 265
<211> LENGTH: 9
<212> TYPE: PRT
<213> ORGANISM: Homo Sapiens immunodeficiency virus

<400> SEQUENCE: 265

Asp Pro Asn Pro Gln Glu Val Val Leu
 1               5

```
<210> SEQ ID NO 266
<211> LENGTH: 9
<212> TYPE: PRT
<213> ORGANISM: Homo Sapiens immunodeficiency virus type 2

<400> SEQUENCE: 266

Ala Met Gln Met Leu Lys Glu Thr Ile
1               5

<210> SEQ ID NO 267
<211> LENGTH: 9
<212> TYPE: PRT
<213> ORGANISM: Homo Sapiens immunodeficiency virus type 2

<400> SEQUENCE: 267

Thr Pro Tyr Asp Ile Asn Gln Met Leu
1               5

<210> SEQ ID NO 268
<211> LENGTH: 10
<212> TYPE: PRT
<213> ORGANISM: Homo Sapiens immunodeficiency virus type 1

<400> SEQUENCE: 268

Arg Arg Trp Ile Gln Leu Gly Leu Gln Lys
1               5                   10

<210> SEQ ID NO 269
<211> LENGTH: 15
<212> TYPE: PRT
<213> ORGANISM: Homo Sapiens immunodeficiency virus type 1

<400> SEQUENCE: 269

Gly Ile Trp Gly Cys Ser Gly Lys Leu Ile Cys Thr Thr Ala Val
1               5                   10                  15

<210> SEQ ID NO 270
<211> LENGTH: 15
<212> TYPE: PRT
<213> ORGANISM: Homo Sapiens immunodeficiency virus type 1

<400> SEQUENCE: 270

Ala Leu Ile Trp Glu Asp Leu Arg Ser Leu Cys Leu Phe Ser Tyr
1               5                   10                  15

<210> SEQ ID NO 271
<211> LENGTH: 9
<212> TYPE: PRT
<213> ORGANISM: Homo Sapiens papillomavirus type 6b

<400> SEQUENCE: 271

Gly Leu His Cys Tyr Glu Gln Leu Val
1               5

<210> SEQ ID NO 272
<211> LENGTH: 9
<212> TYPE: PRT
<213> ORGANISM: Homo Sapiens papillomavirus type 6b

<400> SEQUENCE: 272

Pro Leu Lys Gln His Phe Gln Ile Val
1               5

<210> SEQ ID NO 273
```

```
<211> LENGTH: 9
<212> TYPE: PRT
<213> ORGANISM: Homo Sapiens papillomavirus type 11

<400> SEQUENCE: 273

Arg Leu Val Thr Leu Lys Asp Ile Val
 1               5

<210> SEQ ID NO 274
<211> LENGTH: 9
<212> TYPE: PRT
<213> ORGANISM: Homo Sapiens papillomavirus type 16

<400> SEQUENCE: 274

Thr Leu Gly Ile Val Cys Pro Ile Cys
 1               5

<210> SEQ ID NO 275
<211> LENGTH: 9
<212> TYPE: PRT
<213> ORGANISM: Homo Sapiens papillomavirus type 16

<400> SEQUENCE: 275

Gly Thr Leu Gly Ile Val Cys Pro Ile
 1               5

<210> SEQ ID NO 276
<211> LENGTH: 9
<212> TYPE: PRT
<213> ORGANISM: Homo Sapiens papillomavirus type 16

<400> SEQUENCE: 276

Met Leu Asp Leu Gln Pro Glu Thr Thr
 1               5

<210> SEQ ID NO 277
<211> LENGTH: 10
<212> TYPE: PRT
<213> ORGANISM: Homo Sapiens papillomavirus type 16

<400> SEQUENCE: 277

Tyr Met Leu Asp Leu Gln Pro Glu Thr Thr
 1               5                  10

<210> SEQ ID NO 278
<211> LENGTH: 8
<212> TYPE: PRT
<213> ORGANISM: Homo Sapiens papillomavirus type 16

<400> SEQUENCE: 278

Arg Pro Arg Lys Leu Pro Gln Leu
 1               5

<210> SEQ ID NO 279
<211> LENGTH: 9
<212> TYPE: PRT
<213> ORGANISM: Homo Sapiens papillomavirus type 16

<400> SEQUENCE: 279

Arg Ala His Tyr Asn Ile Val Thr Phe
 1               5

<210> SEQ ID NO 280
<211> LENGTH: 8
<212> TYPE: PRT
```

```
<213> ORGANISM: HSV

<400> SEQUENCE: 280

Ser Ser Ile Glu Phe Ala Arg Leu
 1               5

<210> SEQ ID NO 281
<211> LENGTH: 9
<212> TYPE: PRT
<213> ORGANISM: HSV-1

<400> SEQUENCE: 281

Gly Ile Gly Ile Gly Val Leu Ala Ala
 1               5

<210> SEQ ID NO 282
<211> LENGTH: 9
<212> TYPE: PRT
<213> ORGANISM: HSV-1

<400> SEQUENCE: 282

Asp Tyr Ala Thr Leu Gly Val Gly Val
 1               5

<210> SEQ ID NO 283
<211> LENGTH: 11
<212> TYPE: PRT
<213> ORGANISM: HSV-1

<400> SEQUENCE: 283

Leu Tyr Arg Thr Phe Ala Gly Asn Pro Arg Ala
 1               5                  10

<210> SEQ ID NO 284
<211> LENGTH: 8
<212> TYPE: PRT
<213> ORGANISM: HSV-1

<400> SEQUENCE: 284

Gln Thr Phe Asp Phe Gly Arg Leu
 1               5

<210> SEQ ID NO 285
<211> LENGTH: 9
<212> TYPE: PRT
<213> ORGANISM: HSV-2

<400> SEQUENCE: 285

Gly Ala Gly Ile Gly Val Ala Val Leu
 1               5

<210> SEQ ID NO 286
<211> LENGTH: 9
<212> TYPE: PRT
<213> ORGANISM: Homo sapiens T-cell lymphotropic virus type 1

<400> SEQUENCE: 286

Leu Leu Phe Gly Tyr Pro Val Tyr Val
 1               5

<210> SEQ ID NO 287
<211> LENGTH: 9
<212> TYPE: PRT
<213> ORGANISM: Haemophilus influenzae
```

```
<400> SEQUENCE: 287

Gly Ile Leu Gly Phe Val Phe Thr Leu
 1               5

<210> SEQ ID NO 288
<211> LENGTH: 10
<212> TYPE: PRT
<213> ORGANISM: haemophilus influenzae

<400> SEQUENCE: 288

Ile Leu Gly Phe Val Phe Thr Leu Thr Val
 1               5                  10

<210> SEQ ID NO 289
<211> LENGTH: 9
<212> TYPE: PRT
<213> ORGANISM: haemophilus influenzae

<400> SEQUENCE: 289

Ile Leu Arg Gly Ser Val Ala His Lys
 1               5

<210> SEQ ID NO 290
<211> LENGTH: 9
<212> TYPE: PRT
<213> ORGANISM: haemophilus influenzae

<400> SEQUENCE: 290

Lys Thr Gly Gly Pro Ile Tyr Lys Arg
 1               5

<210> SEQ ID NO 291
<211> LENGTH: 9
<212> TYPE: PRT
<213> ORGANISM: haemophilus influenzae

<400> SEQUENCE: 291

Glu Leu Arg Ser Arg Tyr Trp Ala Ile
 1               5

<210> SEQ ID NO 292
<211> LENGTH: 8
<212> TYPE: PRT
<213> ORGANISM: haemophilus influenzae

<400> SEQUENCE: 292

Leu Arg Ser Arg Tyr Trp Ala Ile
 1               5

<210> SEQ ID NO 293
<211> LENGTH: 9
<212> TYPE: PRT
<213> ORGANISM: haemophilus influenzae

<400> SEQUENCE: 293

Glu Asp Leu Arg Val Leu Ser Phe Ile
 1               5

<210> SEQ ID NO 294
<211> LENGTH: 9
<212> TYPE: PRT
<213> ORGANISM: haemophilus influenzae

<400> SEQUENCE: 294
```

```
Gly Glu Ile Ser Pro Leu Pro Ser Leu
1               5

<210> SEQ ID NO 295
<211> LENGTH: 9
<212> TYPE: PRT
<213> ORGANISM: haemophilus influenzae

<400> SEQUENCE: 295

Phe Glu Asp Leu Arg Val Leu Ser Phe
1               5

<210> SEQ ID NO 296
<211> LENGTH: 9
<212> TYPE: PRT
<213> ORGANISM: haemophilus influenzae

<400> SEQUENCE: 296

Val Ser Asp Gly Gly Pro Asn Leu Tyr
1               5

<210> SEQ ID NO 297
<211> LENGTH: 9
<212> TYPE: PRT
<213> ORGANISM: haemophilus influenzae

<400> SEQUENCE: 297

Cys Thr Glu Leu Lys Leu Ser Asp Tyr
1               5

<210> SEQ ID NO 298
<211> LENGTH: 9
<212> TYPE: PRT
<213> ORGANISM: haemophilus influenzae

<400> SEQUENCE: 298

Ala Ile Met Asp Lys Asn Ile Ile Leu
1               5

<210> SEQ ID NO 299
<211> LENGTH: 10
<212> TYPE: PRT
<213> ORGANISM: haemophilus influenzae

<400> SEQUENCE: 299

Ile Met Asp Lys Asn Ile Ile Leu Lys Ala
1               5                   10

<210> SEQ ID NO 300
<211> LENGTH: 9
<212> TYPE: PRT
<213> ORGANISM: haemophilus influenzae

<400> SEQUENCE: 300

Ser Arg Tyr Trp Ala Ile Arg Thr Arg
1               5

<210> SEQ ID NO 301
<211> LENGTH: 9
<212> TYPE: PRT
<213> ORGANISM: haemophilus influenzae

<400> SEQUENCE: 301

Thr Tyr Gln Arg Thr Arg Ala Leu Val
1               5
```

-continued

<210> SEQ ID NO 302
<211> LENGTH: 10
<212> TYPE: PRT
<213> ORGANISM: haemophilus influenzae

<400> SEQUENCE: 302

Thr Tyr Val Ser Val Ser Thr Ser Thr Leu
 1               5                  10

<210> SEQ ID NO 303
<211> LENGTH: 9
<212> TYPE: PRT
<213> ORGANISM: haemophilus influenzae

<400> SEQUENCE: 303

Ile Tyr Ser Thr Val Ala Ser Ser Leu
 1               5

<210> SEQ ID NO 304
<211> LENGTH: 8
<212> TYPE: PRT
<213> ORGANISM: haemophilus influenzae

<400> SEQUENCE: 304

Phe Glu Ala Asn Gly Asn Leu Ile
 1               5

<210> SEQ ID NO 305
<211> LENGTH: 9
<212> TYPE: PRT
<213> ORGANISM: haemophilus influenzae

<400> SEQUENCE: 305

Ile Glu Gly Gly Trp Thr Gly Met Ile
 1               5

<210> SEQ ID NO 306
<211> LENGTH: 8
<212> TYPE: PRT
<213> ORGANISM: haemophilus influenzae

<400> SEQUENCE: 306

Ser Asp Tyr Glu Gly Arg Leu Ile
 1               5

<210> SEQ ID NO 307
<211> LENGTH: 9
<212> TYPE: PRT
<213> ORGANISM: haemophilus influenzae

<400> SEQUENCE: 307

Glu Glu Gly Ala Ile Val Gly Glu Ile
 1               5

<210> SEQ ID NO 308
<211> LENGTH: 9
<212> TYPE: PRT
<213> ORGANISM: haemophilus influenzae

<400> SEQUENCE: 308

Ala Ser Asn Glu Asn Met Glu Thr Met
 1               5

```
<210> SEQ ID NO 309
<211> LENGTH: 9
<212> TYPE: PRT
<213> ORGANISM: haemophilus influenzae

<400> SEQUENCE: 309

Ala Ser Asn Glu Asn Met Asp Ala Met
 1               5

<210> SEQ ID NO 310
<211> LENGTH: 10
<212> TYPE: PRT
<213> ORGANISM: haemophilus influenzae

<400> SEQUENCE: 310

Lys Leu Gly Glu Phe Tyr Asn Gln Met Met
 1               5                  10

<210> SEQ ID NO 311
<211> LENGTH: 10
<212> TYPE: PRT
<213> ORGANISM: haemophilus influenzae

<400> SEQUENCE: 311

Lys Ala Gly Glu Phe Tyr Asn Gln Met Met
 1               5                  10

<210> SEQ ID NO 312
<211> LENGTH: 9
<212> TYPE: PRT
<213> ORGANISM: haemophilus influenzae

<400> SEQUENCE: 312

Leu Tyr Gln Asn Val Gly Thr Tyr Val
 1               5

<210> SEQ ID NO 313
<211> LENGTH: 10
<212> TYPE: PRT
<213> ORGANISM: haemophilus influenzae

<400> SEQUENCE: 313

Thr Tyr Val Ser Val Gly Thr Ser Thr Leu
 1               5                  10

<210> SEQ ID NO 314
<211> LENGTH: 9
<212> TYPE: PRT
<213> ORGANISM: haemophilus influenzae

<400> SEQUENCE: 314

Val Tyr Gln Ile Leu Ala Ile Tyr Ala
 1               5

<210> SEQ ID NO 315
<211> LENGTH: 9
<212> TYPE: PRT
<213> ORGANISM: haemophilus influenzae

<400> SEQUENCE: 315

Ile Tyr Ala Thr Val Ala Gly Ser Leu
 1               5

<210> SEQ ID NO 316
<211> LENGTH: 10
```

```
<212> TYPE: PRT
<213> ORGANISM: haemophilus influenzae

<400> SEQUENCE: 316

Thr Tyr Val Ser Val Gly Thr Ser Thr Ile
 1               5                  10

<210> SEQ ID NO 317
<211> LENGTH: 8
<212> TYPE: PRT
<213> ORGANISM: Haemophilus influenzae

<400> SEQUENCE: 317

Phe Glu Ser Thr Gly Asn Leu Ile
 1               5

<210> SEQ ID NO 318
<211> LENGTH: 9
<212> TYPE: PRT
<213> ORGANISM: JHMV

<400> SEQUENCE: 318

Ala Pro Thr Ala Gly Ala Phe Phe Phe
 1               5

<210> SEQ ID NO 319
<211> LENGTH: 9
<212> TYPE: PRT
<213> ORGANISM: LCMV

<400> SEQUENCE: 319

Arg Pro Gln Ala Ser Gly Val Tyr Met
 1               5

<210> SEQ ID NO 320
<211> LENGTH: 9
<212> TYPE: PRT
<213> ORGANISM: LCMV

<400> SEQUENCE: 320

Phe Gln Pro Gln Asn Gly Gln Phe Ile
 1               5

<210> SEQ ID NO 321
<211> LENGTH: 11
<212> TYPE: PRT
<213> ORGANISM: LCMV

<400> SEQUENCE: 321

Ser Gly Val Glu Asn Pro Gly Gly Tyr Cys Leu
 1               5                  10

<210> SEQ ID NO 322
<211> LENGTH: 10
<212> TYPE: PRT
<213> ORGANISM: LCMV

<400> SEQUENCE: 322

Lys Ala Val Tyr Asn Phe Ala Thr Cys Gly
 1               5                  10

<210> SEQ ID NO 323
<211> LENGTH: 9
<212> TYPE: PRT
<213> ORGANISM: MCMV
```

```
<400> SEQUENCE: 323

Tyr Pro His Phe Met Pro Thr Asn Leu
1               5

<210> SEQ ID NO 324
<211> LENGTH: 9
<212> TYPE: PRT
<213> ORGANISM: MHV

<400> SEQUENCE: 324

Cys Leu Ser Trp Asn Gly Pro His Leu
1               5

<210> SEQ ID NO 325
<211> LENGTH: 9
<212> TYPE: PRT
<213> ORGANISM: MMTV

<400> SEQUENCE: 325

Ser Phe Ala Val Ala Thr Thr Ala Leu
1               5

<210> SEQ ID NO 326
<211> LENGTH: 9
<212> TYPE: PRT
<213> ORGANISM: MMTV

<400> SEQUENCE: 326

Ser Tyr Glu Thr Phe Ile Ser Arg Leu
1               5

<210> SEQ ID NO 327
<211> LENGTH: 8
<212> TYPE: PRT
<213> ORGANISM: MMTV

<400> SEQUENCE: 327

Ala Asn Tyr Asp Phe Ile Cys Val
1               5

<210> SEQ ID NO 328
<211> LENGTH: 8
<212> TYPE: PRT
<213> ORGANISM: Murine Leukemia virus

<400> SEQUENCE: 328

Lys Ser Pro Trp Phe Thr Thr Leu
1               5

<210> SEQ ID NO 329
<211> LENGTH: 8
<212> TYPE: PRT
<213> ORGANISM: Murine leukemia virus

<400> SEQUENCE: 329

Ser Ser Trp Asp Phe Ile Thr Val
1               5

<210> SEQ ID NO 330
<211> LENGTH: 9
<212> TYPE: PRT
<213> ORGANISM: Murine leukemia virus

<400> SEQUENCE: 330
```

-continued

Cys Cys Leu Cys Leu Thr Val Phe Leu
1 5

<210> SEQ ID NO 331
<211> LENGTH: 9
<212> TYPE: PRT
<213> ORGANISM: Polio virus

<400> SEQUENCE: 331

Ser Pro Ser Tyr Val Tyr His Gln Phe
1 5

<210> SEQ ID NO 332
<211> LENGTH: 11
<212> TYPE: PRT
<213> ORGANISM: Polio virus

<400> SEQUENCE: 332

Ser Arg Arg Tyr Pro Asp Ala Val Tyr Leu His
1 5 10

<210> SEQ ID NO 333
<211> LENGTH: 9
<212> TYPE: PRT
<213> ORGANISM: MV

<400> SEQUENCE: 333

Arg Arg Tyr Pro Asp Ala Val Tyr Leu
1 5

<210> SEQ ID NO 334
<211> LENGTH: 9
<212> TYPE: PRT
<213> ORGANISM: MV

<400> SEQUENCE: 334

Tyr Pro Ala Leu Gly Leu His Glu Phe
1 5

<210> SEQ ID NO 335
<211> LENGTH: 9
<212> TYPE: PRT
<213> ORGANISM: Rotavirus sp.

<400> SEQUENCE: 335

Asp Pro Val Ile Asp Arg Leu Tyr Leu
1 5

<210> SEQ ID NO 336
<211> LENGTH: 9
<212> TYPE: PRT
<213> ORGANISM: Rotavirus sp.

<400> SEQUENCE: 336

Ser Pro Gly Arg Ser Phe Ser Tyr Phe
1 5

<210> SEQ ID NO 337
<211> LENGTH: 8
<212> TYPE: PRT
<213> ORGANISM: Rotavirus sp.

<400> SEQUENCE: 337

Thr Tyr Lys Asp Thr Val Gln Leu 1          5

<210> SEQ ID NO 338
<211> LENGTH: 10
<212> TYPE: PRT
<213> ORGANISM: Polio virus

<400> SEQUENCE: 338

Phe Tyr Asp Gly Phe Ser Lys Val Pro Leu
1               5                   10

<210> SEQ ID NO 339
<211> LENGTH: 9
<212> TYPE: PRT
<213> ORGANISM: Pseudorabies virus

<400> SEQUENCE: 339

Ile Ala Gly Ile Gly Ile Leu Ala Ile
1               5

<210> SEQ ID NO 340
<211> LENGTH: 9
<212> TYPE: PRT
<213> ORGANISM: SV

<400> SEQUENCE: 340

Val Glu Ala Glu Ile Ala His Gln Ile
1               5

<210> SEQ ID NO 341
<211> LENGTH: 8
<212> TYPE: PRT
<213> ORGANISM: SV

<400> SEQUENCE: 341

Ile Ile Tyr Arg Phe Leu Leu Ile
1               5

<210> SEQ ID NO 342
<211> LENGTH: 9
<212> TYPE: PRT
<213> ORGANISM: Simian Virus 40

<400> SEQUENCE: 342

Val Gly Pro Val Phe Pro Pro Gly Met
1               5

<210> SEQ ID NO 343
<211> LENGTH: 9
<212> TYPE: PRT
<213> ORGANISM: Simian Virus 40

<400> SEQUENCE: 343

Tyr Ser Gly Tyr Ile Phe Arg Asp Leu
1               5

<210> SEQ ID NO 344
<211> LENGTH: 9
<212> TYPE: PRT
<213> ORGANISM: Simian Virus 40

<400> SEQUENCE: 344

Ser Tyr Ile Gly Ser Ile Asn Asn Ile
1               5

```
<210> SEQ ID NO 345
<211> LENGTH: 12
<212> TYPE: PRT
<213> ORGANISM: Simian Virus 40

<400> SEQUENCE: 345

Glu Gly Cys Thr Pro Tyr Asp Ile Asn Gln Met Leu
 1               5                  10

<210> SEQ ID NO 346
<211> LENGTH: 9
<212> TYPE: PRT
<213> ORGANISM: Simian Virus 40

<400> SEQUENCE: 346

Phe Ala Pro Gly Asn Tyr Pro Ala Leu
 1               5

<210> SEQ ID NO 347
<211> LENGTH: 8
<212> TYPE: PRT
<213> ORGANISM: Simian Virus 40

<400> SEQUENCE: 347

Val Val Tyr Asp Phe Leu Lys Cys
 1               5

<210> SEQ ID NO 348
<211> LENGTH: 10
<212> TYPE: PRT
<213> ORGANISM: Simian Virus 40

<400> SEQUENCE: 348

Ser Ala Ile Asn Asn Tyr Ala Gln Lys Leu
 1               5                  10

<210> SEQ ID NO 349
<211> LENGTH: 9
<212> TYPE: PRT
<213> ORGANISM: Simian Virus 40

<400> SEQUENCE: 349

Cys Lys Gly Val Asn Lys Glu Tyr Leu
 1               5

<210> SEQ ID NO 350
<211> LENGTH: 9
<212> TYPE: PRT
<213> ORGANISM: Simian Virus 40

<400> SEQUENCE: 350

Gln Gly Ile Asn Asn Leu Asp Asn Leu
 1               5

<210> SEQ ID NO 351
<211> LENGTH: 9
<212> TYPE: PRT
<213> ORGANISM: Simian Virus 40

<400> SEQUENCE: 351

Asn Asn Leu Asp Asn Leu Arg Asp Tyr
 1               5

<210> SEQ ID NO 352
```

-continued

```
<211> LENGTH: 9
<212> TYPE: PRT
<213> ORGANISM: Haemophilus influenzae

<400> SEQUENCE: 352

Ser Glu Phe Leu Leu Glu Lys Arg Ile
1               5

<210> SEQ ID NO 353
<211> LENGTH: 8
<212> TYPE: PRT
<213> ORGANISM: Haemophilus influenzae

<400> SEQUENCE: 353

Arg Gly Tyr Val Tyr Gln Gly Leu
1               5

<210> SEQ ID NO 354
<211> LENGTH: 9
<212> TYPE: PRT
<213> ORGANISM: Homo Sapiens

<400> SEQUENCE: 354

Glu Ala Asp Pro Thr Gly His Ser Tyr
1               5

<210> SEQ ID NO 355
<211> LENGTH: 9
<212> TYPE: PRT
<213> ORGANISM: haemophilus influenzae

<400> SEQUENCE: 355

Val Ser Asp Gly Gly Pro Asn Leu Tyr
1               5

<210> SEQ ID NO 356
<211> LENGTH: 9
<212> TYPE: PRT
<213> ORGANISM: haemophilus influenzae

<400> SEQUENCE: 356

Cys Thr Glu Leu Lys Leu Ser Asp Tyr
1               5

<210> SEQ ID NO 357
<211> LENGTH: 9
<212> TYPE: PRT
<213> ORGANISM: Homo Sapiens

<400> SEQUENCE: 357

Glu Val Asp Pro Ile Gly His Leu Tyr
1               5

<210> SEQ ID NO 358
<211> LENGTH: 10
<212> TYPE: PRT
<213> ORGANISM: Homo Sapiens

<400> SEQUENCE: 358

Met Leu Leu Ser Val Pro Leu Leu Leu Gly
1               5                   10

<210> SEQ ID NO 359
<211> LENGTH: 9
<212> TYPE: PRT
```

```
<213> ORGANISM: Hepatitis B virus
<220> FEATURE:
<221> NAME/KEY: VARIANT
<222> LOCATION: (1)...(9)
<223> OTHER INFORMATION: Xaa = Any Amino Acid

<400> SEQUENCE: 359

Ser Thr Asx Xaa Gln Ser Gly Xaa Gln
 1               5

<210> SEQ ID NO 360
<211> LENGTH: 9
<212> TYPE: PRT
<213> ORGANISM: Homo Sapiens

<400> SEQUENCE: 360

Tyr Met Asp Gly Thr Met Ser Gln Val
 1               5

<210> SEQ ID NO 361
<211> LENGTH: 9
<212> TYPE: PRT
<213> ORGANISM: Homo sapiens immonodeficiency virus type 1

<400> SEQUENCE: 361

Ile Leu Lys Glu Pro Val His Gly Val
 1               5

<210> SEQ ID NO 362
<211> LENGTH: 10
<212> TYPE: PRT
<213> ORGANISM: Haemophilus influenzae

<400> SEQUENCE: 362

Ile Leu Gly Phe Val Phe Thr Leu Thr Val
 1               5                  10

<210> SEQ ID NO 363
<211> LENGTH: 9
<212> TYPE: PRT
<213> ORGANISM: HTLV-1

<400> SEQUENCE: 363

Leu Leu Phe Gly Tyr Pro Val Tyr Val
 1               5

<210> SEQ ID NO 364
<211> LENGTH: 10
<212> TYPE: PRT
<213> ORGANISM: Hepatitis B virus

<400> SEQUENCE: 364

Gly Leu Ser Pro Thr Val Trp Leu Ser Val
 1               5                  10

<210> SEQ ID NO 365
<211> LENGTH: 9
<212> TYPE: PRT
<213> ORGANISM: Hepatitis B virus

<400> SEQUENCE: 365

Trp Leu Ser Leu Leu Val Pro Phe Val
 1               5

<210> SEQ ID NO 366
```

```
<211> LENGTH: 10
<212> TYPE: PRT
<213> ORGANISM: Hepatitis B virus

<400> SEQUENCE: 366

Phe Leu Pro Ser Asp Phe Phe Pro Ser Val
1               5                   10

<210> SEQ ID NO 367
<211> LENGTH: 9
<212> TYPE: PRT
<213> ORGANISM: EBV

<400> SEQUENCE: 367

Cys Leu Gly Gly Leu Leu Thr Met Val
1               5

<210> SEQ ID NO 368
<211> LENGTH: 11
<212> TYPE: PRT
<213> ORGANISM: Homo Sapiens cytomegalovirus

<400> SEQUENCE: 368

Phe Leu Ala Gly Asn Ser Ala Tyr Glu Tyr Val
1               5                   10

<210> SEQ ID NO 369
<211> LENGTH: 10
<212> TYPE: PRT
<213> ORGANISM: Haemophilus influenzae

<400> SEQUENCE: 369

Lys Leu Gly Glu Phe Tyr Asn Gln Met Met
1               5                   10

<210> SEQ ID NO 370
<211> LENGTH: 10
<212> TYPE: PRT
<213> ORGANISM: Hepatitis C virus

<400> SEQUENCE: 370

Lys Leu Val Ala Leu Gly Ile Asn Ala Val
1               5                   10

<210> SEQ ID NO 371
<211> LENGTH: 9
<212> TYPE: PRT
<213> ORGANISM: Hepatitis C virus

<400> SEQUENCE: 371

Asp Leu Met Gly Tyr Ile Pro Leu Val
1               5

<210> SEQ ID NO 372
<211> LENGTH: 9
<212> TYPE: PRT
<213> ORGANISM: Homo Sapiens papillomavirus type 11

<400> SEQUENCE: 372

Arg Leu Val Thr Leu Lys Asp Ile Val
1               5

<210> SEQ ID NO 373
<211> LENGTH: 9
<212> TYPE: PRT
```

<213> ORGANISM: Homo Sapiens

<400> SEQUENCE: 373

Met Leu Leu Ala Val Leu Tyr Cys Leu
 1               5

<210> SEQ ID NO 374
<211> LENGTH: 9
<212> TYPE: PRT
<213> ORGANISM: Homo Sapiens

<400> SEQUENCE: 374

Ala Ala Gly Ile Gly Ile Leu Thr Val
 1               5

<210> SEQ ID NO 375
<211> LENGTH: 9
<212> TYPE: PRT
<213> ORGANISM: Homo Sapiens

<400> SEQUENCE: 375

Tyr Leu Glu Pro Gly Pro Val Thr Ala
 1               5

<210> SEQ ID NO 376
<211> LENGTH: 10
<212> TYPE: PRT
<213> ORGANISM: Homo Sapiens

<400> SEQUENCE: 376

Ile Leu Asp Gly Thr Ala Thr Leu Arg Leu
 1               5                   10

<210> SEQ ID NO 377
<211> LENGTH: 10
<212> TYPE: PRT
<213> ORGANISM: Homo Sapiens

<400> SEQUENCE: 377

Leu Leu Asp Gly Thr Ala Thr Leu Arg Leu
 1               5                   10

<210> SEQ ID NO 378
<211> LENGTH: 9
<212> TYPE: PRT
<213> ORGANISM: Homo Sapiens

<400> SEQUENCE: 378

Ile Thr Asp Gln Val Pro Phe Ser Val
 1               5

<210> SEQ ID NO 379
<211> LENGTH: 9
<212> TYPE: PRT
<213> ORGANISM: Homo Sapiens

<400> SEQUENCE: 379

Lys Thr Trp Gly Gln Tyr Trp Gln Val
 1               5

<210> SEQ ID NO 380
<211> LENGTH: 10
<212> TYPE: PRT
<213> ORGANISM: Homo Sapiens

```
<400> SEQUENCE: 380

Thr Ile Thr Asp Gln Val Pro Phe Ser Val
 1               5                  10

<210> SEQ ID NO 381
<211> LENGTH: 9
<212> TYPE: PRT
<213> ORGANISM: Homo Sapiens immonodeficiency virus type 1

<400> SEQUENCE: 381

Ala Phe His His Val Ala Arg Glu Leu
 1               5

<210> SEQ ID NO 382
<211> LENGTH: 9
<212> TYPE: PRT
<213> ORGANISM: Plasmodium falciparum

<400> SEQUENCE: 382

Tyr Leu Asn Lys Ile Gln Asn Ser Leu
 1               5

<210> SEQ ID NO 383
<211> LENGTH: 10
<212> TYPE: PRT
<213> ORGANISM: Plasmodium falciparum

<400> SEQUENCE: 383

Met Met Arg Lys Leu Ala Ile Leu Ser Val
 1               5                  10

<210> SEQ ID NO 384
<211> LENGTH: 10
<212> TYPE: PRT
<213> ORGANISM: haemophilus influenzae

<400> SEQUENCE: 384

Lys Ala Gly Glu Phe Tyr Asn Gln Met Met
 1               5                  10

<210> SEQ ID NO 385
<211> LENGTH: 9
<212> TYPE: PRT
<213> ORGANISM: EBV

<400> SEQUENCE: 385

Asn Ile Ala Glu Gly Leu Arg Ala Leu
 1               5

<210> SEQ ID NO 386
<211> LENGTH: 9
<212> TYPE: PRT
<213> ORGANISM: EBV

<400> SEQUENCE: 386

Asn Leu Arg Arg Gly Thr Ala Leu Ala
 1               5

<210> SEQ ID NO 387
<211> LENGTH: 9
<212> TYPE: PRT
<213> ORGANISM: EBV

<400> SEQUENCE: 387
```

```
Ala Leu Ala Ile Pro Gln Cys Arg Leu
 1               5

<210> SEQ ID NO 388
<211> LENGTH: 9
<212> TYPE: PRT
<213> ORGANISM: EBV

<400> SEQUENCE: 388

Val Leu Lys Asp Ala Ile Lys Asp Leu
 1               5

<210> SEQ ID NO 389
<211> LENGTH: 9
<212> TYPE: PRT
<213> ORGANISM: EBV

<400> SEQUENCE: 389

Phe Met Val Phe Ile Gln Thr His Ile
 1               5

<210> SEQ ID NO 390
<211> LENGTH: 9
<212> TYPE: PRT
<213> ORGANISM: EBV

<400> SEQUENCE: 390

His Leu Ile Val Asp Thr Asp Ser Leu
 1               5

<210> SEQ ID NO 391
<211> LENGTH: 9
<212> TYPE: PRT
<213> ORGANISM: EBV

<400> SEQUENCE: 391

Ser Leu Gly Asn Pro Ser Leu Ser Val
 1               5

<210> SEQ ID NO 392
<211> LENGTH: 9
<212> TYPE: PRT
<213> ORGANISM: EBV

<400> SEQUENCE: 392

Pro Leu Ala Ser Ala Met Arg Met Leu
 1               5

<210> SEQ ID NO 393
<211> LENGTH: 9
<212> TYPE: PRT
<213> ORGANISM: EBV

<400> SEQUENCE: 393

Arg Met Leu Trp Met Ala Asn Tyr Ile
 1               5

<210> SEQ ID NO 394
<211> LENGTH: 9
<212> TYPE: PRT
<213> ORGANISM: EBV

<400> SEQUENCE: 394

Met Leu Trp Met Ala Asn Tyr Ile Val
 1               5
```

<210> SEQ ID NO 395
<211> LENGTH: 9
<212> TYPE: PRT
<213> ORGANISM: EBV

<400> SEQUENCE: 395

Ile Leu Pro Gln Gly Pro Gln Thr Ala
1               5

<210> SEQ ID NO 396
<211> LENGTH: 9
<212> TYPE: PRT
<213> ORGANISM: EBV

<400> SEQUENCE: 396

Pro Leu Arg Pro Thr Ala Pro Thr Ile
1               5

<210> SEQ ID NO 397
<211> LENGTH: 9
<212> TYPE: PRT
<213> ORGANISM: EBV

<400> SEQUENCE: 397

Pro Leu Pro Pro Ala Thr Leu Thr Val
1               5

<210> SEQ ID NO 398
<211> LENGTH: 9
<212> TYPE: PRT
<213> ORGANISM: EBV

<400> SEQUENCE: 398

Arg Met His Leu Pro Val Leu His Val
1               5

<210> SEQ ID NO 399
<211> LENGTH: 9
<212> TYPE: PRT
<213> ORGANISM: EBV

<400> SEQUENCE: 399

Pro Met Pro Leu Pro Pro Ser Gln Leu
1               5

<210> SEQ ID NO 400
<211> LENGTH: 9
<212> TYPE: PRT
<213> ORGANISM: EBV

<400> SEQUENCE: 400

Gln Leu Pro Pro Pro Ala Ala Pro Ala
1               5

<210> SEQ ID NO 401
<211> LENGTH: 9
<212> TYPE: PRT
<213> ORGANISM: EBV

<400> SEQUENCE: 401

Ser Met Pro Glu Leu Ser Pro Val Leu
1               5

-continued

```
<210> SEQ ID NO 402
<211> LENGTH: 9
<212> TYPE: PRT
<213> ORGANISM: EBV

<400> SEQUENCE: 402

Asp Leu Asp Glu Ser Trp Asp Tyr Ile
1               5

<210> SEQ ID NO 403
<211> LENGTH: 9
<212> TYPE: PRT
<213> ORGANISM: EBV

<400> SEQUENCE: 403

Pro Leu Pro Cys Val Leu Trp Pro Val
1               5

<210> SEQ ID NO 404
<211> LENGTH: 9
<212> TYPE: PRT
<213> ORGANISM: EBV

<400> SEQUENCE: 404

Ser Leu Glu Glu Cys Asp Ser Glu Leu
1               5

<210> SEQ ID NO 405
<211> LENGTH: 9
<212> TYPE: PRT
<213> ORGANISM: EBV

<400> SEQUENCE: 405

Glu Ile Lys Arg Tyr Lys Asn Arg Val
1               5

<210> SEQ ID NO 406
<211> LENGTH: 9
<212> TYPE: PRT
<213> ORGANISM: EBV

<400> SEQUENCE: 406

Gln Leu Leu Gln His Tyr Arg Glu Val
1               5

<210> SEQ ID NO 407
<211> LENGTH: 9
<212> TYPE: PRT
<213> ORGANISM: EBV

<400> SEQUENCE: 407

Leu Leu Gln His Tyr Arg Glu Val Ala
1               5

<210> SEQ ID NO 408
<211> LENGTH: 9
<212> TYPE: PRT
<213> ORGANISM: EBV

<400> SEQUENCE: 408

Leu Leu Lys Gln Met Cys Pro Ser Leu
1               5

<210> SEQ ID NO 409
<211> LENGTH: 9
```

```
<212> TYPE: PRT
<213> ORGANISM: EBV

<400> SEQUENCE: 409

Ser Ile Ile Pro Arg Thr Pro Asp Val
 1               5

<210> SEQ ID NO 410
<211> LENGTH: 9
<212> TYPE: PRT
<213> ORGANISM: haemophilus influenzae

<400> SEQUENCE: 410

Ala Ile Met Asp Lys Asn Ile Ile Leu
 1               5

<210> SEQ ID NO 411
<211> LENGTH: 10
<212> TYPE: PRT
<213> ORGANISM: Haemophilus influenzae

<400> SEQUENCE: 411

Ile Met Asp Lys Asn Ile Ile Leu Lys Ala
 1               5                  10

<210> SEQ ID NO 412
<211> LENGTH: 10
<212> TYPE: PRT
<213> ORGANISM: Hepatitis C virus

<400> SEQUENCE: 412

Leu Leu Ala Leu Leu Ser Cys Leu Thr Val
 1               5                  10

<210> SEQ ID NO 413
<211> LENGTH: 8
<212> TYPE: PRT
<213> ORGANISM: Hepatitis C virus

<400> SEQUENCE: 413

Ile Leu His Thr Pro Gly Cys Val
 1               5

<210> SEQ ID NO 414
<211> LENGTH: 10
<212> TYPE: PRT
<213> ORGANISM: Hepatitis C virus

<400> SEQUENCE: 414

Gln Leu Arg Arg His Ile Asp Leu Leu Val
 1               5                  10

<210> SEQ ID NO 415
<211> LENGTH: 9
<212> TYPE: PRT
<213> ORGANISM: Hepatitis C virus

<400> SEQUENCE: 415

Asp Leu Cys Gly Ser Val Phe Leu Val
 1               5

<210> SEQ ID NO 416
<211> LENGTH: 9
<212> TYPE: PRT
<213> ORGANISM: Hepatitis C virus
```

<400> SEQUENCE: 416

Ser Met Val Gly Asn Trp Ala Lys Val
1               5

<210> SEQ ID NO 417
<211> LENGTH: 9
<212> TYPE: PRT
<213> ORGANISM: Hepatitis C virus

<400> SEQUENCE: 417

His Leu His Gln Asn Ile Val Asp Val
1               5

<210> SEQ ID NO 418
<211> LENGTH: 9
<212> TYPE: PRT
<213> ORGANISM: Hepatitis C virus

<400> SEQUENCE: 418

Phe Leu Leu Leu Ala Asp Ala Arg Val
1               5

<210> SEQ ID NO 419
<211> LENGTH: 13
<212> TYPE: PRT
<213> ORGANISM: Hepatitis C virus

<400> SEQUENCE: 419

Gly Leu Arg Asp Leu Ala Val Ala Val Glu Pro Val Val
1               5                   10

<210> SEQ ID NO 420
<211> LENGTH: 11
<212> TYPE: PRT
<213> ORGANISM: Hepatitis C virus

<400> SEQUENCE: 420

Ser Leu Leu Ala Pro Gly Ala Lys Gln Asn Val
1               5                   10

<210> SEQ ID NO 421
<211> LENGTH: 10
<212> TYPE: PRT
<213> ORGANISM: Hepatitis C virus

<400> SEQUENCE: 421

Leu Leu Ala Pro Gly Ala Lys Gln Asn Val
1               5                   10

<210> SEQ ID NO 422
<211> LENGTH: 9
<212> TYPE: PRT
<213> ORGANISM: Hepatitis B virus

<400> SEQUENCE: 422

Phe Leu Leu Ser Leu Gly Ile His Leu
1               5

<210> SEQ ID NO 423
<211> LENGTH: 9
<212> TYPE: PRT
<213> ORGANISM: Hepatitis B virus

<400> SEQUENCE: 423

Ser Leu Tyr Ala Asp Ser Pro Ser Val
1               5

<210> SEQ ID NO 424
<211> LENGTH: 9
<212> TYPE: PRT
<213> ORGANISM: Hepatitis B virus

<400> SEQUENCE: 424

Gly Leu Ser Arg Tyr Val Ala Arg Leu
1               5

<210> SEQ ID NO 425
<211> LENGTH: 9
<212> TYPE: PRT
<213> ORGANISM: Homo Sapiens

<400> SEQUENCE: 425

Lys Ile Phe Gly Ser Leu Ala Phe Leu
1               5

<210> SEQ ID NO 426
<211> LENGTH: 9
<212> TYPE: PRT
<213> ORGANISM: Homo Sapiens

<400> SEQUENCE: 426

Glu Leu Val Ser Glu Phe Ser Arg Met
1               5

<210> SEQ ID NO 427
<211> LENGTH: 9
<212> TYPE: PRT
<213> ORGANISM: Homo Sapiens immunodeficiency virus type 1

<400> SEQUENCE: 427

Lys Leu Thr Pro Leu Cys Val Thr Leu
1               5

<210> SEQ ID NO 428
<211> LENGTH: 10
<212> TYPE: PRT
<213> ORGANISM: Homo Sapiens immunodeficiency virus type 1

<400> SEQUENCE: 428

Ser Leu Leu Asn Ala Thr Asp Ile Ala Val
1               5                   10

<210> SEQ ID NO 429
<211> LENGTH: 10
<212> TYPE: PRT
<213> ORGANISM: Homo Sapiens

<400> SEQUENCE: 429

Val Leu Tyr Arg Tyr Gly Ser Phe Ser Val
1               5                   10

<210> SEQ ID NO 430
<211> LENGTH: 9
<212> TYPE: PRT
<213> ORGANISM: Homo Sapiens

<400> SEQUENCE: 430

Tyr Ile Gly Glu Val Leu Val Ser Val

```
1               5

<210> SEQ ID NO 431
<211> LENGTH: 10
<212> TYPE: PRT
<213> ORGANISM: Hepatitis C virus

<400> SEQUENCE: 431

Leu Leu Phe Asn Ile Leu Gly Gly Trp Val
1               5                   10

<210> SEQ ID NO 432
<211> LENGTH: 10
<212> TYPE: PRT
<213> ORGANISM: Hepatitis B virus

<400> SEQUENCE: 432

Leu Leu Val Pro Phe Val Gln Trp Phe Trp
1               5                   10

<210> SEQ ID NO 433
<211> LENGTH: 9
<212> TYPE: PRT
<213> ORGANISM: Hepatitis B virus

<400> SEQUENCE: 433

Ala Leu Met Pro Leu Tyr Ala Cys Ile
1               5

<210> SEQ ID NO 434
<211> LENGTH: 9
<212> TYPE: PRT
<213> ORGANISM: Hepatitis C virus

<400> SEQUENCE: 434

Tyr Leu Val Ala Tyr Gln Ala Thr Val
1               5

<210> SEQ ID NO 435
<211> LENGTH: 9
<212> TYPE: PRT
<213> ORGANISM: Homo Sapiens papillomavirus type 16

<400> SEQUENCE: 435

Thr Leu Gly Ile Val Cys Pro Ile Cys
1               5

<210> SEQ ID NO 436
<211> LENGTH: 10
<212> TYPE: PRT
<213> ORGANISM: Hepatitis C virus

<400> SEQUENCE: 436

Tyr Leu Leu Pro Arg Arg Gly Pro Arg Leu
1               5                   10

<210> SEQ ID NO 437
<211> LENGTH: 10
<212> TYPE: PRT
<213> ORGANISM: Hepatitis B virus

<400> SEQUENCE: 437

Leu Leu Pro Ile Phe Phe Cys Leu Trp Val
1               5                   10
```

```
<210> SEQ ID NO 438
<211> LENGTH: 9
<212> TYPE: PRT
<213> ORGANISM: Hepatitis B virus

<400> SEQUENCE: 438

Tyr Met Asp Asp Val Val Leu Gly Ala
1               5

<210> SEQ ID NO 439
<211> LENGTH: 9
<212> TYPE: PRT
<213> ORGANISM: Homo Sapiens papillomavirus type 16

<400> SEQUENCE: 439

Gly Thr Leu Gly Ile Val Cys Pro Ile
1               5

<210> SEQ ID NO 440
<211> LENGTH: 10
<212> TYPE: PRT
<213> ORGANISM: Hepatitis C virus

<400> SEQUENCE: 440

Leu Leu Ala Leu Leu Ser Cys Leu Thr Ile
1               5                   10

<210> SEQ ID NO 441
<211> LENGTH: 9
<212> TYPE: PRT
<213> ORGANISM: Homo Sapiens papillomavirus type 16

<400> SEQUENCE: 441

Met Leu Asp Leu Gln Pro Glu Thr Thr
1               5

<210> SEQ ID NO 442
<211> LENGTH: 9
<212> TYPE: PRT
<213> ORGANISM: Hepatitis C virus

<400> SEQUENCE: 442

Ser Leu Met Ala Phe Thr Ala Ala Val
1               5

<210> SEQ ID NO 443
<211> LENGTH: 9
<212> TYPE: PRT
<213> ORGANISM: Hepatitis C virus

<400> SEQUENCE: 443

Cys Ile Asn Gly Val Cys Trp Thr Val
1               5

<210> SEQ ID NO 444
<211> LENGTH: 10
<212> TYPE: PRT
<213> ORGANISM: Homo Sapiens

<400> SEQUENCE: 444

Val Met Asn Ile Leu Leu Gln Tyr Val Val
1               5                   10

<210> SEQ ID NO 445
```

```
<211> LENGTH: 9
<212> TYPE: PRT
<213> ORGANISM: Homo Sapiens

<400> SEQUENCE: 445

Ile Leu Thr Val Ile Leu Gly Val Leu
 1               5

<210> SEQ ID NO 446
<211> LENGTH: 9
<212> TYPE: PRT
<213> ORGANISM: Homo Sapiens

<400> SEQUENCE: 446

Phe Leu Trp Gly Pro Arg Ala Leu Val
 1               5

<210> SEQ ID NO 447
<211> LENGTH: 9
<212> TYPE: PRT
<213> ORGANISM: Hepatitis C virus

<400> SEQUENCE: 447

Leu Leu Cys Pro Ala Gly His Ala Val
 1               5

<210> SEQ ID NO 448
<211> LENGTH: 9
<212> TYPE: PRT
<213> ORGANISM: Hepatitis C virus

<400> SEQUENCE: 448

Ile Leu Asp Ser Phe Asp Pro Leu Val
 1               5

<210> SEQ ID NO 449
<211> LENGTH: 9
<212> TYPE: PRT
<213> ORGANISM: Hepatitis B virus

<400> SEQUENCE: 449

Leu Leu Leu Cys Leu Ile Phe Leu Leu
 1               5

<210> SEQ ID NO 450
<211> LENGTH: 10
<212> TYPE: PRT
<213> ORGANISM: Hepatitis B virus

<400> SEQUENCE: 450

Leu Ile Asp Tyr Gln Gly Met Leu Pro Val
 1               5                  10

<210> SEQ ID NO 451
<211> LENGTH: 10
<212> TYPE: PRT
<213> ORGANISM: Hepatitis B virus

<400> SEQUENCE: 451

Ser Ile Val Ser Pro Phe Ile Pro Leu Leu
 1               5                  10

<210> SEQ ID NO 452
<211> LENGTH: 9
<212> TYPE: PRT
```

```
<213> ORGANISM: Hepatitis B virus

<400> SEQUENCE: 452

Phe Leu Leu Thr Arg Ile Leu Thr Ile
 1               5

<210> SEQ ID NO 453
<211> LENGTH: 9
<212> TYPE: PRT
<213> ORGANISM: Plasmodium falciparum

<400> SEQUENCE: 453

His Leu Gly Asn Val Lys Tyr Leu Val
 1               5

<210> SEQ ID NO 454
<211> LENGTH: 9
<212> TYPE: PRT
<213> ORGANISM: Plasmodium falciparum

<400> SEQUENCE: 454

Gly Ile Ala Gly Gly Leu Ala Leu Leu
 1               5

<210> SEQ ID NO 455
<211> LENGTH: 9
<212> TYPE: PRT
<213> ORGANISM: Hepatitis C virus

<400> SEQUENCE: 455

Ile Leu Ala Gly Tyr Gly Ala Gly Val
 1               5

<210> SEQ ID NO 456
<211> LENGTH: 9
<212> TYPE: PRT
<213> ORGANISM: Hepatitis C virus

<400> SEQUENCE: 456

Gly Leu Gln Asp Cys Thr Met Leu Val
 1               5

<210> SEQ ID NO 457
<211> LENGTH: 10
<212> TYPE: PRT
<213> ORGANISM: Hepatitis C virus

<400> SEQUENCE: 457

Thr Gly Ala Pro Val Thr Tyr Ser Thr Tyr
 1               5                  10

<210> SEQ ID NO 458
<211> LENGTH: 9
<212> TYPE: PRT
<213> ORGANISM: Homo Sapiens immunodeficiency virus type 1

<400> SEQUENCE: 458

Val Ile Tyr Gln Tyr Met Asp Asp Leu
 1               5

<210> SEQ ID NO 459
<211> LENGTH: 10
<212> TYPE: PRT
<213> ORGANISM: Homo Sapiens
```

```
<400> SEQUENCE: 459

Val Leu Pro Asp Val Phe Ile Arg Cys Val
 1               5                  10

<210> SEQ ID NO 460
<211> LENGTH: 9
<212> TYPE: PRT
<213> ORGANISM: Homo Sapiens

<400> SEQUENCE: 460

Val Leu Pro Asp Val Phe Ile Arg Cys
 1               5

<210> SEQ ID NO 461
<211> LENGTH: 9
<212> TYPE: PRT
<213> ORGANISM: Homo Sapiens

<400> SEQUENCE: 461

Ala Val Gly Ile Gly Ile Ala Val Val
 1               5

<210> SEQ ID NO 462
<211> LENGTH: 9
<212> TYPE: PRT
<213> ORGANISM: Homo Sapiens

<400> SEQUENCE: 462

Leu Val Val Leu Gly Leu Leu Ala Val
 1               5

<210> SEQ ID NO 463
<211> LENGTH: 9
<212> TYPE: PRT
<213> ORGANISM: Homo Sapiens

<400> SEQUENCE: 463

Ala Leu Gly Leu Gly Leu Leu Pro Val
 1               5

<210> SEQ ID NO 464
<211> LENGTH: 9
<212> TYPE: PRT
<213> ORGANISM: HSV-2

<400> SEQUENCE: 464

Gly Ala Gly Ile Gly Val Ala Val Leu
 1               5

<210> SEQ ID NO 465
<211> LENGTH: 9
<212> TYPE: PRT
<213> ORGANISM: Pseudorabies virus

<400> SEQUENCE: 465

Ile Ala Gly Ile Gly Ile Leu Ala Ile
 1               5

<210> SEQ ID NO 466
<211> LENGTH: 9
<212> TYPE: PRT
<213> ORGANISM: Adenovirus 3

<400> SEQUENCE: 466
```

```
Leu Ile Val Ile Gly Ile Leu Ile Leu
 1               5
```

<210> SEQ ID NO 467
<211> LENGTH: 9
<212> TYPE: PRT
<213> ORGANISM: S. lincolnensis

<400> SEQUENCE: 467

```
Leu Ala Gly Ile Gly Leu Ile Ala Ala
 1               5
```

<210> SEQ ID NO 468
<211> LENGTH: 9
<212> TYPE: PRT
<213> ORGANISM: Yeast

<400> SEQUENCE: 468

```
Val Asp Gly Ile Gly Ile Leu Thr Ile
 1               5
```

<210> SEQ ID NO 469
<211> LENGTH: 9
<212> TYPE: PRT
<213> ORGANISM: B. polymyxa

<400> SEQUENCE: 469

```
Gly Ala Gly Ile Gly Val Leu Thr Ala
 1               5
```

<210> SEQ ID NO 470
<211> LENGTH: 9
<212> TYPE: PRT
<213> ORGANISM: Escherichia coli

<400> SEQUENCE: 470

```
Ala Ala Gly Ile Gly Ile Ile Gln Ile
 1               5
```

<210> SEQ ID NO 471
<211> LENGTH: 9
<212> TYPE: PRT
<213> ORGANISM: Escherichia coli

<400> SEQUENCE: 471

```
Gln Ala Gly Ile Gly Ile Leu Leu Ala
 1               5
```

<210> SEQ ID NO 472
<211> LENGTH: 11
<212> TYPE: PRT
<213> ORGANISM: Homo Sapiens

<400> SEQUENCE: 472

```
Lys Ala Arg Asp Pro His Ser Gly His Phe Val
 1               5                  10
```

<210> SEQ ID NO 473
<211> LENGTH: 11
<212> TYPE: PRT
<213> ORGANISM: Homo Sapiens

<400> SEQUENCE: 473

```
Lys Ala Cys Asp Pro His Ser Gly His Phe Val
 1               5                  10
```

<210> SEQ ID NO 474
<211> LENGTH: 10
<212> TYPE: PRT
<213> ORGANISM: Homo Sapiens

<400> SEQUENCE: 474

Ala Cys Asp Pro His Ser Gly His Phe Val
 1               5                  10

<210> SEQ ID NO 475
<211> LENGTH: 9
<212> TYPE: PRT
<213> ORGANISM: Homo Sapiens immunodeficiency virus type 1

<400> SEQUENCE: 475

Ser Leu Tyr Asn Thr Val Ala Thr Leu
 1               5

<210> SEQ ID NO 476
<211> LENGTH: 9
<212> TYPE: PRT
<213> ORGANISM: Homo Sapiens

<400> SEQUENCE: 476

Glu Leu Val Ser Glu Phe Ser Arg Val
 1               5

<210> SEQ ID NO 477
<211> LENGTH: 10
<212> TYPE: PRT
<213> ORGANISM: Homo Sapiens immunodeficiency virus type 1

<400> SEQUENCE: 477

Arg Gly Pro Gly Arg Ala Phe Val Thr Ile
 1               5                  10

<210> SEQ ID NO 478
<211> LENGTH: 9
<212> TYPE: PRT
<213> ORGANISM: Hepatitis C virus

<400> SEQUENCE: 478

His Met Trp Asn Phe Ile Ser Gly Ile
 1               5

<210> SEQ ID NO 479
<211> LENGTH: 10
<212> TYPE: PRT
<213> ORGANISM: Homo Sapiens cytomegalovirus

<400> SEQUENCE: 479

Asn Leu Val Pro Met Val Ala Thr Val Gln
 1               5                  10

<210> SEQ ID NO 480
<211> LENGTH: 9
<212> TYPE: PRT
<213> ORGANISM: Homo Sapiens papillomavirus type 6b

<400> SEQUENCE: 480

Gly Leu His Cys Tyr Glu Gln Leu Val
 1               5

```
<210> SEQ ID NO 481
<211> LENGTH: 9
<212> TYPE: PRT
<213> ORGANISM: Homo Sapiens papillomavirus type 6b

<400> SEQUENCE: 481

Pro Leu Lys Gln His Phe Gln Ile Val
 1               5

<210> SEQ ID NO 482
<211> LENGTH: 10
<212> TYPE: PRT
<213> ORGANISM: EBV

<400> SEQUENCE: 482

Leu Leu Asp Phe Val Arg Phe Met Gly Val
 1               5                  10

<210> SEQ ID NO 483
<211> LENGTH: 9
<212> TYPE: PRT
<213> ORGANISM: Haemophilus influenzae

<400> SEQUENCE: 483

Ala Ile Met Glu Lys Asn Ile Met Leu
 1               5

<210> SEQ ID NO 484
<211> LENGTH: 9
<212> TYPE: PRT
<213> ORGANISM: Plasmodium falciparum

<400> SEQUENCE: 484

Tyr Leu Lys Thr Ile Gln Asn Ser Leu
 1               5

<210> SEQ ID NO 485
<211> LENGTH: 9
<212> TYPE: PRT
<213> ORGANISM: Plasmodium falciparum

<400> SEQUENCE: 485

Tyr Leu Asn Lys Ile Gln Asn Ser Leu
 1               5

<210> SEQ ID NO 486
<211> LENGTH: 10
<212> TYPE: PRT
<213> ORGANISM: Homo sapiens papillomaviurs type 16

<400> SEQUENCE: 486

Tyr Met Leu Asp Leu Gln Pro Glu Thr Thr
 1               5                  10

<210> SEQ ID NO 487
<211> LENGTH: 9
<212> TYPE: PRT
<213> ORGANISM: Homo sampiens papillomavirus type 16

<400> SEQUENCE: 487

Leu Leu Met Gly Thr Leu Gly Ile Val
 1               5

<210> SEQ ID NO 488
<211> LENGTH: 8
```

-continued

```
<212> TYPE: PRT
<213> ORGANISM: Homo sampiens papillomavirus type 16

<400> SEQUENCE: 488

Thr Leu Gly Ile Val Cys Pro Ile
 1               5

<210> SEQ ID NO 489
<211> LENGTH: 9
<212> TYPE: PRT
<213> ORGANISM: Homo sapiens immunodeficiency virus type 1

<400> SEQUENCE: 489

Thr Leu Thr Ser Cys Asn Thr Ser Val
 1               5

<210> SEQ ID NO 490
<211> LENGTH: 9
<212> TYPE: PRT
<213> ORGANISM: Homo Sapiens papillomavirus type 16

<400> SEQUENCE: 490

Lys Leu Pro Gln Leu Cys Thr Glu Leu
 1               5

<210> SEQ ID NO 491
<211> LENGTH: 9
<212> TYPE: PRT
<213> ORGANISM: Homo Sapiens papillomavirus type 16

<400> SEQUENCE: 491

Thr Ile His Asp Ile Ile Leu Glu Cys
 1               5

<210> SEQ ID NO 492
<211> LENGTH: 9
<212> TYPE: PRT
<213> ORGANISM: Homo Sapiens papillomavirus type 16

<400> SEQUENCE: 492

Leu Gly Ile Val Cys Pro Ile Cys Ser
 1               5

<210> SEQ ID NO 493
<211> LENGTH: 9
<212> TYPE: PRT
<213> ORGANISM: Homo Sapiens

<400> SEQUENCE: 493

Val Ile Leu Gly Val Leu Leu Leu Ile
 1               5

<210> SEQ ID NO 494
<211> LENGTH: 9
<212> TYPE: PRT
<213> ORGANISM: Axial seamount polynoid polychaete

<400> SEQUENCE: 494

Ala Leu Met Asp Lys Ser Leu His Val
 1               5

<210> SEQ ID NO 495
<211> LENGTH: 9
<212> TYPE: PRT
<213> ORGANISM: Homo Sapiens
```

-continued

```
<400> SEQUENCE: 495

Gly Ile Leu Thr Val Ile Leu Gly Val
1               5

<210> SEQ ID NO 496
<211> LENGTH: 9
<212> TYPE: PRT
<213> ORGANISM: Plasmodium falciparum

<400> SEQUENCE: 496

Met Ile Asn Ala Tyr Leu Asp Lys Leu
1               5

<210> SEQ ID NO 497
<211> LENGTH: 9
<212> TYPE: PRT
<213> ORGANISM: Homo Sapiens

<400> SEQUENCE: 497

Ala Ala Gly Ile Gly Ile Leu Thr Val
1               5

<210> SEQ ID NO 498
<211> LENGTH: 10
<212> TYPE: PRT
<213> ORGANISM: Homo Sapiens

<400> SEQUENCE: 498

Phe Leu Pro Ser Asp Phe Phe Pro Ser Val
1               5                   10

<210> SEQ ID NO 499
<211> LENGTH: 9
<212> TYPE: PRT
<213> ORGANISM: EBV

<400> SEQUENCE: 499

Ser Val Arg Asp Arg Leu Ala Arg Leu
1               5

<210> SEQ ID NO 500
<211> LENGTH: 9
<212> TYPE: PRT
<213> ORGANISM: Homo Sapiens

<400> SEQUENCE: 500

Phe Ala Tyr Asp Gly Lys Asp Tyr Ile
1               5

<210> SEQ ID NO 501
<211> LENGTH: 9
<212> TYPE: PRT
<213> ORGANISM: Homo Sapiens

<400> SEQUENCE: 501

Ala Leu Leu Ala Val Gly Ala Thr Lys
1               5

<210> SEQ ID NO 502
<211> LENGTH: 11
<212> TYPE: PRT
<213> ORGANISM: Homo Sapiens immunodeficiency virus type 1

<400> SEQUENCE: 502
```

Arg Leu Arg Asp Leu Leu Ile Val Thr Arg
1               5                   10

<210> SEQ ID NO 503
<211> LENGTH: 10
<212> TYPE: PRT
<213> ORGANISM: Homo Sapiens immunodeficiency virus type 1

<400> SEQUENCE: 503

Gln Val Pro Leu Arg Pro Met Thr Tyr Lys
1               5                   10

<210> SEQ ID NO 504
<211> LENGTH: 10
<212> TYPE: PRT
<213> ORGANISM: Homo Sapiens immunodeficiency virus type 1

<400> SEQUENCE: 504

Thr Val Tyr Tyr Gly Val Pro Val Trp Lys
1               5                   10

<210> SEQ ID NO 505
<211> LENGTH: 9
<212> TYPE: PRT
<213> ORGANISM: Homo Sapiens immunodeficiency virus type 1

<400> SEQUENCE: 505

Arg Leu Arg Pro Gly Gly Lys Lys Lys
1               5

<210> SEQ ID NO 506
<211> LENGTH: 9
<212> TYPE: PRT
<213> ORGANISM: haemophilus influenzae

<400> SEQUENCE: 506

Ile Leu Arg Gly Ser Val Ala His Lys
1               5

<210> SEQ ID NO 507
<211> LENGTH: 9
<212> TYPE: PRT
<213> ORGANISM: EBV

<400> SEQUENCE: 507

Arg Leu Arg Ala Glu Ala Gly Val Lys
1               5

<210> SEQ ID NO 508
<211> LENGTH: 9
<212> TYPE: PRT
<213> ORGANISM: Homo Sapiens immunodeficiency virus type 1

<400> SEQUENCE: 508

Val Tyr Tyr Gly Val Pro Val Trp Lys
1               5

<210> SEQ ID NO 509
<211> LENGTH: 9
<212> TYPE: PRT
<213> ORGANISM: Hepatitis C virus

<400> SEQUENCE: 509

Arg Val Cys Glu Lys Met Ala Leu Tyr

```
<210> SEQ ID NO 510
<211> LENGTH: 9
<212> TYPE: PRT
<213> ORGANISM: Homo Sapiens

<400> SEQUENCE: 510

Lys Ile Phe Ser Glu Val Thr Leu Lys
 1               5

<210> SEQ ID NO 511
<211> LENGTH: 9
<212> TYPE: PRT
<213> ORGANISM: Hepatitis B virus

<400> SEQUENCE: 511

Tyr Val Asn Val Asn Met Gly Leu Lys
 1               5

<210> SEQ ID NO 512
<211> LENGTH: 9
<212> TYPE: PRT
<213> ORGANISM: EBV

<400> SEQUENCE: 512

Ile Val Thr Asp Phe Ser Val Ile Lys
 1               5

<210> SEQ ID NO 513
<211> LENGTH: 8
<212> TYPE: PRT
<213> ORGANISM: Homo Sapiens

<400> SEQUENCE: 513

Glu Leu Asn Glu Ala Glu Leu Lys
 1               5

<210> SEQ ID NO 514
<211> LENGTH: 9
<212> TYPE: PRT
<213> ORGANISM: Homo Sapiens immunodeficiency virus type 1

<400> SEQUENCE: 514

Val Pro Leu Arg Pro Met Thr Tyr Lys
 1               5

<210> SEQ ID NO 515
<211> LENGTH: 9
<212> TYPE: PRT
<213> ORGANISM: Homo Sapiens immunodeficiency virus type 1

<400> SEQUENCE: 515

Ala Ile Phe Gln Ser Ser Met Thr Lys
 1               5

<210> SEQ ID NO 516
<211> LENGTH: 10
<212> TYPE: PRT
<213> ORGANISM: Homo Sapiens immunodeficiency virus type 1

<400> SEQUENCE: 516

Gln Val Pro Leu Arg Pro Met Thr Tyr Lys
 1               5                  10
```

```
<210> SEQ ID NO 517
<211> LENGTH: 8
<212> TYPE: PRT
<213> ORGANISM: Hepatitis C virus

<400> SEQUENCE: 517

Thr Ile Asn Tyr Thr Ile Phe Lys
 1               5

<210> SEQ ID NO 518
<211> LENGTH: 12
<212> TYPE: PRT
<213> ORGANISM: Homo Sapiens immunodeficiency virus type 1

<400> SEQUENCE: 518

Ala Ala Val Asp Leu Ser His Phe Leu Lys Glu Lys
 1               5                  10

<210> SEQ ID NO 519
<211> LENGTH: 12
<212> TYPE: PRT
<213> ORGANISM: Homo Sapiens immunodeficiency virus type 1

<400> SEQUENCE: 519

Ala Cys Gln Gly Val Gly Gly Pro Gly His Lys
 1               5                  10

<210> SEQ ID NO 520
<211> LENGTH: 9
<212> TYPE: PRT
<213> ORGANISM: Homo Sapiens

<400> SEQUENCE: 520

Ser Tyr Leu Asp Ser Gly Ile His Phe
 1               5

<210> SEQ ID NO 521
<211> LENGTH: 9
<212> TYPE: PRT
<213> ORGANISM: Homo Sapiens immunodeficiency virus type 1

<400> SEQUENCE: 521

Arg Tyr Leu Lys Asp Gln Gln Leu Leu
 1               5

<210> SEQ ID NO 522
<211> LENGTH: 9
<212> TYPE: PRT
<213> ORGANISM: Homo Sapiens

<400> SEQUENCE: 522

Ala Tyr Gly Leu Asp Phe Tyr Ile Leu
 1               5

<210> SEQ ID NO 523
<211> LENGTH: 10
<212> TYPE: PRT
<213> ORGANISM: Homo Sapiens

<400> SEQUENCE: 523

Ala Phe Leu Pro Trp His Arg Leu Phe Leu
 1               5                  10

<210> SEQ ID NO 524
```

```
<211> LENGTH: 9
<212> TYPE: PRT
<213> ORGANISM: Homo Sapiens

<400> SEQUENCE: 524

Ala Phe Leu Pro Trp His Arg Leu Phe
 1               5

<210> SEQ ID NO 525
<211> LENGTH: 8
<212> TYPE: PRT
<213> ORGANISM: EBV

<400> SEQUENCE: 525

Arg Tyr Ser Ile Phe Phe Asp Tyr
 1               5

<210> SEQ ID NO 526
<211> LENGTH: 10
<212> TYPE: PRT
<213> ORGANISM: Homo Sapiens immunodeficiency virus type 1

<400> SEQUENCE: 526

Glu Thr Ile Asn Glu Glu Ala Ala Glu Trp
 1               5                  10

<210> SEQ ID NO 527
<211> LENGTH: 11
<212> TYPE: PRT
<213> ORGANISM: Hepatitis B virus

<400> SEQUENCE: 527

Ser Thr Leu Pro Glu Thr Thr Val Val Arg Arg
 1               5                  10

<210> SEQ ID NO 528
<211> LENGTH: 9
<212> TYPE: PRT
<213> ORGANISM: Homo Sapiens

<400> SEQUENCE: 528

Met Ser Leu Gln Arg Gln Phe Leu Arg
 1               5

<210> SEQ ID NO 529
<211> LENGTH: 9
<212> TYPE: PRT
<213> ORGANISM: Homo Sapiens

<400> SEQUENCE: 529

Leu Leu Pro Gly Gly Arg Pro Tyr Arg
 1               5

<210> SEQ ID NO 530
<211> LENGTH: 9
<212> TYPE: PRT
<213> ORGANISM: Homo Sapiens immunodeficiency virus type 1

<400> SEQUENCE: 530

Ile Val Gly Leu Asn Lys Ile Val Arg
 1               5

<210> SEQ ID NO 531
<211> LENGTH: 9
<212> TYPE: PRT
```

```
<213> ORGANISM: Homo Sapiens

<400> SEQUENCE: 531

Ala Ala Gly Ile Gly Ile Leu Thr Val
 1               5

<210> SEQ ID NO 532
<211> LENGTH: 9
<212> TYPE: PRT
<213> ORGANISM: Homo Sapiens

<400> SEQUENCE: 532

Glu Val Asp Pro Ala Ser Asn Thr Tyr
 1               5

<210> SEQ ID NO 533
<211> LENGTH: 9
<212> TYPE: PRT
<213> ORGANISM: Homo Sapiens

<400> SEQUENCE: 533

Glu Val Asp Pro Thr Ser Asn Thr Tyr
 1               5

<210> SEQ ID NO 534
<211> LENGTH: 9
<212> TYPE: PRT
<213> ORGANISM: Homo Sapiens

<400> SEQUENCE: 534

Glu Ala Asp Pro Thr Ser Asn Thr Tyr
 1               5

<210> SEQ ID NO 535
<211> LENGTH: 9
<212> TYPE: PRT
<213> ORGANISM: Homo Sapiens

<400> SEQUENCE: 535

Glu Val Asp Pro Ile Gly His Val Tyr
 1               5

<210> SEQ ID NO 536
<211> LENGTH: 11
<212> TYPE: PRT
<213> ORGANISM: Homo Sapiens

<400> SEQUENCE: 536

Met Leu Leu Ala Val Leu Leu Tyr Cys Leu Leu
 1               5                  10

<210> SEQ ID NO 537
<211> LENGTH: 9
<212> TYPE: PRT
<213> ORGANISM: Homo Sapiens

<400> SEQUENCE: 537

Met Leu Leu Ala Val Leu Tyr Cys Leu
 1               5

<210> SEQ ID NO 538
<211> LENGTH: 10
<212> TYPE: PRT
<213> ORGANISM: Homo Sapiens
```

```
<400> SEQUENCE: 538

Ser Glu Ile Trp Arg Asp Ile Asp Phe Ala
1               5                   10

<210> SEQ ID NO 539
<211> LENGTH: 9
<212> TYPE: PRT
<213> ORGANISM: Homo Sapiens

<400> SEQUENCE: 539

Ser Glu Ile Trp Arg Asp Ile Asp Phe
1               5

<210> SEQ ID NO 540
<211> LENGTH: 9
<212> TYPE: PRT
<213> ORGANISM: Homo Sapiens
<220> FEATURE:
<221> NAME/KEY: VARIANT
<222> LOCATION: (1)...(9)
<223> OTHER INFORMATION: Xaa = Any Amino Acid

<400> SEQUENCE: 540

Xaa Glu Ile Trp Arg Asp Ile Asp Phe
1               5

<210> SEQ ID NO 541
<211> LENGTH: 11
<212> TYPE: PRT
<213> ORGANISM: Homo Sapiens

<400> SEQUENCE: 541

Ser Thr Leu Val Glu Val Thr Leu Gly Glu Val
1               5                   10

<210> SEQ ID NO 542
<211> LENGTH: 9
<212> TYPE: PRT
<213> ORGANISM: Homo Sapiens

<400> SEQUENCE: 542

Leu Val Glu Val Thr Leu Gly Glu Val
1               5

<210> SEQ ID NO 543
<211> LENGTH: 10
<212> TYPE: PRT
<213> ORGANISM: Homo Sapiens

<400> SEQUENCE: 543

Val Ile Phe Ser Lys Ala Ser Glu Tyr Leu
1               5                   10

<210> SEQ ID NO 544
<211> LENGTH: 9
<212> TYPE: PRT
<213> ORGANISM: Homo Sapiens

<400> SEQUENCE: 544

Ile Ile Val Leu Ala Ile Ile Ala Ile
1               5

<210> SEQ ID NO 545
<211> LENGTH: 11
<212> TYPE: PRT
```

```
<213> ORGANISM: Homo Sapiens

<400> SEQUENCE: 545

Lys Ile Trp Glu Glu Leu Ser Met Leu Glu Val
 1               5                  10

<210> SEQ ID NO 546
<211> LENGTH: 9
<212> TYPE: PRT
<213> ORGANISM: Homo Sapiens

<400> SEQUENCE: 546

Leu Ile Glu Thr Ser Tyr Val Lys Val
 1               5

<210> SEQ ID NO 547
<211> LENGTH: 9
<212> TYPE: PRT
<213> ORGANISM: Homo Sapiens

<400> SEQUENCE: 547

Phe Leu Trp Gly Pro Arg Ala Leu Val
 1               5

<210> SEQ ID NO 548
<211> LENGTH: 10
<212> TYPE: PRT
<213> ORGANISM: Homo Sapiens

<400> SEQUENCE: 548

Thr Leu Val Glu Val Thr Leu Gly Glu Val
 1               5                  10

<210> SEQ ID NO 549
<211> LENGTH: 10
<212> TYPE: PRT
<213> ORGANISM: Homo Sapiens

<400> SEQUENCE: 549

Ala Leu Val Glu Thr Ser Tyr Val Lys Val
 1               5                  10

<210> SEQ ID NO 550
<211> LENGTH: 9
<212> TYPE: PRT
<213> ORGANISM: Homo Sapiens

<400> SEQUENCE: 550

Lys Ile Trp Glu Glu Leu Ser Val Leu
 1               5

<210> SEQ ID NO 551
<211> LENGTH: 9
<212> TYPE: PRT
<213> ORGANISM: Homo Sapiens

<400> SEQUENCE: 551

Glu Val Asp Pro Ile Gly His Leu Tyr
 1               5

<210> SEQ ID NO 552
<211> LENGTH: 9
<212> TYPE: PRT
<213> ORGANISM: Homo Sapiens
<220> FEATURE:
```

```
<221> NAME/KEY: VARIANT
<222> LOCATION: (1)...(9)
<223> OTHER INFORMATION: Xaa = Any Amino Acid

<400> SEQUENCE: 552

Glu Xaa Asp Xaa Xaa Xaa Xaa Xaa Tyr
 1               5

<210> SEQ ID NO 553
<211> LENGTH: 9
<212> TYPE: PRT
<213> ORGANISM: Homo Sapiens

<400> SEQUENCE: 553

Glu Ala Asp Pro Thr Gly His Ser Tyr
 1               5

<210> SEQ ID NO 554
<211> LENGTH: 9
<212> TYPE: PRT
<213> ORGANISM: Homo Sapiens
<220> FEATURE:
<221> NAME/KEY: VARIANT
<222> LOCATION: (1)...(9)
<223> OTHER INFORMATION: Xaa = Any Amino Acid

<400> SEQUENCE: 554

Glu Ala Asp Xaa Xaa Xaa Xaa Xaa Tyr
 1               5

<210> SEQ ID NO 555
<211> LENGTH: 9
<212> TYPE: PRT
<213> ORGANISM: Homo Sapiens
<220> FEATURE:
<221> NAME/KEY: VARIANT
<222> LOCATION: (1)...(9)
<223> OTHER INFORMATION: Xaa = Any Amino Acid

<400> SEQUENCE: 555

Glu Ala Asp Pro Xaa Xaa Xaa Xaa Tyr
 1               5

<210> SEQ ID NO 556
<211> LENGTH: 9
<212> TYPE: PRT
<213> ORGANISM: Homo Sapiens
<220> FEATURE:
<221> NAME/KEY: VARIANT
<222> LOCATION: (1)...(9)
<223> OTHER INFORMATION: Xaa = Any Amino Acid

<400> SEQUENCE: 556

Glu Ala Asp Pro Ile Xaa Xaa Xaa Tyr
 1               5

<210> SEQ ID NO 557
<211> LENGTH: 9
<212> TYPE: PRT
<213> ORGANISM: Homo Sapiens
<220> FEATURE:
<221> NAME/KEY: VARIANT
<222> LOCATION: (1)...(9)
<223> OTHER INFORMATION: Xaa = Any Amino Acid

<400> SEQUENCE: 557

Glu Ala Asp Pro Ile Gly Xaa Xaa Tyr
 1               5
```

<210> SEQ ID NO 558
<211> LENGTH: 9
<212> TYPE: PRT
<213> ORGANISM: Homo Sapiens
<220> FEATURE:
<221> NAME/KEY: VARIANT
<222> LOCATION: (1)...(9)
<223> OTHER INFORMATION: Xaa = Any Amino Acid

<400> SEQUENCE: 558

Glu Ala Asp Pro Ile Gly His Xaa Tyr
 1               5

<210> SEQ ID NO 559
<211> LENGTH: 9
<212> TYPE: PRT
<213> ORGANISM: Homo Sapiens

<400> SEQUENCE: 559

Glu Ala Asp Pro Ile Gly His Leu Tyr
 1               5

<210> SEQ ID NO 560
<211> LENGTH: 16
<212> TYPE: PRT
<213> ORGANISM: Homo Sapiens

<400> SEQUENCE: 560

Glu Leu His Ser Ala Tyr Gly Glu Pro Arg Lys Leu Leu Thr Gln Asp
 1               5                  10                  15

<210> SEQ ID NO 561
<211> LENGTH: 12
<212> TYPE: PRT
<213> ORGANISM: Homo Sapiens

<400> SEQUENCE: 561

Glu His Ser Ala Tyr Gly Glu Pro Arg Lys Leu Leu
 1               5                  10

<210> SEQ ID NO 562
<211> LENGTH: 9
<212> TYPE: PRT
<213> ORGANISM: Homo Sapiens

<400> SEQUENCE: 562

Ser Ala Tyr Gly Glu Pro Arg Lys Leu
 1               5

<210> SEQ ID NO 563
<211> LENGTH: 9
<212> TYPE: PRT
<213> ORGANISM: Homo Sapiens

<400> SEQUENCE: 563

Glu Ala Asp Pro Thr Gly His Ser Tyr
 1               5

<210> SEQ ID NO 564
<211> LENGTH: 16
<212> TYPE: PRT
<213> ORGANISM: Homo Sapiens

<400> SEQUENCE: 564

-continued

```
Met Ala Ala Arg Ala Val Phe Leu Ala Leu Ser Ala Gln Leu Leu Gln
1               5                   10                  15

<210> SEQ ID NO 565
<211> LENGTH: 16
<212> TYPE: PRT
<213> ORGANISM: Homo Sapiens

<400> SEQUENCE: 565

Met Ala Ala Arg Ala Val Phe Leu Ala Leu Ser Ala Gln Leu Leu Gln
1               5                   10                  15

<210> SEQ ID NO 566
<211> LENGTH: 9
<212> TYPE: PRT
<213> ORGANISM: Homo Sapiens

<400> SEQUENCE: 566

Ala Ala Arg Ala Val Phe Leu Ala Leu
1               5

<210> SEQ ID NO 567
<211> LENGTH: 8
<212> TYPE: PRT
<213> ORGANISM: Homo Sapiens

<400> SEQUENCE: 567

Tyr Arg Pro Arg Pro Arg Arg Tyr
1               5

<210> SEQ ID NO 568
<211> LENGTH: 9
<212> TYPE: PRT
<213> ORGANISM: Homo Sapiens immunodeficiency virus type 1

<400> SEQUENCE: 568

Asp Leu Asn Thr Met Leu Asn Thr Val
1               5

<210> SEQ ID NO 569
<211> LENGTH: 9
<212> TYPE: PRT
<213> ORGANISM: LCKV

<400> SEQUENCE: 569

Lys Ala Val Tyr Asn Phe Ala Thr Cys
1               5
```

METHOD OF INDUCING A CTL RESPONSE

CROSS REFERENCE

This application is a continuation-in-part of U.S. patent application Ser. No. 09/380,534, filed Sep. 1, 1999, which was based on PCT Application No. PCT/US98/14289, filed Jul. 10, 1998, which claimed priority from U.S. patent application Ser. No. 08/988,320, filed Dec. 10, 1997 now abandoned, and from Canadian Patent Application No. 2,209,815, filed Jul. 10, 1997, all of which are hereby incorporated by reference in their entirety.

FIELD OF THE INVENTION

The invention relates to a method of inducing a CTL response to an antigen by sustained, regular delivery of the antigen to an animal so that the antigen reaches the lymphatic system.

BACKGROUND OF THE INVENTION

Cytotoxic T lymphocytes (CTL) are white blood cells found in the blood, spleen and lymph. CTL have the ability to attack and kill other cells of the body in a highly specific manner. When CTL are stimulated by specific antigen, they migrate through the tissues of the body on a "search and destroy" mission for cells bearing the specific antigen. Whether of viral origin or tumor associated, CTL detect antigen that is bound to major histocompatability complexes (MHC) on the surface of potential target cells. Once CTL have identified the antigen on the cell surface, their function is to deliver a lethal hit to the cell.

Although there are hundreds of millions of CTL that reside in the spleen, each individual CTL exclusively responds to a unique and specific antigen. These individual CTL, dubbed CTL precursors (CTLp), undergo cell division or proliferate upon activation by specific antigen to produce daughter cells with precisely the same antigen specificity as the parent cell. This proliferation increases the total number, and thus the frequency, of that specific CTLp in the body. A proportion of these newly generated CTL briefly recirculate through the body (termed effector CTL), and have the ability to identify and destroy cells bearing the specific antigen which they recognize. A significant body of experimental evidence suggests that CTL specific for tumor antigens can inhibit tumor growth. Unfortunately, most tumors have only a very weak capacity to stimulate CTL responses and there has been no means of inducing a CTL response then sustaining it over a period of time sufficient to continuously inhibit tumor growth. While many attempts to directly increase the capacity of tumor cells to stimulate tumor-clearing CTL responses in patients have been made, such attempts have met with limited success. Technical advances over the past ten years have, however, enabled the identification of natural peptide antigens that are present on tumor cells and which are recognized by CTL. These antigen targets include proteins expressed in significant overabundance, abnormally expressed embryonic proteins, protein products from mutated oncogenes or suppressor genes, or proteins derived from cancer-causing viruses present in tumor cells. The challenge has been to find a way in which to administer an antigen so that it induces an antitumor CTL response and maintains it over time. While many attempts have now been made to use these antigens clinically in a vaccine, the results have been less than satisfactory.

An explanation of why CTL therapies have been largely ineffective at eradicating or controlling tumors in a clinical setting include the following:

(a) Vaccine designs have been inadequate at initiating strong CTL responses;

(b) Tumor cells can down regulate MHC molecules, resulting in the loss of antigen presentation from the surface of cells, thereby escaping detection by CTL;

(c) After induction, effector CTL recirculation through the body is highly transient;

(d) After recirculation, CTL return to the spleen where they reside in a nonactive or resting state, and an increase in the numbers of CTLp residing in the spleen does not reflect active CTL immunity;

(e) In the case of tumors, regrowth of residual tumor cells following immunization goes undetected by CTLp residing in spleen in a "resting" state;

(f) Because CTL-stimulating antigen presenting cells (APC are targeted for destruction by the same CTL that they have activated, the CTL response is self-limiting, which precludes, under normal circumstances, the continuous stimulation for a long-lived CTL response.

A growing repertoire of tumor associated antigens are being discovered that are recognized by CTL. A variety of techniques have been suggested to render these antigens effective in CTL vaccines. These include immunization using synthetic peptide antigens mixed with an immunostimulatory adjuvant, such as the bacterial toxin BCG; inununization with multiple antigenic peptide systems (MAPS), immunization with "professional" antigen presenting cells, which are isolated from the patient, pulsed with peptide antigen and inoculated back into the patient as a vaccine; immunization with peptides designed to stimulate both CTL and T helper cell populations; immunization with viruses or bacteria engineered to express tumor antigens; and immunization with polynucleotide expression vectors (so called DNA vaccines). Unfortunately, none of these approaches has been an unqualified success, As discussed above, the lack of vigorous therapeutic effects with these vaccine platforms reflects at least to some degree problems associated with inducing a strong initial CTL response and with maintaining ongoing "active" CTL immunity.

Studies by Glenny during the first quarter of the century revealed that aluminum compounds could enhance the strength of diphtheria vaccines. This was ostensibly the first of a long history of observations supporting a "depot" theory of immunization, which postulates that antigen slowly leaking into the tissues over an extended time correlates with the antigenic potency of a vaccine. Today, this antigen depot paradigm forms the intellectual backdrop to most adjuvant development programs. In one form or another, depot type adjuvants are intended to prolong the course of antigen delivery, by forming a lesion at the site of injection, or simply by the slow degradability of the adjuvant itself, which mixed with the specific antigen forms a depot at the site of injection. A second function generally attributed to adjuvants are their immunostimulatory effects, which appears to trigger the immune system to respond to the vaccine. However, adjuvants are a double-edged sword. They have inherent toxicities. But it is a feature of these toxicities that achieves a desired immunostimulatory and/or depot effect. Side effects such as tissue damage and granulornatous reaction at the site of injection, fever, and in some cases systemic reactions, such as Reiter's syndrome-like symptoms, uveitis and arthritis, are some of the risks associated with the use of adjuvants. Currently, the only adjuvant approved by the FDA is alum. It is relatively safe but does have side effects such as erythema, subcutaneous nodules, contact hypersensitivity, and granulornatous inflammation.

More importantly, alum only acts to potentiate a limited number of antigens, and it very predominantly stimulates humoral antibody responses rather than CTL immunity. Thus so far adjuvants have proved to be very ineffective components for vaccines aimed at inducing clinically relevant CTL responses.

Recent attempts to induce CTL responses using dendritic cells or other antigen presenting cells, despite being cumbersome, have shown some promise. New recombinant virus or bacterial systems carrying genes for specific antigen are effective at inducing primary CTL responses. The most effective viruses, for example, that induce strong CTL responses are those which replicate aggressively in the host. Yet because of the risk for serious or lethal complications as a result of infection, recombinant virus used in a cancer vaccine must be only weakly replicative, or be completely replication deficient. This trade-off between virulence and efficacy is at present an intractable problem.

DNA (or polynucleotide) vaccines are also being developed for the purpose of inducing CTL immunity. Once again, the system has intrinsic limitations that preclude its efficacy in inducing long-lasting CTL immunity. The DNA vaccines consist of a plasmid or similar genetic construct for expressing the antigen of interest. Uptake of the plasmid system by cells of the body results in expression of the antigen and induction of CTL. However, once cells expressing the construct have succeeded in inducing CTL, they are themselves targets for eradication by the CTL. The CTL inducing effect is thus again transient. Moreover, the polynucleotide vaccines have thus far suffered from poor efficiency in terms of CTL induction.

With difficulties in achieving strong primary and/or persisting CTL responses, there are a number of clinical trial groups now using repeated injections of cancer vaccines. The use of antigenically complex materials in the vaccine formulation, such as recombinant virus, or the costs associated with repetitive treatment using cultured APC will, however, make such an approach difficult. On the one hand, repetitive immunization with antigenically complex materials drives the immune system to elaborate a humoral antibody, as opposed to a CTL response, while on the other hand, use of a minimal CTL antigen (such as a nonamer peptide) which does not efficiently drive an antibody response, has also failed to induce a CTL response. Attempts to develop adjuvants that enhance the immunostimulatory aspects of minimal CTL antigens have resulted in the production of materials (i.e. adjuvants) that also induce a competing humoral immune response, or, which simply offer little CTL stimulatory effect.

It has also been suggested that certain controlled release technology using microspheres or liposomes with subunit antigens and peptides might be effective to enhance immunogenecity. The combination of sustained release and depot effect is suggested to reduce the amount of antigen needed and eliminate booster shots. However, the preparation of such compositions is difficult and unpredictable, and vaccine formulations based on this technology have not been translated into effective clinical treatments.

As can be seen from the foregoing, there has been little success at developing a CTL vaccine that is both capable of inducing a strong CTL response then sustaining that response over time. The development of a vaccine with these capabilities is essential before effective anti-tumor therapy based on CTL immunity can be contemplated.

OBJECTS OF THE INVENTION

An object of this invention is to provide a method for inducing or sustaining a specific CTL immununological response in a mammal over time.

Another object of this invention is to provide a method for treating a mammal having a malignant tumor or infectious disease by inducing and sustaining an immunological attack on the malignant tumor or infectious disease in the mammal.

It is a further object of this invention to provide an article of manufacture useful for inducing and sustaining a specific immunological CTL response in a mammal over time.

It is a further object of this invention to provide an article of manufacture useful for treating a mammal having a malignant tumor or infectious disease, which article is designed to induce and maintain an immunological attack on the malignant tumor or infectious disease in the mammal.

It is a further object of this invention to provide a portable device for sustained delivery of an antigen to a mammal having a malignant tumor or infectious disease, where the antigen stimulates the mammal's immune system to attack the tumor or infectious disease and the device is located outside the mammal.

It is still a further object of this invention to provide an implantable device for sustained delivery of an antigen to a mammal having a malignant tumor or infectious disease, where the antigen stimulates the mammal's immune system to attack the tumor or infectious disease.

It is a further object of this invention to provide antigen compositions and containers therefor that are useful in the methods, devices, and/or articles of manufacture of this invention.

Other objects of this invention may be apparent to those of skill in the art by reading the following specification and claims.

SUMMARY OF THE INVENTION

In one aspect of the invention, a method is provided for inducing an immunological CTL response to an antigen by sustained, regular delivery of the antigen to a mammal so that the antigen reaches the lymphatic system. In particular, the antigen is delivered to the mammal at a level sufficient to induce an immunologic CTL response in the mammal and the level of the antigen in the mammal's lymphatic system is maintained over time sufficient to maintain the immunologic CTL response. Preferably, the antigen is delivered directly to the mammal's lymphatic system, such as to the spleen, a lymph node or lymph vessel.

Also provided is a method of treating an animal having a disease, or being predisposed to a disease, to which the animal's immune system mounts a cell-mediated response to a disease-related antigen to attack the disease. In this aspect of the invention, a disease-matched antigen is delivered to the animal at a level sufficient to induce an increased CTL-response in the animal which is then maintained in the animal by sustained, regular delivery of the disease-matched antigen to the animal for a time sufficient to treat the disease. The sustained, regular delivery of the antigen is done in a manner that maintains the level of antigen in the animal's lymphatic system. Preferably, the sustained, regular delivery is achieved by pumping a physiologically-acceptable, composition of the antigen from a device held external of or implanted in the animal's body so that the antigen reaches the animal's lymph system. Optionally, a cytokine that is capable of enhancing the CTL response is delivered and/or maintained along with the antigen. Diseases addressed in this manner include cancer and pathogenic diseases.

In a further aspect of the invention, an article of manufacture is provided for delivering an antigen that induces a CTL response in an animal. In particular, the article comprises a reservoir of a physiologically-acceptable, antigen-containing composition that is capable of inducing a CTL response in an animal; a pump connected to the reservoir to deliver the composition at a defined rate; a transmission line to discharge the composition from the reservoir; and, optionally, a delivery line connected to the transmission line, which delivery line is of a size suitable for positioning in the animal and for delivery of the composition in a manner that reaches the lymphatic system of the animal.

In a further aspect of the invention, a process is provided for preparing a system useful for inducing a sustained CTL response in an animal needing such a response, which comprises placing a physiologically-acceptable, antigen-containing composition in a reservoir having a pump for delivering the composition at a defined rate through a transmission line to the animal.

Another aspect of the invention is a method of inducing and/or sustaining an immunological CTL response in a mammal by delivering an antigen in the form of a polypeptide directly to the lymphatic system of the mammal. The antigen can be delivered at a level sufficient to induce an immunologic CTL response in the mammal and the level of the antigen in the mammal's lymphatic system is preferably maintained over time sufficient to maintain the immunologic CTL response.

The antigen can be an 8–10 amino acid peptide. Further, the peptide sequence can be derived from a tumor-associated antigen. Examples of tumor-associated antigens include MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, alpha-fetoprotein , β-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

The peptide sequence also can be derived from a microbial antigen. Further, the antigen can be provided as a component of a microorganism or mammalian cell. Examples of microorganisms include a protozoan, a bacterium, a virus, and the like; the mammalian cell can be an antigen presenting cell, such as, for example, a dendritic cell.

The antigen can be a native component of the microorganism or mammalian cell. The microorganism or mammalian cell can include, for example, an exogenous antigen. Also, the microorganism or mammalian cell can include a recombinant nucleic acid encoding or promoting expression of the antigen. The microorganism or mammalian cell can express a tumor-associated antigen, or a microbial antigen native to a second microbial species. The antigen can be provided as an 8–10 amino acid peptide.

The present invention in another aspect includes a method of inducing and/or sustaining an immunological CTL response in a mammal by delivering an antigen, in the form of a vector that can include a nucleic acid encoding the antigen, directly to the lymphatic system of the mammal. The antigen can be delivered at a level sufficient to induce an immunologic CTL response in the mammal and the level of the antigen in the mammal's lymphatic system is preferably maintained over time sufficient to maintain the immunologic CTL response.

The vector can be a plasmid and the like. The vector further can include a bacterium and the like. The bacterium, for example, can include *Listeria, Shigella, Salmonella, Escherichia*, and the like. The vector, for example, can be a virus, such as, for example, pox viruses, adenoviruses, adeno-associated viruses, retroviruses, herpesviruses, and the like.

The nucleic acid can encode, for example, a tumor-associated antigen. Examples of tumor-associated antigens include MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, mn-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, alpha-fetoprotein , β-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

The nucleic acid can encode, for example, a microbial antigen. Examples of microbial antigens include a viral antigen, a bacterial antigen, a protozoal antigen, and the like. The nucleic acid can encode, for example, a protein or other polypeptide. The nucleic acid also can encode an 8–10 amino acid peptide.

The nucleic acid can be plasmid DNA in a formulation comprising about 1–10% ethyl alcohol, 0–1% benzyl alcohol, 0.25–0.5 mM EDTA and a citrate-phosphate buffer of pH 7.4–7.8, comprising about 3-50 mM citrate and about 90–200 mM phosphate. For example, the formulation can include 1% ethyl alcohol, 1% benzyl alcohol, 0.5 mM EDTA and a citrate-phosphate buffer of pH 7.4 to 7.8 comprising 50 mM citrate and 100 mM phosphate.

The invention in another aspect provides a method of inducing and/or sustaining an immunological CTL response in a mammal by delivering a microorganism or mammalian cell directly to the lymphatic system of the mammal. The microorganism or mammalian cell are preferably delivered at a level sufficient to induce an immunologic CTL response in the mammal and the level of the microorganism or mammalian cell in the mammal's lymphatic system is preferably maintained over time sufficient to maintain the immunologic CTL response.

A further aspect of the invention is a method of inducing and/or sustaining an immunological CTL response in a mammal by delivering a nucleic acid, capable of conferring antigen expression, directly to the lymphatic system of the mammal. The nucleic acid can be delivered at a level sufficient to induce an immunologic CTL response in the mammal and the level of the nucleic acid in the mammal's lymphatic system is preferably maintained over time sufficient to maintain the immunologic CTL response.

A further aspect of the invention is a method of inducing and/or sustaining an immunological CTL response in a mammal by delivering a non-peptide antigen directly to the lymphatic system of the mammal. The antigen is preferably delivered at a level sufficient to induce an immunologic CTL response in the mammal and the level of the antigen in the mammal's lymphatic system is preferably maintained over time sufficient to maintain the immunologic CTL response.

The invention also provides an article of manufacture for delivering an antigen that induces a CTL response in an animal. In particular, the article can be an external device. The article can include a reservoir of a physiologically-acceptable, antigen-containing composition that can be capable of inducing a CTL response in an animal, a pump connected to the reservoir to deliver the composition at a defined rate, a transmission line to discharge the composition from the reservoir; and, a delivery line connected to the transmission line. The delivery line can include a catheter of at least 20 mm for positioning in the animal and for delivery of the composition to the lymphatic system of the animal.

BRIEF DESCRIPTION OF THE DRAWINGS

The invention will now be described in relation to the drawings in which:

FIG. 8. Protective immunity against systemic and peripheral virus infection following intra-lymph node immunization with DNA. LCMV titer in spleen (A) and Vacc-G2 vaccinia titers in ovary (B) following indicated immunization and subsequent viral challenge.

FIG. 11. Average % supercoiled DNA in formulations 1–9 over 7 days.

DETAILED DESCRIPTION OF THE INVENTION

Method of Treatment

Figure 1:
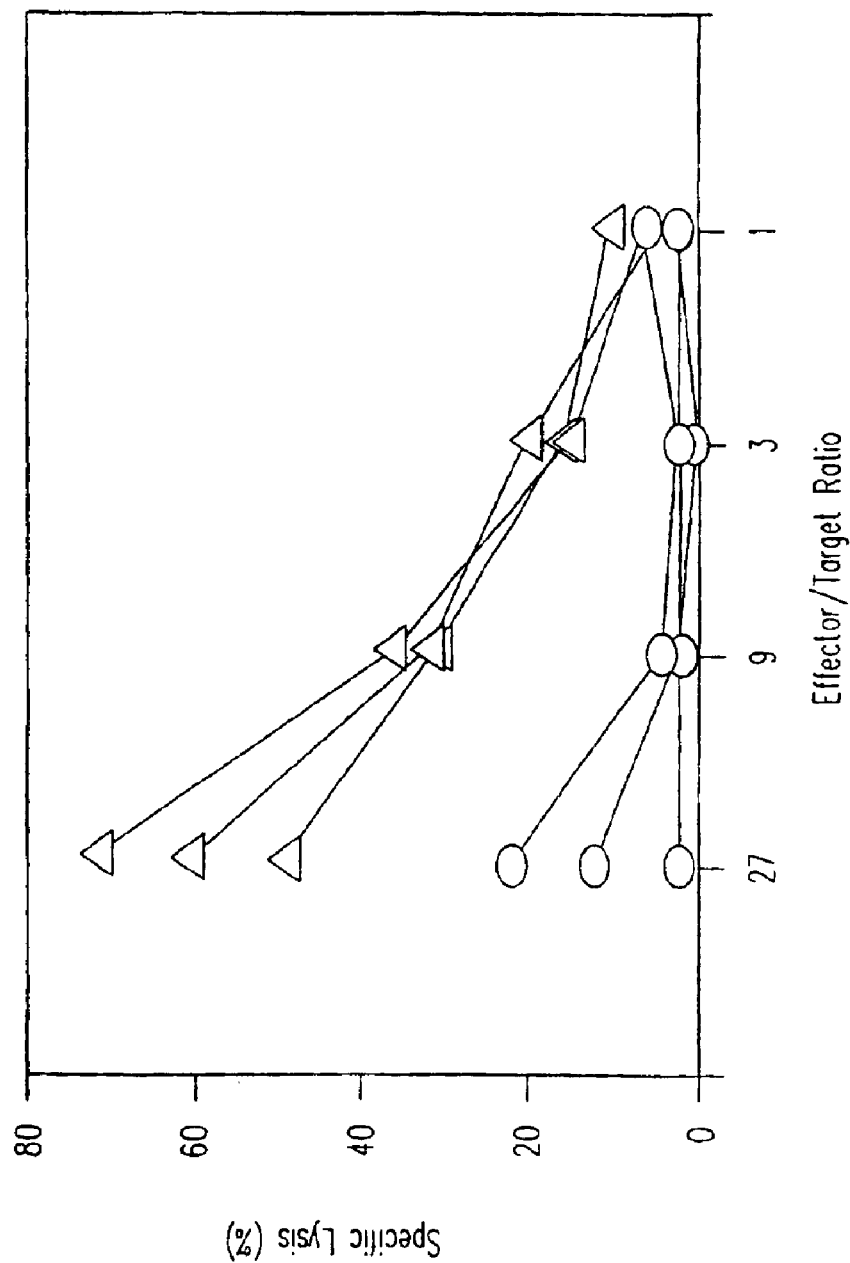
FIG. 1 is a graph showing the lysis of target cells by CTL versus the effector/target ratio when antigen is delivered as a single dose (circles) and when antigen is delivered by a continuous pump (triangles).

One aspect of this invention is a method for inducing or sustaining a specific immunological response (i.e., a CTL response) in an animal that has a disease (or predisposition to a disease) in which the animal's immune system may attack the disease with a natural CTL response. The response and diseases are discussed in greater detail hereinafter. The method has particular value for treating an animal having a malignant tumor in order to inhibit the growth of the tumor or for treating a chronic infectious disease such as hepatitis or AIDS.

The method, along with other aspects of the invention, is useful in an animal having an immune system that includes a lymphatic system. This generally includes vertebrates, specifically mammals and particularly humans. Thus, this invention will find use in treating humans of all ages as well as in treating animals, i.e. in veterinary uses. The invention may be used for treating livestock such as cattle, sheep, pigs, goats, and the like or for treating household pets such as dogs, cats, rabbits, hamsters, mice, rats, and the like. The primary use will be for treating humans that are in need of having a specific immunological response sustained for treatment of a disease such as cancer or chronic infections.

A key aspect of this invention is the delivery of an appropriate antigen to the lymphatic system of the animal being treated and sustaining the delivery over time. This is based in part on the observation that a strong induction and a sustained CTL response require ongoing antigenic stimulation of the lymphatic system. In a human, the lymphatic system includes lymph, lymphocytes, lymph vessels, lymph nodes, tonsils, the spleen, the thymus gland, and bone marrow. The lymphatic system performs three basic functions. First, it helps maintain fluid balance in the tissues. Approximately 30 L of fluid pass from the blood capillaries into the interstitial spaces each day, whereas only 27 L pass from the interstitial spaces back into the blood capillaries. If the extra 3 L of interstitial fluid were to remain in the interstitial spaces, edema would result, causing tissue damage and eventual death. These 3 L of fluid (i.e. lymph) enter the lymph capillaries, then passes through the lymph vessels to return to the blood. Lymph is similar in composition to plasma. In addition to water, lymph contains solutes derived from two sources: (1) substances in plasma such as ions, nutrients, gases, and some proteins pass from blood capillaries into the interstitial spaces to become part of the lymph; and (2) substances derived from cells within the tissues such as hormones, enzymes, and waste products are also found in lymph.

The lymphatic system's second basic function is to absorb fats and other substances from the digestive tract. Special lymph vessels called lacteals are in the lining of the small intestine. Fats enter into the lacteals and pass through the lymph vessels to the venous circulation. The lymph passing through these capillaries has a milky appearance because of its fat content, and it is called chyle.

Figure 5:
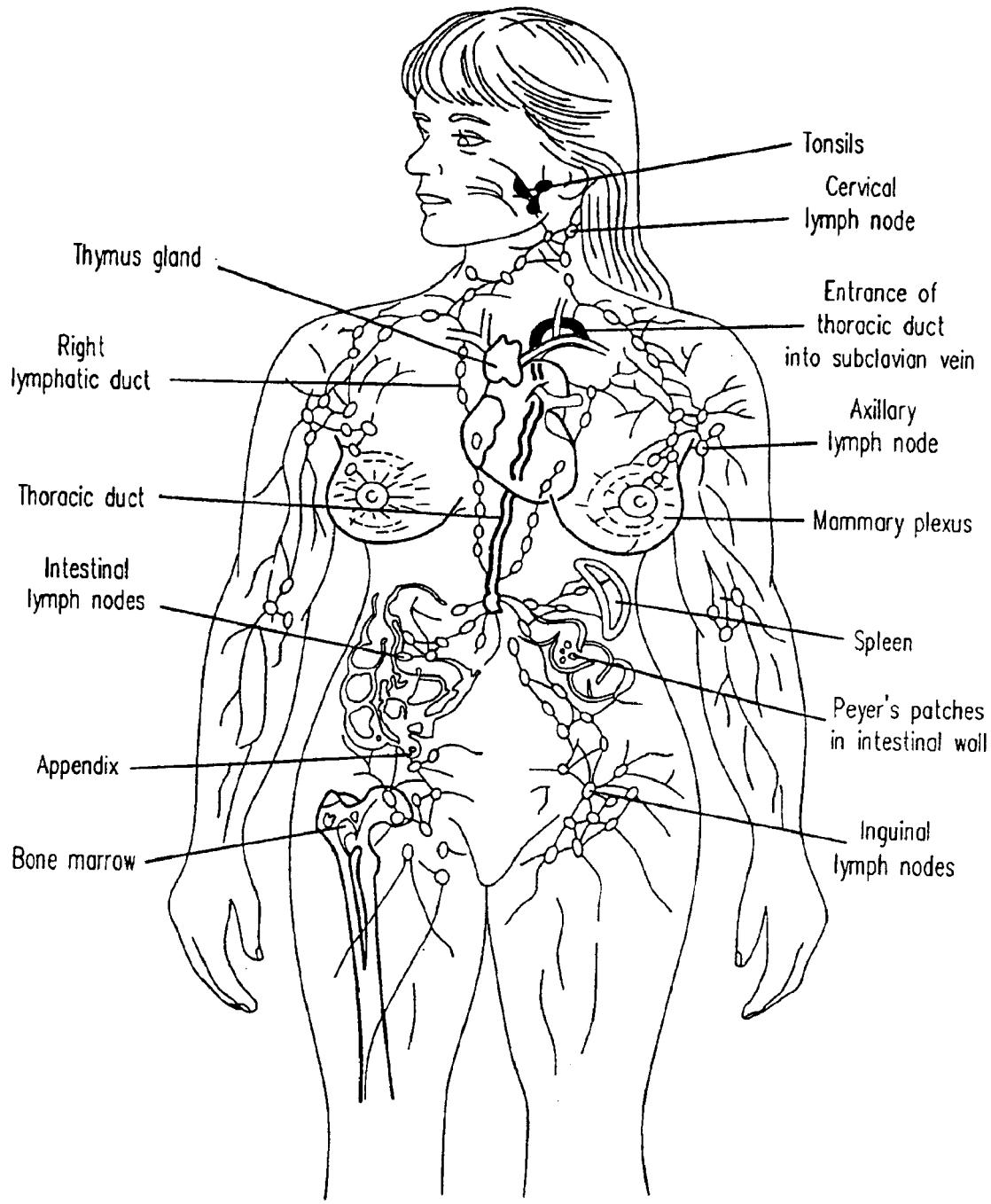
FIG. 5 is a rough schematic of a human lymphatic system.

The third basic function of the lymphatic system is to act as part of the body's defense system. The lymph nodes filter lymph, and the spleen filters blood, removing microorganisms and other foreign substances. This third function is the function most important to this invention in that the antigen must be delivered to the lymph system at a level sufficient to elicit the desired, specific immunological response in the animal. FIG. 5 is a schematic representation of a human lymphatic system showing the major lymphatic organs and vessels.

As hereinbefore mentioned, the present invention relates to a method of inducing or sustaining a specific immunological response (particularly a CTL response) to an antigen in an animal over time. The method comprises delivering the antigen to the animal in a manner that delivers the antigen into the lymphatic system of an animal to sustain the desired response over time. Generally this is done by establishing a mechanism to transfer an antigen from a reservoir to the animal's lymphatic system on a regular basis over time. The antigen may be delivered by a variety of methods that target intralymphatic presentation, including subcutaneous injection, direct injection into the lymphatic system by an antigen delivery vehicle that is implanted, preferably at or near a lymphatic organ, or by an antigen delivery vehicle that is external to the animal but contains a means (e.g. a needle or catheter) to deliver the antigen into the lymphatic system. By this method one can avoid multiple ongoing injections and can also avoid the use of including professional antigen-presenting cells in the composition held in the reservoir.

The method of this invention can be viewed as inducing CTL immune response by providing high continuous local concentrations of antigen, which otherwise is quickly removed and degraded from the body after bolus injection. Potent activation of CD8+ T cells requires signaling through the T cell receptor (TCR) in a manner that is dependent on both quantitative and qualitative factors. Quantitative factors refer to the number of TCRs engaged by peptide-MHC complexes. Qualitative considerations include the duration of engagement of the TCR by peptide-MHC complexes, with specific peptide-MFIC complexes. Sustained regular deliveries of antigen allows optimal conditions to be established for inducing CD8+ T cells.

The antigen is delivered to the animal so that the antigen is present in the animal's lymphatic system on a sustained basis over a period of time. That is to say, it is delivered in such a way that the presence of the antigen is maintained over the period of time in the animal's lymphatic system. Thus, the antigen is delivered to the animal on a regular basis, i.e. the antigen is delivered regularly without significant interruption over the period of time. This regular delivery is achieved by the constant delivery of the antigen at low levels directly to the lymphatic system using an external device or an implantable device, as discussed hereinafter. Alternatively, the antigen can be delivered at higher levels to the animal by subcutaneous injection with indirect absorption or equilibration with the lymph system. Delivery on a regular basis is meant to include intermittent (stopping and transmitting at intervals) as well as continuous (transmitting without interruption) delivery. In intermittent delivery, the times transmission is stopped will not be enough to reduce the level of antigen in the animal's lymphatic system to eliminate the desired specific immunological response. Thus, the antigen may be delivered in pulses or small doses over time.

Preferably, the sustained delivery is achieved by the positioning of a means of delivery so that the animal being treated does not have to receive multiple injections of the antigen, but instead has only one insertion of the means for delivery, e.g. an insertion of a catheter or needle for infusion of a suitable antigen-containing composition or the surgical implantation of an implantable device that releases an appropriate, antigen-containing composition on a sustained basis.

The period of time over which the antigen will be released will be a time sufficient to induce and maintain the desired specific immunological response, e.g. to maintain a CTL response, and in the case of an animal with a tumor or infection, at a level sufficient to stimulate the immune system to attack the tumor and inhibit its growth or to attack the infection. Generally, this period of time may vary from a few days, e.g. a week, to a year or more. Preferably, the treatment, i.e. sustained delivery of the antigen, will extend for at least seven days and no more than six months. It has been found that the CTL response is induced by administration for at least seven days. To determine the period of time, the attending physician will evaluate, i.e., the severity of the condition, the strength of the patient, the antigenic response (e.g., the level of CD8+ cells measurable in the patient's system), the presence of toxic effects, and other factors known to one of skill in the art. Ultimately the time for sustained delivery in a cancer patient will be that necessary for improvement in the patient as evidenced by reduction in the size of the tumor, the rate of growth of the tumor, and/or the improvement in the overall health of the patient being treated. In the treatment of infectious diseases the treatment is continued until the health of the patient improves sufficiently to stop treatment.

The underlying immunological rationale for the utility of this invention arises from certain immunological considerations, The immune system has evolved to protect the host from microbial infection. CD4+ T cells together with B cells are the main components of the immune system humoral effector arm, which is crucial to eliminate extracellular pathogens or toxins. In contrast, the CD8+ T cell arm of the immune system is mainly responsible for eliminating intracellular pathogens, i.e. most importantly viruses, either via cytokine release or by cytotoxic activity. It is now emerging that these most efficient "killer cells" of the immune system would best serve as the primary effector cells in tumor immunotherapy. An object of this invention is to mount a disease-specific CTL response (CD8+ T cell response) against the disease and sustain it over time, e.g., a tumor specific or microbial specific CTL response.

CD8+ T cells recognize antigenic oligopeptides presented on HLA class I molecules of target cells, e.g., tumor cells. The sequences of many HLA-A1 and HLA-A2 presented tumor and pathogen specific antigen peptides have recently been characterized. These peptides may be used in this invention to induce, e.g., a melanoma-specific CD8+ T cell response. These peptides are discussed hereinafter.

In contrast to viral infection, class I-binding oligopeptides show only low immunogenicity. Most viruses induce peak CD8+ T cell responses around 7–10 days after systemic spread. This invention aims at enhancing the immunogenecity of class I binding oligopeptides by sustained, regular release of peptide into a lymphatic system and continued release into the lymphatic system.

In contrast to antibody-mediated B cell memory, which is long lived, T cell memory appears to be short lived or non-existent. In accordance with this invention, maintenance of functional T cell memory depends on persistence of antigen through continued, regular administration of the desired antigen. Having made this invention and looking at past concepts that might support this underlying rationale, some evidence includes the observation that delayed type hypersensitivity (DTH) of the tuberculin type (the only functional test for T cell memory in humans), can be elicited only in granulomatous disease, such as tuberculosis (tuberculin test), leprosy (lepromin test), brucellosis (brucellin test), sarcoidosis (Kveim test), Histoplasmosis (histoplasimin test) etc., but no such test could be established for non-granulomatous infectious disease. A factor that all granulomatous diseases have in common, is that the antigen persists within the granuloma-professional antigen presenting cells can use this reservoir to continuously restimulate specific T cells in lymphoid organs. In mice models (see Example 3) it is demonstrated that maintenance of functional CD8+ T cell memory was strictly dependent on continuous antigenic restimulation.

To determine whether a CTL response is obtained in an animal being treated in accordance with this invention, one measures the level of CD8+ cells (i.e. CTL) present in the blood or lymphatic organs such as the spleen or lymph nodes. This determination is done by first measuring the level of CD8+ cells before performing the method of this invention and measuring the level during treatment, e.g. at 7, 10, 20, 40 days, etc. The level or strength of the CD8+ (CTL) response can be assessed in vivo or in vitro. In humans, there exists so far only one in vivo test to measure CD8+ T cell responses, which is a skin test. In this skin test, HLA class I binding peptides are injected, intradermally (such as described in Jager, E. et al. Granulocyte-macrophage-colony-stimulating Factor Enhances Immune Responses To Melanoma-associated Peptides in vivo Int. J Cancer 67, 54–62 (1996)). If a CTL response is present, these cells will recognize and attack peptide pulsed dermal cells, causing a local inflammatory reaction either via cytokine release or the cytotoxic mechanism (Kündig, T. M., Althage, A., Hengartner, H. & Zinkernagel, R. M. A skin test to assess CD8+ cytotoxic T cell activity. Proc. Natl. Acad Sci. USA 89:7757–776 (1992)). This inflammatory reaction can be quantified by measuring the diameter of the local skin rash and/or by measuring the diameter of the infiltrate (i.e., the swelling reaction). As an alternative to the injection of soluble free peptide, the HLA-class I binding peptide can also be injected intradermally in a bound form, e.g., bound to extracorporally derived dendritic cells. In other mammals, additional, although experimental, in vivo tests to assess CD8+ T cell responses exist. For example, in a mouse model, CD8+ T cell responses can be measured by challenge infection with a vaccinia recombinant virus expressing the peptide used for immunization. While naïve mice succumb to the infection with the vaccina recombinant virus, mice with preexisting CD8+ T cell immunity against the peptide epitope expressed by the vaccinia recombinant virus, are immune to reinfection. The level of immunity to reinfection can be quantified as the factor of reduction of the vaccinia virus titer recovered from mouse organs after challenge infection (Bachmann, M. F. & Kundig, T. M. In vitro vs. in vivo assays for the assessment of T- and B-cell function. Curr. Opin. Immunol. 6, 320–326 (1994)). For example, 5 days after challenge infection, a typical vaccinia recombinant virus titer recovered from a mouse ovary would be around $10^7$ pfu per ovary, whereas the vaccinia recombinant virus titer in a mouse with a preexisting CD8+ T cell response against the recombinant gene product would for example be around $10^3$ pfu per ovary. Such a 10,000 fold-reduction in virus titer reflects biologically significant preexisting CD8+ T cell activity against the recombinant gene product.

The level of CD8+ T cell responses can also be quantified in vitro, by estimating the number of CD8+ T cells specific for the antigenic peptide in question. In a naive mammal the so called "frequency", i.e., the number of specific CD8+ T cells divided by the number of non-specific white blood cells, is less than $10^{-6}$. After successful immunization, the frequency increases due to proliferation of specific T cells. During an acute viral infection, for example, the frequency of specific CD8+ T cells may rise to $10^{-2}$. Then, after elimination of the virus, the frequency of specific CD8+ T cells usually drops to a "memory" level of around $10^{-4}$. Thus, the CD8+ T cell response can be quantified by measuring the frequency of specific CD8+ T cells. The higher the frequency, the stronger the response. The classical assays used to measure the frequency of specific CD8+ T cells are based on limiting dilution cell culture techniques, as described in detail by Kündig, T. M. et al. (On the role of antigen in maintaining cytotoxic T cell memory. Proceedings of the National Academy of Sciences of the United States of America 93, 9716 972') (1996)). A novel approach to estimate the frequency of specific CD8+ T cells is to construct soluble class I MHC (for use in mice) or HLA molecules (for use in humans) with a peptide bound to their groove, so that the specific T cell receptors will bind to these complexes. These complexes can be labeled for detection, for example, with a fluorescent substance, allowing for detection by flow cytometry.

One current procedure to render peptides immunogenic is to inject them in context with "nature's most potent adjuvant", i.e., professional antigen presenting cells (APCs) such as dendritic cells (DCs), (Steinmann, R. M., The dendritic cells system and its role in irnmunogenicity, Annual Review of Immunology 9, 271–96 (1991)). DCs are the most potent APCs of the immune system. They can now be cultured in vitro by adding granulocyte macrophage colony stimulating factor (GM-CSF) and tumor necrosis factor alpha (TNF-alpha) or interleukin-4 (IL-4) to progenitors isolated from the blood of patients or mice (Inaba, K. el al., Identification of proliferating dendritic cell precursors in mouse blood, Journal of Experimental Medicine 175, 1157–1167 (1992)). Large numbers of DCs can then be pulsed with tumor specific antigen peptides and are injected back into the patient, where they migrate into lymphatic organs to induce T cell responses (Young, J. W. & Inaba, K., Dendritic Cells As Adjuvants For Class I Major Histocompatibility Complex-restricted Anti-tumor Immunity, Journal of Experimental Medicine 183, 7–11 (1996)). An object of this invention is to circumvent the time-consuming, labor intensive procedure of culturing DCs after isolation of DC progenitors and deliver the antigen to the lymphatic system free of APCs such as DCs. The method of this invention, i.e., the sustained, regular delivery of antigen into a lymphatic organ, allows sufficiently high local concentrations of antigen inside the lymphatic organ, such that professional antigen presenting cells, e.g., dendritic cells, can be loaded with peptide in vivo. This can be viewed as a method of loading antigen presenting cells (dendritic cells) in vivo for inducing a CTL response.

The method of the present invention is clearly advantageous over the prior art methods for inducing a CTL response against a tumor or virus. For example, the present invention does not require repetitive immunizations to effect for prolonged anti-tumor immunotherapy. The sustained delivery of the antigen maintains the CTL response that could ultimately afford a prolonged aggressive posture of CTL against tumor cells, more thorough eradication, and protection against recurrence during the vaccine treatment. In the absence of antigen, CTL that have undergone primary activation soon cease to recirculate through the body, soon finding their way to the spleen where they become quiescent. Since CTL must immediately deliver a lethal hit, their residence in the spleen precludes an active role in protection against infections or tumor growth at distant sites in the body. The controlled release of antigen recognized by CTL in this invention circumvents this outcome as antigen delivery is maintained. Sustained released antigen delivery to the lymphatic system by this invention solves two major problems: it provides for potent CTL stimulation that takes place in the milieu of the lymphoid organ, and it sustains stimulation that is necessary to keep CTL active, cytotoxic and recirculating through the body.

Another fundamental improvement of the present method over prior art is that it facilitates the use of inherently non-immunogenic peptide antigens for CTL stimulation without the combined use of conventional adjuvants. This is very beneficial as most experimental adjuvants are toxic and poorly suited for use in humans. In addition adjuvants stimulate the TH2-type humoral immune response that negatively affects the CTL response. Further, since conventional adjuvants are not required, only the minimal antigenic epitope for a CTL response is required in the formulation.

An additional advantage to the method of the present invention, where it embodies the use of mechanical delivery systems, is that the antigen delivery can be stopped if any adverse immunological effects are observed, For example, in vaccines against melanoma, CTL have been induced to attack not only malignant melanocytes but also healthy tissue, causing "vitiligo." The ability to discontinue a CTL vaccine at any time is a significant advance in vaccine safety. Peptides have a short half-life due to catabolism in the liver. Therefore, the stimulation-effect falls soon after cessation of delivery.

As pointed out before, the method of this invention has two parts: (1) inducing an increased CTL response and (2) maintaining the response. The inducing and maintaining may be performed using the same device, as discussed hereinafter, or the inducing may be done separately, e.g., by a separate injection of an antigen then following up with sustained delivery of the antigen over time to maintain the response.

Diseases Treated According to the Invention

In general, this invention is useful for treating an animal having (or being predisposed to) any disease to which the animal's immune system mounts a cell-mediated response to a disease-related antigen in order to attack the disease. Thus, the type of disease may be a malignant tumor or a chronic infectious disease caused by a bacterium, virus, protozoan, helminth, or other microbial pathogen that enters intracellularly and is attacked, i.e., by the cytotoxic T lymphocytes, In addition, the invention is useful for treating an animal that may be at risk of developing such diseases.

Malignant Tumors

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor, or neoplasm. A tumor that is not capable of indefinite growth and does not invade the healthy surrounding tissue extensively is benign. A tumor that continues to grow and becomes progressively invasive is malignant; the term cancer refers specifically to a malignant tumor. In addition to uncontrolled growth, malignant tumors exhibit metastasis; in this process, small clusters of cancerous cells dislodge from a tumor, invade the blood or lymphatic vessels, and are carried to other tissues, where they continue to proliferate. In this way a primary tumor at one site can give rise to a secondary tumor at another site. The methods, devices and articles of manufacture discussed herein are useful for treating animals having malignant tumors.

Malignant tumors treated according to this invention are classified according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this invention is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. The malignant tumors may show up at numerous organs or tissues of the body to establish a cancer. The types of cancer that can be treated in accordance with this invention include the following: bladder, brain, breast, cervical, colo-rectal, esophageal, kidney, liver, lung, nasopharangeal, pancreatic, prostate, skin, stomach, uterine, and the like. The present invention is not limited to the treatment of an existing tumor or infectious disease but can also be used to prevent or lower the risk of developing such diseases in an individual, ie., for prophylactic use. Potential candidates for prophylactic vaccination include individuals with a high risk of developing cancer, i.e., with a personal or tuminal history of certain types of cancer.

The incidence of skin cancer has increased substantially over the last decades. Lifetime analysis indicates that around 1/1500 humans born in 1935, 1/600 born in 1960, 1/100 born in 1990 and a projected 1/75 humans born in the year 2000 will have melanoma in their lifetime. Surgical excision usually cures melanoma. However, even small looking lesions may have already metastasized at the time of diagnosis. The prognosis of metastasized melanoma is very poor and correlates with the thickness of the primary tumor and with its localization.

The current treatment of malignant melanoma aims at surgical removal of the primary tumor, If metastases are present, chemotherapy and biological response modifiers are additionally used. However, patients with stage IV malignant melanoma are almost invariably incurable and treatments are palliative. Patients with Stage IV malignant melanoma have a median survival time of approximately one year and only a 10% chance of long-term survival. There is at present no generally accepted standard therapy for metastatic melanoma. Objective response rates to mono- or polychemotherapy are low in comparison with other tumors, reaching no more than 15–35%. An improved treatment outcome in stage IV malignant melanoma seems unachievable either by chemotherapeutic combinations or by increasing doses to levels where autologous bone marrow transplantation becomes necessary. The method of this invention is useful for treating malignant melanoma, even at Stage IV.

Infectious Diseases

Infectious diseases, which have plagued animal populations (particularly humans) throughout history, still cause millions of deaths each year. The infectious diseases that can be treated using this invention include those caused by pathogens such as bacteria, viruses, protozoa, helminths, and the like. These diseases include such chronic diseases such as acute respiratory infections, diarrheal diseases, tuberculosis, malaria, hepatitis (hepatitis A, B C, D, E, F virus), measles, mononucleosis (Epstein-Barr virus), whooping cough (pertussis), AIDS (human immunodeficiency virus I & 2), rabies, yellow fever, and the like. Other diseases caused by human papilloma virus or various strains of virus are treatable by this method.

In some instances, the mammal, in particular human, can be treated prophylactically, such as when there may be a risk of developing disease. An individual travelling to or living in an area of endemic infectious disease may be considered to be at risk and a candidate for prophylactic vaccination against the particular infectious agent. For example, the CTL response can be induced in a human expecting to enter a malarial area and/or while in the malarial area by using a CTL-inducing, -malaria-specific antigen to lower the risk of developing malaria. Preventative treatment can be applied to any number of diseases including those listed above, where there is a known relationship between the particular disease and a particular risk factor, such as geographical location or work environment.

Antigens Useful in the Invention

An antigen useful in this invention is one that stimulates the immune system of a mammal having a malignant tumor or infectious disease to attack the tumor and inhibit its growth or to destroy the pathogen causing the disease. Thus, the antigen used in the invention is matched to the specific disease found in the animal being treated. In this regard the antigen may be said to induce a CTL response (also referred to as a cell-mediated immune response), i.e. a cytotoxic reaction by the immune system that results in lysis of the target cells (e.g., the malignant tumor cells or pathogen-infected cells).

To determine whether an antigen is matched to a particular patient, whether human or other animal, the tissue type of the patient is first determined. If human, the tissue must demonstrate the appropriate human leukocyte antigen (HLA) capable of binding and displaying the antigen to CTL. It is preferable that the HLA typing be performed, on the target cells, since a significant portion of tumors escape immune detection by downregulating expression of HLA. Therefore HLA expression on normal cells of the patient does not necessarily reflect that found on tumor cells in their body. A tumor from a patient is also screened to determine if he or she expresses the antigen that is being used in the vaccine formulation. Immunohistochemistry and/or polymerase chain reaction (PCR) techniques both can be used to detect antigen in the tumor cells. Immunchistochemistry offers the advantage in that it stains a cross-section of tumor in a slide preparation, allowing investigators to observe the antigen expression pattern in cross-section of tumor, which is typically heterogeneous for antigen expression. PCR has the advantage of not requiring specific monoclonal antibodies for staining and is a fast and powerful technique. In addition, PCR can be applied in situ. Ideally, both immunohistochemical and PCR methods should be combined when assessing antigen expression in tumors. While the antigen compositions useful in this invention are designed to include the most commonly expressed tumor antigens (as discussed hereafter), not all tumors will express the desired antigen(s). Where a tumor fails to express the desired antigen, the patient is excluded for consideration for that particular antigen composition. Thus, an aspect of this invention is a process for preparing a device useful for providing a sustained CTL response over time by matching a subject's antigen specific to the tumor or pathogen in the subject, preparing a physiologically-acceptable composition of the antigen so matched, and combining the composition in a suitable delivery device as discussed in hereinafter.

Immune activation of CD8+ T cells generates a population of effector cells with lytic capability called cytotoxic T lymphocytes, or CTL. These effector cells have important roles in the recognition and elimination of malignant cells and pathogens. In general, CTL are CD8+ and are therefore class I MHC restricted, although in rare instances CD4+ class II-restricted T cells have been shown to function as CTL. Since virtually all nucleated cells in the body express class I MHC molecules, CTL can recognize and eliminate almost any altered body cell. CD8+ T cells recognize antigen presented on HLA class I molecules of tumor cells through T cell receptors.

The CTL-mediated immune response can be divided into two phases, reflecting different aspects of the cytotoxic T-cell response. The first phase involves the activation and differentiation of $T_c$ (CD8+) cells into functional effector CTLs. In the second phase, CTLs, recognize antigen—class I MHC complexes on specific target cells, initiating a sequence of events that culminates in target-cell destruction. Further detailed discussion of the process is found at Chapter 15 of the Second Edition of "Immunology" by Janis Kuby, W. H. Freeman and Company (1991).

The type of tumor antigen used in this invention may be a tumor-specific antigen (TSA) or a tumor-associated antigen (TAA), A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells. TSAs and TAAs can be jointly referred to as TRA or a tumor related antigen.

Tumor antigens useful in the present invention, whether tumor-specific or tumor-associated, must be capable of inducing a CTL-mediated immune response. The presence of tumor antigens that elicit a cell-mediated response has been demonstrated by the rejection of tumors transplanted into syngeneic recipients; because of this phenomenon, these tumor antigens are referred to as tumor-specific transplantation antigens (TSTAs) or tumor-associated transplantation antigens (TATAs). It has been difficult to characterize tumor transplantation antigens because they do not generally elicit an antibody response and therefore they cannot be isolated by immunoprecipitation. Many are peptides that are presented together with MHC molecules on the surface of tumor cells and have been characterized by their ability to induce an antigen-specific CTL.

The type of pathogen specific antigen useful in this invention may be short oligopeptides derived from pathogen proteins. These oligopeptides must bind to class I MHC (for use in mice), class I HLA (for use in humans), or class I molecules of any other mammals. Also, such class I molecule bound peptides should be recognizable by specific T cell receptors. Such oligopeptides usually have a length of 8–15 amino acids. Several examples of such pathogen derived oligopeptides, so called T cell epitopes, are given in Tables I and II.

The tumor antigens and pathogen-specific antigens useful in this invention are generally thought to be presented at the surface of an antigen presenting cell (APC) to stimulate the immune system through class I molecules of the major histocompatability complex (MHC) interactively with the CD8+ cells.

Antigens useful in the invention are generally protein-based entities of a molecular weight of up to 100,000 daltons. Appropriate antigens include, but are not limited to differentiation antigens, tumor-specific multilineage antigens, embryonic antigens, antigens of oncogenes and mutated tumor-suppressor genes, unique tumor antigens resulting from chromosomal translocations, viral antigens, and others that may be apparent presently or in the future to one of skill in the art. It is preferable that the antigen be a peptide of 8 to 15 amino acids in length that is an epitope of a larger antigen, i.e. it is a peptide having an amino acid sequence corresponding to the site on the larger molecule that is recognized and bound by a particular T-cell receptor. These smaller peptides are available to one of skill in the art by following the teachings of U.S. Pat. No. 5,747,269 to Rarnmensee et al. issued May 5, 1998; U.S. Pat. No. 5,698,396 to Pfreundschuh issued Dec. 16, 1997; and PCT Application Numbers PCT/EP95/02593 filed Jul. 4, 1995, PCT/DE96/00351 filed Feb. 26, 1996, all of which are incorporated herein by reference. Additional approaches to epitope discovery are described in U.S. Pat. No. 6,037,135 METHODS FOR MAKING HLA BINDING PEPTIDES AND THEIR USES and U.S. patent application Ser. No. 09/561,074 entitled METHOD OF EPITOPE DISCOVERY both of which are incorporated herein by reference in their entirety.

While in the general case the antigen ultimately recognized by a T cell is a peptide, it must be kept in mind that the form of antigen actually administered as the immunogenic preparation need not be a peptide per se. When administered, the epitopic peptide(s) may reside within a longer polypeptide, whether the complete protein antigen, some segment of it, or some engineered sequence. Included in such engineered sequences would be polyepitopes and epitopes incorporated into some carrier sequence such as an antibody or viral capsid protein. Such longer polypeptides may include epitope clusters as described in U.S. patent application Ser. No. 09/561,571 entitled "EPITOPE CLUSTERS," which is incorporated herein by reference in its entirety. The epitopic peptide, or the longer polypeptide in which it is contained, may be a component of a microorganism (e.g. a virus, bacterium, protozoan, etc.), or a mammalian cell (e.g. a tumor cell or antigen presenting cell), or lysates, whole or partially purified, of any of the foregoing. They may be used as complexes with other proteins, for example heat shock proteins. The epitopic peptide may also be covalently modified, such as by lipidation, or made a component of a synthetic compound, such as dendrimers, multiple antigen peptides systems (MAPS), and polyoximes, or may be incorporated into liposomes or microshperes, etc. As used in this disclosure the term "polypeptide antigen" encompasses all such possibilities and combinations. The invention comprehends that the antigen may be a native component of the microorganism or mammalian cell. The antigen may also be expressed by the microorganism or mammalian cell through recombinant DNA technology or, especially in the case of antigen presenting cells, by pulsing the cell with polypeptide antigen prior to administration. Additionally, the antigen may be administered encoded by a nucleic acid that is subsequently expressed by APCs. Finally, whereas the classical class I MHC molecules present peptide antigens, there are additional class I molecules which are adapted to present non-peptide macromolecules, particularly components of microbial cell walls, including without limitation lipids and glycolipids. As used in this disclosure the term antigen comprehends such macromolecules as well. Moreover, a nucleic acid based vaccine may encode an enzyme or enzymes necessary to the synthesis of such a macromolecule and thereby confer antigen expression on an APC.

A powerful method has been recently developed for identifying new peptides that are useful in the invention. Genes determined to express protein with high exclusivity in tumor cells or microbial cells (e.g. viruses) can be identified using a so called SEREX process, which involves expression cloning using tumor cell libraries and screening these libraries against immunoglobulin in patient sera. Over one hundred genes have recently been identified from tumor biopsies using this process. These genes can now be used in a peptide prediction algorithm developed by Hans-Georg Rammensee. Algorithms have been developed for all major HLA types found in the human population. First the protein sequence is "translated" based on the gene sequence. The algorithms can predict peptide epitopes for various HLA types based on the protein sequence. Since the predicted peptides are indeed predictions and are not always naturally found on cells, tumor samples are used to confirm the predicted peptides by actually isolating minute trace peptide from tumors. Being able to calculate the exact mass of the predicted peptides allows trace peptide identification using ultrasensitive mass spectrophotometry, which can detect peptides in quantities less that that which would permit peptide sequencing and identification. Once these tumor-associated peptides have been identified they are suitable for use in the invention, since peptides of a known sequence may be synthesized in large quantities (several grams) providing for sufficient amounts of peptides for use in this invention.

In addition to the imperfection of existing prediction algorithms for MHC binding, some peptides that would be fully capable of binding to MHC may never be liberated by protoelytic processing from the complete protein antigen. Methods for evaluating which peptides will be liberated by proteasomal processing have been developed, e.g. U.S. patent application Ser. No. 09/561,074 supra, increasing the efficiency with which useful epitopes can be discovered. Moreover, proteasomal processing can differ between target cell and APC such that care must be taken in the identification and selection of epitopes and in vaccine design so that the vaccine will induce a response that will in fact recognize the target cell. These issues are more fully discussed in U.S. patent application Ser. No. 09/560,465 entitled "EPITOPE SYNCHRONIZATION," which is incorporated herein by reference in its entirety.

Thus it can be seen that another aspect of this invention is a process for preparing a composition useful in a device of this invention as discussed hereinafter. The process comprises identifying a gene determined to express a protein with high exclusivity in a tumor or microbial cell, cloning cell libraries, screening the libraries against immunoglobulin in patient sera, using the algorithm defined in the literature developed by Hans-George Rammensee to predict an epitope for the HLA type protein based on the gene sequence, matching the predicted antigen sequence to a patient tumor sample, isolating the matched antigen, and preparing a composition of the antigen for use in a delivery device as discussed hereinafter.

Examples of large, protein-based antigens include the following:

Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23HI, PSA, TAG-72, CA 19-9, CA 72-4, CAM 17.1, NuMa, K-ras, β-Catenin, CDK4, Mum-1, p 15, p 16, 43-9F, 5T4, 791Tgp72, alpha-fetoprotein , β-HCG, BCA225, BTAA, CA 125, CA 15-3\CA 27.29\BCAA, CA 195, CA 242, CA-50, CAM43, CD68\KP1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS. These protein-based antigens are known and available to those of skill in the art in the literature or commercially.

Examples of peptide antigens of 8–15 amino acids include those set forth in Table I, Table II, and Table III. Table I sets forth antigens that are virally derived. The Table shows the virus type, the protein expressed by the virus, the amino acid (AA) position on the viral protein, the AA sequence of the T-cell epitope/MHC ligand, the type of MHC molecule presenting the antigen, and a reference source. A more complete list is provided in the book by Han-Georg Rammensee, Jutta Bachmann, and Stefan Stevanovic entitled "MHC Ligands and Peptide Motifs," Springer-Verlag, Germany, 1997 Landes Bioscience, Austin, Tex.). The reference number given in Table I is the same number (and reference source) given in Table 5.3 of the above Rammensee book, all of which is incorporated herein by reference.

TABLE I

Viral epitopes on MHC class 1 molecules

| Virus | Protein | AA Position | T cell epitope MHC ligand (Antigen) | MHC molecule | Ref. |
| --- | --- | --- | --- | --- | --- |
| Adenovirus 3 | E3 9Kd | 30–38 | LIVIGILIL (SEQ. ID NO.:1) | HLA-A*0201 | 104 |
| Adenovirus 5 | EIA | 234–243 | SGPSNTPPEI (SEQ. ID NO.:2) | H2-Db | 105 |
| Adenovirus 5 | EIB | 192–200 | VNIRNCCYI (SEQ. ID NO.:3) | H2-Db | 106 |
| Adenovirus 5 | EIA | 234–243 | SGPSNIPPEI (T > I) (SEQ. ID NO.:4) | H2-Db | 106 |
| CSFV polyprotein | NS | 2276–2284 | ENALLVALF (SEQ. ID NO.:5 | SLA, haplotype d/d | 107 |
| Dengue virus 4 | NS3 | 500–508 | TPEGIIPTL (SEQ. ID NO.:6) | HLA-B*3501 | 108, 109 |
| EBV | LMP-2 | 426–434 | CLGGLLTMV (SEQ. ID NO.:7) | HLA-A*0201 | 110 |
| EBV | EBNA-1 | 480–484 | NIAEGLRAL (SEQ. ID NO.:8) | HLA-A*0201 | 111 |
| EBV | EBNA-1 | 519–527 | NLRRGTALA (SEQ. ID NO.:9) | HLA-A*0201 | 111 |
| EBV | EBNA-1 | 525–533 | ALAIPQCRL (SEQ. ID NO.:10) | HLA-A*0201 | 111 |
| EBV | EBNA-1 | 575–582 | VLKDAIKDL (SEQ. ID NO.:11) | HLA-A*0201 | 111 |
| EBV | EBNA-1 | 562–570 | FMVFLQTHI (SEQ. ID NO.:12) | HLA-A*0201 | 111 |
| EBV | EBNA-2 | 15–23 | HLIVDTDSL (SEQ. ID NO.:13) | HLA-A*0201 | 111 |
| EBV | EBNA-2 | 22–30 | SLGNPSLSV (SEQ. ID NO.:14) | HLA-A*0201 | 111 |
| EBV | EBNA-2 | 126–134 | PLASAMRML (SEQ. ID NO.:15) | HLA-A*0201 | 111 |
| EBV | EBNA-2 | 132–140 | RMLWMANY1 (SEQ.ID NO.:16) | HLA-A*0201 | 111 |
| EBV | EBNA-2 | 133–141 | MLWMANYIV (SEQ. ID NO.:17) | HLA-A*0201 | 111 |
| EBV | EBNA-2 | 151–159 | ILPQGPQTA (SEQ. ID NO.:18) | HLA-A*0201 | 111 |
| EBV | EBNA-2 | 171–179 | PLRPTAPTI (SEQ. ID NO.:19) | HLA-A*0201 | 111 |
| EBV | EBNA-2 | 205–213 | PLPPATLTV (SEQ. ID NO.:20) | HLA-A*0201 | 111 |
| EBV | EBNA-2 | 246–254 | RMHLPVLHV (SEQ. ID NO.:21) | HLA-A* 0201 | 111 |
| EBV | EBNA-2 | 287–295 | PMPLPPSQL (SEQ. ID NO.:22) | HLA-A*0201 | 111 |
| EBV | EBNA-2 | 294–302 | QLPPPAAPA (SEQ. ID NO.:23) | HLA-A*0201 | 111 |
| EBV | EBNA-2 | 381–389 | SMPELSPVL (SEQ. ID NO.:24) | HLA-A*0201 | 111 |
| EBV | EBNA-2 | 453–461 | DLDESWDYI (SEQ. ID NO.:25) | HLA-A*0201 | 111 |
| EBV | BZLF1 | 43–51 | PLPCVLWPV (SEQ. ID NO.:26) | HLA-A*0201 | 111 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| EBV | BZLF1 | 167–175 | SLEECDSEL (SEQ. ID NO.:27) | HLA-A*02O1 | 111 |
| EBV | BZLF1 | 176–184 | EIKRYKNRV (SEQ. ID NO.:28) | HLA-A*0201 | 111 |
| EBV | BZLF1 | 195–203 | QLLQHYREV (SEQ. ID NO.:29) | HLA-*0201 | 111 |
| EBV | BZLF1 | 196–204 | LLQHYREVA (SEQ. ID NO.:30) | HLA-A*0201 | 111 |
| EBV | BZLFI | 217–225 | LLKQMCPSL (SEQ. ID NO.:31) | HLA-A*O201 | 111 |
| EBV | BZLF1 | 229–237 | SIIPRTPDV (SEQ. ID NO.:32) | HLA-A*0201 | 111 |
| EBV | EBNA-6 | 284–293 | LLDFVRFMGV (SEQ. ID NO.:33) | HLA-A*0201 | 112 |
| EBV | EBNA-3 | 464–472 | SVRDRLARL (SEQ. ID NO.:34) | HLA-A*0203 | 113 |
| EBV | EBNA-4 | 416–424 | IVTDFSVIK (SEQ. ID NO.:35) | HLA-A*1101 | 114, 115 |
| EBV | EBNA-4 | 399–408 | AVFDRKSDAK (SEQ. ID NO.:36) | HLA-A*0201 | 116 |
| EBV | EBNA-3 | 246–253 | RYSIFFDY (SEQ. ID NO.:37) | HLA-A24 | 113 |
| EBV | EBNA-6 | 881–889 | QPRAPIRPI (SEQ. ID NO.:38) | HLA-B7 | 117 |
| EBV | EBNA-3 | 379–387 | RPPIFIRRI. (SEQ. ID NO.:39) | HLA-B7 | 117 |
| EBV | EBNA-1 | 426–434 | EPDVPPGAI (SEQ. ID NO.:40) | HLA-B7 | 111 |
| EBV | EBNA-1 | 228–236 | IPQCRLTPL (SEQ. ID NO.:41) | HLA-B7 | 111 |
| EBV | EBNA-1 | 546–554 | GPGPQPGPL (SEQ. ID NO.:42) | HLA-B7 | 111 |
| EBV | EBNA-1 | 550–558 | QPGPLRESI (SEQ. ID NO.:43) | HLA-B7 | 111 |
| EBV | EBNA-1 | 72–80 | R.PQKR1PSCI (SEQ. ID NO.:44) | HLA-B7 | 111 |
| EBV | EBNA-2 | 224–232 | PPTPLLTVL (SEQ. ID NO.:45) | HLA-B7 | 111 |
| EBV | EBNA-2 | 241–249 | TPSPPRMHL (SEQ. ID NO.:46) | HLA-B7 | 111 |
| EBV | EBNA-2 | 244–252 | PPRMHLPVL (SEQ. ID NO.:47) | HLA-B7 | 111 |
| EBV | EBNA-2 | 254–262 | VPDQSMHPL (SEQ. ID NO.:48) | HLA-B7 | 111 |
| EBV | EBNA-2 | 446–454 | PPSIDPADL (SEQ. ID NO.:49) | HLA-B7 | 111 |
| EBV | BZLFI | 44–52 | LPCVLWPVL (SEQ. ID NO.:50) | HLA-B7 | 111 |
| EBV | BZLF1 | 222–231 | CPSLDVDSII (SEQ. ID NO.:51) | HLA-B7 | 111 |
| EBV | BZLFI | 234–242 | TPDVLHEDL (SEQ. ID NO.:52) | HLA-B7 | 111 |
| EBV | EBNA-3 | 339–347 | FLRGRAYGL (SEQ. ID NO.:53) | HLA-B8 | 118 |
| EBV | EBNA-3 | 26–34 | QAKWRLQTL (SEQ. ID NO.:54) | HLA-B8 | 113 |
| EBV | EBNA-3 | 325–333 | AYPLHEQHG (SEQ. ID NO.:55) | HLA-B8 | 116 |
| EBV | EBNA-3 | 158–166 | Y1KSFVSDA (SEQ. ID NO.:56) | HLA-B8 | 116 |
| EBV | LMP-2 | 236–244 | RRRWRRLTV (SEQ. ID NO.:57) | HLA-B*2704 | 119 |
| EBV | EBNA-6 | 258–266 | RRIYDLIEL (SEQ. ID NO.:58) | HLA-B*2705 | 119 |
| EBV | EBNA-3 | 458–466 | YPLHEQHGM (SEQ. ID NO.:59) | HLA-B*3501 | 120 |
| EBV | EBNA-3 | 458–466 | YPLHEQHGM (SEQ. ID NO.:59) | HLA-B*3503 | 113 |
| HCV | NS3 | 389–397 | HSKKKCDEL (SEQ. ID NO.:60) | HLA-B8 | 145 |
| HCV | env E | 44–51 | ASRCWVAM (SEQ. ID NO.:61) | HLA-B*3501 | 146 |
| HCV | core protein | 27–35 | GQIVGGVYL (SEQ. ID NO.:62) | HLA-B*40012 | 147 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| HCV | NSI | 77–85 | PPLTDFDQGW (SEQ. ID NO.:63) | HLA-B*5301 | 145 |
| HCV | core protein | 18–27 | LMGYIPLVGA (SEQ. ID NO.:64) | H2-Dd | 138 |
| HCV | core protein | 16–25 | ADLMGYIPLV (SEQ. ID NO.:65) | H2-Dd | 148 |
| HCV | NS5 | 409–424 | MSYSWTGALVTPC AEE (SEQ. ID NO.:66) | H2-Dd | 149 |
| HCV | NSI | 205–213 | KHPDATYSR (SEQ. ID NO.:67) | Papa-A06 | 150 |
| HCV-1 | NS3 | 400–409 | KLVALGINAV (SEQ. ID NO.:68) | HLA-A*0201 | 141 |
| HCV-1 | NS3 | 440–448 | GDFDSVIDC (SEQ. ID NO.:69) | Patr-B16 | 151 |
| HCV-1 | env E | 118–126 | GNASRCWVA (SEQ. ID NO.:70) | Patr-B16 | 151 |
| HCV-1 | NSI | 159–167 | TRPPLGNWF (SEQ. ID NO.:71) | Patr-B13 | 151 |
| HCV-1 | NS3 | 351–359 | VPHPNIEEV (SEQ. ID NO.:72) | Patr-B13 | 151 |
| HCV-1 | NS3 | 438–446 | YTGDFDSVI (SEQ. ID NO.:73) | Patr-B01 | 151 |
| HCV-1 | NS4 | 328–335 | SWAIKWEY (SEQ. ID NO.:74) | Patr-A11 | 151 |
| HCV-1 | NSI | 205–213 | KHPDATYSR (SEQ. ID NO.:75) | Patr-A04 | 150 |
| HCV-1 | NS3 | 440–448 | GDFDSVIDC (SEQ. ID NO.:76) | Patr-A04 | 150 |
| HIV | gp41 | 583–591 | RYLKDQQLL (SEQ. ID NO.:77) | HLA_A24 | 152 |
| HIV | gagp24 | 267–275 | IVGLNKIVR (SEQ. ID NO.:78) | HLA-A*3302 | 153, 154 |
| HIV | gagp24 | 262–270 | EIYKRWII1 (SEQ. ID NO.:79) | HLA-B8 | 155, 156 |
| HIV | gagp24 | 261–269 | GE1YKRWIL (SEQ. ID NO.:80) | HLA-B8 | 155, 156 |
| HIV | gagp17 | 93–101 | EIKDTKEAL (SEQ. ID NO.:81) | HLA-B8 | 155, 157 |
| HIV | gp41 | 586–593 | YLKDQQLL (SEQ. ID NO.:82) | HLA-B8 | 158 |
| HIV | gagp24 | 267–277 | ILGLNKIVRMY (SEQ. ID NO.:83) | HLA-B*1501 | 153 |
| HIV | gp41 | 584–592 | ERYLKDQQL (SEQ. ID NO.:84) | HLA-B14 | 158 |
| HIV | nef | 115–125 | YHTQGYFPQWQ (SEQ. ID NO.:85) | HLA-B17 | 159 |
| HIV | nef | 117–128 | TQGYFPQWQNYT (SEQ. ID NO.:86) | HLA-817 | 159 |
| HIV | gp120 | 314–322 | GRAFVT1GK (SEQ. ID NO.:87) | HLA-B*2705 | 160, 184 |
| HIV | gagp24 | 263–271 | KRWIILGLN (SEQ. ID NO.:88) | HLA-B*27O2 | 161 |
| HIV | nef | 72–82 | QVPLRPMTYK (SEQ. ID NO.:89) | HLA-B*3501 | 159 |
| HIV | nef | 117–125 | TQGYFPQWQ (SEQ. ID NO.:90) | HLA-B*3701 | 159 |
| HIV | gagp24 | 143–151 | HQAISPRTI, (SEQ. ID NO.:91) | HLA-Cw*0301 | 162 |
| HIV | gagp24 | 140–151 | QMVHQAISPRTL (SEQ. ID NO.:92) | HLA-Cw*0301 | 162 |
| HIV | gp120 | 431–440 | MYAPPIGGQI (SEQ. ID NO.:93) | H2-Kd | 163 |
| HIV | gp160 | 318–327 | RGPGRAFVTI (SEQ. ID NO.:94) | H2-Dd | 164, 165 |
| HIV | gp120 | 17–29 | MPGRAFVTI (SEQ. ID NO.:95) | H2-Ld | 166, 167 |
| HIV-1 | RT | 476–484 | ILKEPVHGV (SEQ. ID NO.:96) | HLA-A*0201 | 168, 169 |
| HIV-1 | nef | 190–198 | AFHHVAREL (SEQ. ID NO.:97) | HLA-A*0201 | 170 |
| HIV-1 | gpI60 | 120–128 | KLTPLCVTL (SEQ. ID NO.:98) | HLA-A*0201 | 171 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| HIV-1 | gp]60 | 814–823 | SLLNATDIAV (SEQ. ID NO.:99) | HLA-A*0201 | 171 |
| HIV-1 | RT | 179–87 | VIYQYMDDL (SEQ. ID NO.:100) | HLA-A*0201 | 172 |
| HIV-1 | gagp 17 | 77–85 | SLYNTVATL (SEQ. ID NO.:101) | HLA-A*0201 | 173 |
| HIV-1 | gp160 | 315–329 | RGPGRAFVT1 (SEQ. ID NO.:102) | HLA-A*0201 | 174 |
| HIV-1 | gp41 | 768–778 | RLRDLLLIVTR (SEQ. ID NO.:103) | HLA-A3 | 175, 178 |
| HIV-1 | nef | 73–82 | QVPLRPMTYK (SEQ. ID NO.:104) | HLA-A3 | 176 |
| HIV-1 | gp120 | 36–45 | TVYYGVPVWK (SEQ. ID NO.:105) | HLA-A3 | 177 |
| HIV-1 | gagp 17 | 20–29 | RLRPGGKKK (SEQ. ID NO.:106) | HLA-A3 | 177 |
| HIV-1 | gp120 | 38–46 | VYYGVPVWK (SEQ. ID NO.:107) | HLA-A3 | 179 |
| HIV-1 | nef | 74–82 | VPLRPMTYK (SEQ. ID NO.:108) | HLA-a*1101 | 114 |
| HIV-1 | gagp24 | 325–333 | AIFQSSMTK (SEQ. ID NO.:109) | HLA-A*1101 | 114 |
| HIV-1 | nef | 73–82 | QVPLRPMTYK (SEQ. ID NO.:104) | HLA-A*1101 | 180 |
| HIV-1 | nef | 83–94 | AAVDLSHFLKEK (SEQ. ID NO.:110) | HLA-A*1101 | 159 |
| HIV-1 | gagp24 | 349–359 | ACQGVGGPGGHK (SEQ. ID NO.:111) | HLA-A*1101 | 181 |
| HIV-1 | gagp24 | 203–212 | ETINEEAAEW (SEQ. ID NO.:112) | HLA-A25 | 182 |
| HIV-1 | nef | 128–137 | TPGPGVRYPL (SEQ. ID NO.:113) | HLA-B7 | 159 |
| HIV-1 | gagp 17 | 24–31 | GGKKKYKL (SEQ. ID NO.:114) | HLA-B8 | 183 |
| HIV-1 | gp120 | 2–10 | RVKEKYQHL (SEQ. ID NO.:115) | HLA-B8 | 181 |
| HIV-1 | gagp24 | 298–306 | DRFYKTLRA (SEQ. ID NO.:116) | HLA-B14 | 173 |
| HIV-1 | NEF | 132–147 | GVRYPLTFGWGYKLVP (SEQ. ID NO.:117) | HLA-B18 | 159 |
| HIV-1 | gagp24 | 265–24 | KRWIILGLNK (SEQ. ID NO.:118) | HLA-B*2705 | 184, 153 |
| HIV-1 | nef | 190–198 | AFHHVAREL (SEQ. ID NO.:97) | HLA-B*5201 | 170 |
| EBV | EBNA-6 | 335–343 | KEHVIQNAF (SEQ. ID NO.:119) | HLA-B44 | 121 |
| EBV | EBNA-6 | 130–139 | EENLLDFVRF (SEQ. ID NO.:120) | HLA-B*4403 | 122 |
| EBV | EBNA-2 | 42–51 | DTPLIPLTIF (SEQ. ID NO.:121) | HLA-B51 | 121 |
| EBV | EBNA-6 | 213–222 | QNGALAINTF (SEQ. ID NO.:122) | HLA-1362 | 112 |
| EBV | EBNA-3 | 603–611 | RLRAEAGVK (SEQ. ID NO.:123) | HLA-A3 | 123 |
| HIV | sAg | 348–357 | GLSPTVWLSV (SEQ. ID NO.:124) | HLA-A*0201 | 124 |
| HBV | SAg | 335–343 | WLSLLVPFV (SEQ. ID NO.:125) | HLA-A*0201 | 124 |
| HBV | cAg | 18–27 | FLPSDFFPSV (SEQ. ID NO.:126) | HLA-A*0201 | 125, 126, 127 |
| HBV | cAg | 18–27 | FLPSDFFPSV (SEQ.ID NO.:126) | HLA-A*0202 | 127 |
| HBV | cAg | 18–27 | FLPSDFFPSV (SEQ. ID NO.:126) | HLA-A*0205 | 127 |
| HBV | cAg | 18–27 | FLPSDFFPSV (SEQ. ID NO.:126) | HLA-A*0206 | 127 |
| HBV | pol | 575–583 | FLLSLGIHL (SEQ. ID. NO.: 127) | HLA-A*0201 | 128 |
| HBV | pol | 816–824 | SLYADSPSV (SEQ. ID. NO.: 128) | HLA-A*0201 | 128 |
| HBV | pol | 455–463 | GLSRYVARL (SEQ. ID. NO.: 129) | HLA-A*0201 | 128 |
| HBV | env | 338–347 | LLVPFVQWFV (SEQ. ID. NO.: 130) | HLA-A*0201 | 129 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| HBV | env | 642–650 | ALMPLYACI (SEQ. ID. NO.: 131) | HLA-A*0201 | 129 |
| HBV | env | 378–387 | LLPIFFCLWV (SEQ. ID. NO.: 132) | HLA-A*0201 | 129 |
| HBV | pol | 538–546 | YMDDVVLGA (SEQ. ID. NO.: 133) | HLA-A*0201 | 129 |
| HBV | env | 250–258 | LLLCLIFLL (SEQ. ID. NO.: 134) | HLA-A*0201 | 130 |
| HBV | env | 260–269 | LLDYQGMLPV (SEQ. ID. NO.: 135) | HLA-A*0201 | 130 |
| HBV | env | 370–379 | SIVSPFIPLL (SEQ. ID. NO.: 136) | HLA-A*0201 | 130 |
| HBV | env | 183–191 | FLLTRILTI (SEQ. ID. NO.: 137) | HLA-A*0201 | 130 |
| HBV | cAg | 88–96 | YVNVNMGLK (SEQ. ID. NO.: 138) | HLA-A*1101 | 131 |
| HBV | cAg | 141–151 | STLPETTVVRR (SEQ. ID. NO.: 139) | HLA-A*3101 | 132 |
| HBV | cAg | 141–151 | STLPETTVVRR (SEQ. ID. NO.: 139) | HLA-A*6801 | 132 |
| HBV | cAg | 18–27 | FLPSDFFPSV (SEQ. ID. NO.: 126) | HLA-A*6801 | 127 |
| HBV | sAg | 28–39 | IPQSLDSWWTSL (SEQ. ID. NO.: 140) | H2-Ld | 133 |
| HBV | cAg | 93–100 | MGLKFRQL (SEQ. ID. NO.: 141) | H2-Kb | 134 |
| HBV | preS | 141–149 | STBXQSGXQ (SEQ. ID. NO.: 142) | HLA-A*0201 | 135 |
| HCMV | gp B | 618–628 | FLAGNSAYEYV (SEQ. ID. NO.: 143) | HLA-A*0201 | 124 |
| HCMV | E1 | 978–989 | SDEEFAIVAYTL (SEQ. ID. NO.: 144) | HLA-B18 | 136 |
| HCMV | pp65 | 397–411 | DDVWTSGSDSDEELV (SEQ. ID. NO.: 145) | HLA-b35 | 137 |
| HCMV | pp65 | 123–131 | IPSINVHHY (SEQ. ID. NO.: 146) | HLA-B*3501 | 136 |
| HCMV | pp65 | 495–504 | NLVPMVATVO (SEQ. ID. NO.: 147) | HLA-A*0201 | 137 |
| HCMV | pp65 | 415–429 | RKTPRVTOGGAMA (SEQ. ID. NO.: 148) | HLA-B7 | 137 |
| HCV | MP | 17–25 | DLMGYIPLV (SEQ. ID. NO.: 149) | HLA-A*0201 | 138 |
| HCV | MP | 63–72 | LLALLSCLTV (SEQ. ID. NO.: 150) | HLA-A*0201 | 139 |
| HCV | MP | 105–112 | ILHTPGCV (SEQ. ID NO.:151) | HLA-A*0201 | 139 |
| HCV | env E | 66–75 | QLRRHIDLLV (SEQ. ID NO.:152) | HLA-A*0201 | 139 |
| HCV | env E | 88–96 | DLCGSVFLV (SEQ. ID NO.:153) | HLA-A*0201 | 139 |
| HCV | env E | 172–180 | SMVGNWAKV (SEQ. ID NO.:154) | HLA-A*0201 | 139 |
| HCV | NSI | 308–316 | HLIIQNIVDV (SEQ. ID NO.:155) | HLA-A*0201 | 139 |
| HCV | NSI | 340–348 | FLLLADARV (SEQ. ID NO.:156) | HLA-A*0201 | 139 |
| HCV | NS2 | 234–246 | GLRDLAVAVEPVV (SEQ. ID NO.:157) | HLA-A*0201 | 139 |
| HCV | NSI | 18–28 | SLLAPGAKQNV (SEQ. ID NO.:158) | HLA-A*0201 | 139 |
| HCV | NSI | 19–28 | LLAPGAKQNV (SEQ. ID NO.:159) | HLA-A*0201 | 139 |
| HCV | NS4 | 192–201 | LLFNILGGWV (SEQ. ID NO.:160) | HLA-A*0201 | 129 |
| HCV | NS3 | 579–587 | YLVAYQATV (SEQ. ID NO.:161) | HLA-A*0201 | 129 |
| HCV | core protein | 34–43 | YLLPRRGPRL (SEQ. ID NO.:162) | HLA-A*0201 | 129 |
| HCV | MP | 63–72 | LLALLSCLTI (SEQ. ID NO.:163) | HLA-A*0201 | 129 |
| HCV | NS4 | 174–182 | SLMAFTAAV (SEQ. ID NO.:164) | HLA-A*0201 | 140 |
| HCV | NS3 | 67–75 | CINGVCWTV (SEQ. ID NO.:165) | HLA-A*0201 | 140 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| HCV | NS3 | 163–171 | LLCPAGHAV (SEQ.ID NO.:166) | HLA-A*0201 | 141 |
| HCV | NS5 | 239–247 | ILDSFDPLV (SEQ. ID NO.:167) | HLA-A*0201 | 141 |
| HCV | NS4A | 236–244 | ILAGYGAGV (SEQ. ID NO.:168) | HLA-A*0201 | 142 |
| HCV | NS5 | 714–722 | GLQDCTMLV (SEQ. ID NO.:169) | HLA-A*0201 | 142 |
| HCV | NS3 | 281–290 | TGAPVTYSTY (SEQ. ID NO.:170) | HLA-A*0201 | 143 |
| HCV | NS4A | 149–157 | HMWNFISGI (SEQ. ID NO.:171) | HLA-A*0201 | 144 |
| HCV | NS5 | 575–583 | RVCEKMALY (SEQ. ID NO.:172) | HLA-A*0201-A3 | 145 |
| HCV | NS1 | 238–246 | TINYTIFK (SEQ. ID NO.:173) | HLA-A*1101 | 145 |
| HCV | NS2 | 109–116 | YISWCLWW (SEQ. ID NO.:174) | HLA-A23 | 145 |
| HCV | core protein | 40–48 | GPRLGVRAT (SEQ.ID NO.:175) | HLA-B7 | 145 |
| HIV-1 | gp120 | 380–388 | SFNCGGEFF (SEQ.ID NO.:176) | HLA-Cw*0401 | 185 |
| HIV-1 | RT | 206–214 | TEMEKEGKI | H2-Kk | 186 |
| HIV-1 | p17 | 18–26 | KIRLRPGGK (SEQ. ID NO.:178) | HLA-A*0301 | 187 |
| HIV-1 | P17 | 20–29 | RLRPGGKKKY (SEQ. ID NO.:179) | HLA-A*0301 | 188 |
| HIV-1 | RT | 325–333 | AIFQSSMTK (SEQ..LD NO.:180) | HLA-A*0301 | 188 |
| HIV-1 | p17 | 84–92 | TLYCVHQRI (SEQ. ID NO.:181) | HLA-A11 | 188 |
| HIV-1 | RT | 508–517 | IYQEPFKNLK (SEQ. ID NO.:182) | HLA-A11 | 188 |
| HIV-1 | p17 | 28–36 | KYKLKHIVW (SEQ. ID NO.:183) | HLA-A24 | 188 |
| HIV-1 | gp120 | 53–62 | LFCASDAKAY (SEQ. ID NO.:184) | HLA-A24 | 189 |
| HIV-1 | gagp24 | 145–155 | QAISPRTLNAW (SEQ. ID NO.:185) | HLA-A25 | 188 |
| HIV-1 | gagp24 | 167–175 | EVIPMFSAL (SEQ. ID NO.:186) | HLA-A26 | 188 |
| HIV-1 | RT | 593–603 | ETFYVDGAANR (SEQ. ID NO.:187) | HLA-A26 | 188 |
| HIV-1 | gp41 | 775–785 | RLRDLLLIVTR (SEQ.ID NO.:188) | HLA-A31 | 190 |
| HIV-1 | RT | 559–568 | PIQKETWETW (SEQ. ID NO.:189) | HLA-A32 | 187 |
| HIV-1 | gp120 | 419–427 | RIKQIINMW (SEQ.ID NO.:190) | HLA-A32 | 187 |
| HIV-1 | RT | 71–79 | ITLWQRPLV (SEQ.ID NO.:191) | HLA-A*6802 | 188 |
| HIV-1 | RT | 85–93 | DTVLEEMNL (SEQ. ID NO.:192) | HLA-A*6802 | 188 |
| HIV-1 | RT | 71–79 | ITLWQRPLV (SEQ.ID NO.:193) | HLA-A*7401 | 188 |
| HIV-1 | gagp24 | 148–156 | SPRTLNAWV (SEQ. ID NO.:194) | HLA-B7 | 188 |
| HIV-1 | gagp24 | 179–187 | ATPQDLNTM (SEQ. ID NO.:195) | HLA-B7 | 188 |
| HIV-1 | gp120 | 303–312 | RPNNNTRKSI (SEQ. ID NO.:196) | HLA-B7 | 188 |
| HIV-1 | gp41 | 843–851 | IPRRIRQGL (SEQ.ID NO.:197) | HLA-B7 | 188 |
| HIV-1 | p17 | 74–82 | ELRSLYNTV (SEQ. ID NO.:198) | HLA-B8 | 188 |
| HIV-1 | nef | 13–20 | WPTVRERM (SEQ. ID NO.:199) | HLA-B8 | 188 |
| HIV-1 | nef | 90–97 | FLKEKGGL (SEQ. ID NO.:200) | HLA-B8 | 188 |
| HIV-1 | gag p24 | 183–191 | DLNTMLNTV (SEQ. ID NO.:568) | HLA-B14 | 191 |
| HIV-1 | P17 | 18–27 | KIRLRPGGKK (SEQ. ID NO.:201) | HLA-B27 | 188 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| HIV-1 | p17 | 19–27 | IRLRPGGKK (SEQ. ID NO.:202) | HLA-B27 | 188 |
| HIV-1 | gp41 | 791–799 | GRRGWEALKY (SEQ. ID NO.:203) | HLA-B27 | 188 |
| HIV-1 | nef | 73–82 | QVPLRPMTYK (SEQ. ID NO.:204) | HLA-B27 | 188 |
| HIV-1 | GP41 | 590–597 | RYLKDQQL (SEQ. ID NO.:205) | HLA-B27 | 192 |
| HIV-1 | nef | 105–114 | RRQDILDLWI (SEQ. ID NO.:206) | HLA-B*2705 | 188 |
| HIV-1 | nef | 134–141 | RYPLTFGW (SEQ. ID NO.:207) | HLA-B*2705 | 188 |
| HIV-1 | p17 | 36–44 | WASRELERF (SEQ. ID NO.:208) | HLA-B35 | 188 |
| HIV-1 | GAG P24 | 262–270 | TVLDVGDAY (SEQ. ID NO.:209) | HLA-B35 | 188 |
| HIV-1 | gp120 | 42–52 | VPVWKEATTTL (SEQ. ID NO.:210) | HLA-B35 | 188 |
| HIV-1 | P17 | 36–44 | NSSKVSQNY (SEQ. ID NO.:221) | HLA-B35 | 193 |
| HIV-1 | gag p24 | 254–262 | PPIPVGDIY (SEQ. ID NO.:212) | HLA-B35 | 193 |
| HIV-1 | RT | 342–350 | HPDIVIYQY (SEQ. ID NO.:213) | HLA-B35 | 193 |
| HIV-1 | gp41 | 611–619 | TAVPWNASW (SEQ. ID NO.:214) | HLA-B35 | 194 |
| HIV-1 | gag | 245–253 | NPVPVGN1Y (SEQ. ID NO.:215) | HLA-B35 | 193 |
| HIV-1 | nef | 120–128 | YFPDWQNYT (SEQ. ID NO.:216) | HLA-B37 | 188 |
| HIV-1 | gag p24 | 193–201 | GHQAAMQML (SEQ. ID NO.:217) | HLA-B42 | 188 |
| HIV-1 | p17 | 20–29 | RLRPGGKKIKY (SEQ. ID NO.:218) | HLA-B42 | 188 |
| Thy-1 | RT | 438–446 | YPGIKVRQL (SEQ. ID NO.:219) | HLA-B42 | 188 |
| HIV-1 | RT | 591–600 | GAETFYVDGA (SEQ. ID NO.:220) | HLA-B45 | 188 |
| HIV-1 | gag p24 | 325–333 | NANPDCKTI (SEQ. ID NO.:221) | HLA-B51 | 188 |
| HIV-1 | gag p24 | 275–282 | RMYSPTSI (SEQ. ID NO.:222) | HLA-B52 | 188 |
| HIV-1 | gp120 | 42–51 | VPVWKEAT™IT (SEQ. ID NO.:223) | HLA-B*5501 | 192 |
| HIV-1 | gag p24 | 147–155 | ISPRTLNAW (SEQ. ID NO.:224) | HLA-B57 | 188 |
| HIV-1 | gag p24 | 240–249 | TSTLQEQIGW (SEQ. ID NO.:225) | HLA-B57 | 188 |
| HIV-1 | gag p24 | 162–172 | KAFSPEVIPMF (SEQ. ID NO.:226) | HLA-B57 | 188 |
| HIV-1 | gagp24 | 311–319 | QASQEVKNW (SEQ. ID NO.:227) | HLA-B57 | 188 |
| H1V-1 | gagp24 | 311–319 | QASQDVKNW (SEQ. ID NO.:228) | HLA-B57 | 188 |
| HIV-1 | nef | 116–125 | HTQGYFPDWQ (SEQ. ID NO.:229) | HLA-B57 | 188 |
| HIV-1 | nef | 120–128 | YFPDWQNYT (SEQ. ID NO.:230) | HLA-B57 | 188 |
| HIV-1 | gag p24 | 240–249 | TSTLQEQIGW (SEQ. ID NO.:231) | HLA-B58 | 188 |
| HIV-1 | p17 | 20–29 | RLRPGGKKKY (SEQ. ID NO.:232) | HLA-B62 | 188 |
| HIV-1 | p24 | 268–277 | LGLNKJVRMY (SEQ. ID NO.:233) | HLA-B62 | 188 |
| HIV-1 | RT | 415–426 | LVGKLNWASQIY (SEQ. ID NO.:234) | HLA-B62 | 188 |
| HIV-1 | RT | 476–485 | ILKEPVHGVY (SEQ. ID NO.:235) | HLA-B62 | 188 |
| HIV-1 | nef | 117–127 | TQGYFPDWQNY (SEQ. ID NO.:236) | HLA-B62 | 188 |
| HIV-1 | nef | 84–91 | AVDLSHFL (SEQ. ID NO.:237) | HLA-B62 | 188 |
| HIV-1 | gag p24 | 168–175 | VIPMFSAL (SEQ. ID NO.:238) | HLA-Cw*0102 | 188 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| HIV-1 | gp120 | 376–384 | FNCGGEFFY (SEQ. ID NO.:239) | HLA-A29 | 196 |
| HIV-1 | gp120 | 375–383 | SFNCGGEFF (SEQ. ID NO.:240) | HLA-B15 | 196 |
| HIV-1 | nef | 136–145 | PLTFGWCYKL (SEQ. ID NO.:241) | HLA-A*0201 | 197 |
| HIV-1 | nef | 180–189 | VLEWRFDSRL (SEQ. ID NO.:242) | HLA-A*0201 | 197 |
| HIV-1 | nef | 68–77 | FPVTPQVPLR (SEQ. ID NO.:243) | HLA-B7 | 197 |
| HIV-1 | nef | 128–137 | TPGPGVRYPL (SEQ. ID NO.:244) | HLA-B7 | 197 |
| HIV-1 | gag p24 | 308–316 | QASQEVKNW (SEQ. ID NO.:245) | HLA-Cw*0401 | 521 |
| HIV-1 IIIB | RT | 273–282 | VPLDEDFRKY (SEQ. ID NO.:246) | HLA-B35 | 181 |
| HIV-1 IIIB | RT | 25–33 | NPDIVIYQY (SEQ. ID NO.:247) | HLA-B35 | 181 |
| HIV-1 IIIB | gp41 | 557–565 | RAIEAQAHL (SEQ. ID NO.:248) | HLA-B51 | 181 |
| HIV-1 IIIB | RT | 231–238 | TAFTIPSI (SEQ. ID NO.:249) | HLA-B51 | 181 |
| HIV-1 IIIB | p24 | 215–223 | VHPVHAGPIA (SEQ. ID NO.:250) | HLA-B*5501 | 181 |
| HIV-1 IIIB | gp120 | 156–165 | NCSFNISTSI (SEQ. ID NO.:251) | HLA-Cw8 | 181 |
| HIV-1 IIIB | gp120 | 241–249 | CTNVSTVQC (SEQ. ID NO.:252) | HLA-Cw8 | 181 |
| HIV-1 5F2 | gp120 | 312–320 | IGPGRAFHT (SEQ. ID NO.:253) | H2-Dd | 198 |
| HIV-1 5F2 | pol | 25–33 | NPDIVIYQY (SEQ. ID NO.:254) | HLA-B*3501 | 199 |
| HIV-1 5F2 | pol | 432–441 | EPIVGAETFY (SEQ. ID NO.:255) | HLA-B*3501 | 199 |
| HIV-1 5F2 | pol | 432–440 | EPIVGAETF (SEQ. ID NO.:256) | HLA-B*3501 | 199 |
| HIV-1 5F2 | pol | 6–14 | SPAIFQSSM (SEQ. ID NO.:257) | HLA-B*3501 | 199 |
| HIV-1 5F2 | pol | 59–68 | VPLDKDFRKY (SEQ. ID NO.:258) | HLA-B*3501 | 199 |
| HIV-1 5F2 | pol | 6–14 | IPLTEEAEL (SEQ. ID NO.:259) | HLA-B*3501 | 199 |
| HIV-1 5F2 | nef | 69–79 | RPQVPLRPMTY (SEQ. ID NO.:260) | HLA-B*3501 | 199 |
| HIV-1 5F2 | nef | 66–74 | FPVRPQVPL (SEQ. ID NO.:261) | HLA-B*3501 | 199 |
| HIV-1 5F2 | env | 10–18 | DPNPQEVVL (SEQ. ID NO.:262) | HLA-B*3501 | 199 |
| HIV-1 5F2 | env | 7–15 | RPIVSTQLL (SEQ. ID NO.:263) | HLA-B*3501 | 199 |
| HIV-1 5F2 | pol | 6–14 | IPLTEEAEL (SEQ. ID NO.:264) | HLA-B51 | 199 |
| HIV-1 5F2 | env | 10–18 | DPNPQEVVL (SEQ. ID NO.:265) | HLA-B51 | 199 |
| HIV-1 5F2 | gagp24 | 199–207 | AMQMLKETI (SEQ. ID NO.:266) | H2-Kd | 198 |
| HIV-2 | gagp24 | 182–190 | TPYDrNQML (SEQ. ID NO.:267) | HLA-B*5301 | 200 |
| HIV-2 | gag | 260–269 | RRWIQLGLQKV (SEQ. ID NO.:268) | HLA-B*2703 | 188 |
| HIV-1 5F2 | gp41 | 593–607 | GIWGCSGKLICTIAV (SEQ. ID NO.:269) | HLA-B17 | 201 |
| HIV-1 5F2 | gp41 | 753–767 | ALIWEDLRSLCLFSY (SEQ. ID NO.:270) | HLA-B22 | 201 |
| HPV 6b | E7 | 21–30 | GLHCYEQLV (SEQ. ID NO.:271) | HLA-A*0201 | 202 |
| HPV 6b | E7 | 47–55 | PLKQHFQIV (SEQ. ID NO.:272) | HLA-A*0201 | 202 |
| HPV11 | E7 | 4–12 | RLVTLKDIV (SEQ. ID NO.:273) | HLA-A*0201 | 202 |
| HPV16 | E7 | 86–94 | TLGIVCPIC (SEQ. ID NO.:274) | HLA-A*0201 | 129 |
| HPV16 | E7 | 85–93 | GTLGIVCPI (SEQ. ID NO.:275) | HLA-A*0201 | 129 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| HPV16 | E7 | 12–20 | MLDLQPETI (SEQ. ID NO.:276) | HLA-A*0201 | 129 |
| HPV16 | E7 | 11–20 | YMLDLQPETT (SEQ. ID NO.:277) | HLA-A*0201 | 203 |
| HPV16 | E6 | 15–22 | RPRKLPQL (SEQ. ID NO.:278) | HLA-B7 | 204 |
| HPV16 | E6 | 49–57 | RAHYNIVTF (SEQ. ID NO.:279) | HW-Db | 205 |
| HSV | gp B | 498–505 | SSIEFARL (SEQ. ID NO.:280) | H2-Kb | 206 |
| HSV-1 | gp C | 480–488 | GIGIGVLAA (SEQ. ID NO.:281) | HLA-A*0201 | 104 |
| HSV-1 | ICP27 | 448–456 | DYATLGVGV (SEQ. ID NO.:282) | H2-Kd | 207 |
| HSV-1 | ICP27 | 322–332 | LYRTFAGNPRA (SEQ. ID NO.:283) | H2-Kd | 207 |
| HSV-1 | UL39 | 822–829 | QTFDFGRL (SEQ. ID NO.:284) | H2-Kb | 208 |
| HSV-2 | gpC | 446–454 | GAGIGVAVL (SEQ. ID NO.:285) | HLA-A*0201 | 104 |
| HLTV-1 | TAX | 11–19 | LLFGYPVYV (SEQ. ID NO.:286) | HLA-A*0201 | 209 |
| Influenza | MP | 58–66 | GILGFVFTL (SEQ. ID NO.:287) | HLA-A*0201 | 68, 169, 209, 210, 211 |
| Influenza | MP | 59–68 | ILGFVFTLTV (SEQ. ID NO.:288) | HLA-A*0201 | 168, 212, 213 |
| Influenza | NP | 265–273 | ILRGSVAHK (SEQ. ID NO.:289) | HLA-A3 | 214 |
| Influenza | NP | 91–99 | KTGGPIYKR (SEQ. ID NO.:290) | HLA-A*6801 | 215, 216 |
| Influenza | NP | 380–388 | ELRSRYWAI (SEQ. ID NO.:291) | HLA-B8 | 217 |
| Influenza | NP | 381–388 | LRSRYWAI (SEQ. ID NO.:292) | HLA-B*2702 | 218 |
| Influenza | NP | 339–347 | EDLRVLSFI (SEQ. ID NO.:293) | HLA-B*3701 | 219 |
| Influenza | NSI | 158–166 | GEISPLPSL (SEQ. ID NO.:294) | HLA-B44 | 220 |
| Influenza | NP | 338–346 | FEDLRVLSF (SEQ. ID NO.:295) | HLA-B44 | 220 |
| Influenza | NSI | 158–166 | GEISPLPSL (SEQ. ID NO.:294) | HLA-B*4402 | 220 |
| Influenza | NP | 338–346 | FEDLRVL5F (SEQ. ID NO.:295) | HLA-B*4402 | 220 |
| Influenza | PBI | 591–599 | VSDGGPKLY (SEQ. ID NO.:296) | HLA-Al | 214, 29 |
| Influenza A | NP | 44-52 | CTELKLSDY (SEQ. ID NO.:297) | HLA-Al 29 | |
| Influenza | NSI | 122–130 | AIMDKNIIL (SEQ. ID NO.:298) | HLA-A*0201 | 221 |
| Influenza A | NSI | 123-132 | IMDKNIILKA (SEQ. ID NO.:299) | HLA-A*0201 221 | |
| Influenza A | NP | 383-391 | SRYWAIRTR (SEQ. ID NO.:300) | HLA-B*2705 | 160, 184 |
| Influenza A | NP | 147-155 | TYQRTRALV (SEQ. ID NO.:301) | H2-Kd | 222, 223 |
| Influenza A | HA | 210-219 | TYVSVSTSTL (SEQ. ID NO.302) | H2-Kd | 224, 225 |
| Influenza A | HA | 518-526 | IYSTVASSL (SEQ. ID NO.:303) | H2-Kd | 224 |
| Influenza A | HA | 259-266 | FEANGNLI (SEQ. ID NO.:304) | H2-Kk | 226, 227, 228 |
| Influenza A | HA | 10-18 | IEGGWTGM1 (SEQ. ID NO.:305) | H2-Kk | 226, 227, 228 |
| Influenza A | NP | 50-57 | SDYEGRLI (SEQ. ID NO. 306) | H2-Kk | 229, 230 |
| Influenza a | NSI | 152-160 | EEGAIVGEI (SEQ. ID NO.:307) | H2-Kk | 231 |
| Influenza A34 | NP | 336–374 | ASNENMETM (SEQ. ID NO.:308) | H2Db | 168, 222, 219 |
| Influenza A68 | NP | 366–374 | ASNENMDAM (SEQ. ID NO.:309) | H2Db | 232 |
| Influenza B | NP | 85–94 | KLGEFYNQMM (SEQ. ID NO.:310) | HLA-A*0201 | 233 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| Influenza B | NP | 85–94 | KAGEFYNQMM (SEQ. ID NO.:311) | HLA-A*0201 | 234 |
| Influenza JAP | HA | 204–212 | LYQNVGTYV (SEQ. ID NO.312) | H2Kd | 235 |
| Influenza JAP | HA | 210–219 | TYVSVGTSTL (SEQ. ID NO.:313) | H2-Kd | 225 |
| Influenza JAP | HA | 523–531 | VYQILATYA (SEQ. ID NO.:314) | H2-Kd | 235 |
| Influenza JAP | HA | 529–537 | IYATVAGSL (SEQ. ID NO.:315) | H2-Kd | 235 |
| Influenza JAP | HA | 210–219 | TYVSVGTSTI(L > I) (SEQ. ID NO.:316) | H2-Kd | 236 |
| Influenza JAP | HA | 255–262 | FESTGNLI (SEQ. ID NO.:317) | H2-Kk | 237 |
| JHMV | cAg | 318–326 | APTAGAFFF (SEQ. ID NO.:318) | H2-Ld | 238 |
| LCMV | NP | 118–126 | RPQASGVYM (SEQ. ID NO.319) | H2-Ld | 239-240 |
| LCMV | NP | 396–404 | FQPQNGQFI (SEQ. ID NO.320) | H2-Db | 241 |
| LCMV | GP | 276–286 | SGVENPGGYCL (SEQ. ID NO.:321) | H2-Db | 242 |
| LCMV | GP | 33–42 | KAVYNFATCG (SEQ. ID NO.:322) | H2-Db | 243, 244 |
| MCMV | pp89 | 168–176 | YPHFMPTNL (SEQ. ID NO.:323) | H2-Ld | 245 |
| MHV | spike protein | 510–518 | CLSWNGPHL (SEQ. ID NO.324) | H2-Db | 248 |
| MMTV | env gp13 | 474–482 | SFAVATTAL (SEQ. ID NO.:325) | H2-Kd | 246 |
| MMTV | gag p27 | 425–433 | SYETFISRL (SEQ. ID NO.:326) | H2-Kd | 246 |
| MMTV | env gp73 | 544–551 | ANYDFICV (SEQ. ID NO.:327) | H2-Kb | 247 |
| MuLV | env p15E | 574–581 | KSPWFTTL (SEQ. ID NO.:328) | H2-Kb | 249, 250 |
| MuLV | env gp70 | 189–196 | SSWDFITV (SEQ. ID NO.:329) | H2-Kb | 251, Sijts et al. Submitted |
| MuLV | gag 75K | 75–83 | CCLCLTVFL (SEQ. ID NO.:330) | H2-Db | 252 |
| MuLV | env gp70 | 423–431 | SPSYVYHQF (SEQ. ID NO.:331) | H2Ld | 253 |
| MV | F protein | 437–447 | SRRYPDAVYLH (SEQ. ID NO.:332) | HLA-B*2705 | 254 |
| Mv | F protein | 438–446 | RRYPDAVYL (SEQ. ID NO.:333) | HLA-B*2705 | 255 |
| Mv | NP | 281–289 | YPALGLHEF (SEQ. ID NO.:334) | H2-Ld | 256 |
| Mv | HA | 343–351 | DPVIDRLYL (SEQ. ID NO.:335) | H2-Ld | 257 |
| MV | HA | 544–552 | SPGRSFSYF (SEQ. ID NO.:336) | H2-Ld | 257 |
| Poliovirus | VP1 | 111–118 | TYKDTVQL (SEQ. ID NO.:337) | H2-kd | 258 |
| Poliovirus | VP1 | 208–217 | FYDGFSKVPL (SEQ. ID NO.:338) | H2-Kd | 258 |
| Pseudorabies virus gp | G111 | 455-463 | IAGIGILAI (SEQ. ID NO.:339) | HLA-A*0201 | 104 |
| Rabiesvirus | NS | 197–205 | VEAEIAHQI (SEQ. ID NO.:340) | H2-Kk | 227-227 |
| Rotavirus | VP7 | 33–40 | IIYRELL1 (SEQ. ID NO.:341) | H2-Kb | 259 |
| Rotavirus | VP6 | 376–384 | VGPVFPPGM (SEQ. ID NO.:342) | 112-Kb | 260 |
| Rotavirus | VP3 | 585–593 | YSGYIFRDL (SEQ. ID NO.:343) | 112-Kb | 260 |
| RSV | M2 | 82–90 | SYIGSINNI (SEQ. ID NO.:344) | H2-Kd | 261 |
| SIV | gagp11C | 179–190 | EGCTPYDTNQML (SEQ. ID NO.:345) | Mamu-A*01 | 266 |
| SV | NP | 324–332 | FAPGNYPAL (SEQ. ID NO.:346) | H2-Db | 262 |
| SV | NP | 324–332 | FAPCTNYPAL (SEQ. ID NO.:346) | 112-Kb | 263, 264, 265 |

TABLE I-continued

Viral epitopes on MHC class 1 molecules

| Virus | Protein | AA Position | T cell epitope MHC ligand (Antigen) | MHC molecule | Ref. |
|---|---|---|---|---|---|
| SV40 | T | 404–411 | VVYDFLKC (SEQ. ID NO.:347) | 112-Kb | 267 |
| SV40 | T | 206–215 | SAINNYAQKL (SEQ. ID NO.:348) | H2-Db | 268, 269 |
| SV40 | T | 223–231 | CKGVNKEYL (SEQ. ID NO.349) | H2-Db | 268, 269 |
| SV40 | T | 489–497 | QGINNLDNL (SEQ. ID NO.:350) | H2-Db | 268, 269 |
| SV40 | T | 492–500 (501) | NNLDNLRDY(L) (SEQ. ID NO.:351) | H2-Db | 270 |
| SV40 | T | 560–568 | SEFLLEKRI (SEQ. ID NO.352) | H2-Kk | 271 |
| VSV | NP | 52–59 | RGYVYQGL (SEQ. ID NO.:353) | H2-Kb | 272 |

Table II sets forth antigens identified from various protein sources. The Table is extracted from Table 4.2 in the Rammensee book with the references in Table H being the same as the references in the Rammensee Table 4.2.

TABLE II

HLA Class I Motifs

| HLA-A1 | Position (Antigen) | Source | Ref. |
|---|---|---|---|
| T cell epitopes | EADPTGHSY (SEQ. ID NO.:354) | MAGE-1 161–169 | 27, 28 |
| | VSDGGPNLY (SEQ. ID NO.:355) | Influenza A PB 1591–599 | 21, 23 |
| | CTELKLSDY (SEQ. ID NO.:356) | Influenza A NP 44–52 | 23 |
| | EVDPIGHLY (SEQ. ID NO.:357) | MAGE-3 168–176 | 29, 30 |
| HLA-A201 | MLLSVPLLLG (SEQ. ID NO.:358) | Calreticulin signal sequence I-1q0 | 34, 35, 36, 37 |
| | STBXQSGXQ (SEQ. ID NO.:359) | HBV PRE-S PROTEIN 141–149 | 43 |
| | YMDGTMSQV (SEQ. ID NO.:360) | Tyrosinase 369–377 | 45 |
| | ILKEPVHGV (SEQ. ID NO.:361) | HIV-I RT 476–484 | 4, 31, 47 |
| | LLGFVFTLTV (SEQ. ID NO.:362) | Influenza MP 59–68 | 4, 39 |
| | LLFGYPVYVV (SEQ. ID NO.:363) | HTLV-1 tax 11–19 | 40 |
| | GLSPTVWLSV (SEQ. ID NO.:364) | HBV sAg 348–357 | 48 |
| | WLSLLVPFV (SEQ. ID NO.:365) (SEQ. ID NO.:366) | HBV sAg 335–343 | 49, 50, 51 |
| | CLG0LLTMV (SEQ. ID NO.:367) | EBVLMP-2 426–434 | 48 |
| | FLAGNSAYEYV (SEQ. ID NO.:368) | HCMV gp 618–628B | 53 |
| | KLGEFYNQMM (SEQ. ID NO.:369) | Influenza BNP 85–94 | 54 |
| | KLVALGINAV (SEQ. ID NO, :370) | HCV-1 N53 400–409 | 55 |
| | DLMGYIPLV (SEQ. ID NO.:371) | HCV MP 17–25 | 56 |
| | RLVTLKDIV (SEQ. ID NO.:372) | HPV 11 EZ 4–12 | 34, 35 |
| | MLLAVLYCL (SEQ. ID NO-373) | Tyrosinase 1–9 | 57, 58, 59, 68 |
| | AAGJGILTV (SEQ. ID NO.:374) | Melan A/Mart-127–35 | 60 |
| | YLEPGPVTA (SEQ. ID NO.:375) | Pmel 17/gp 100 480–488 | 61 |
| | ILDGTATLRL (SEQ. ID NO.:376) | Pmel 17/gp 100 457–466 | 62 |

TABLE II-continued

HLA Class I Motifs

| HLA-A1 | Position (Antigen) | Source | Ref. |
|---|---|---|---|
| | LLDGTATLRL (SEQ. IID NO.:377) | Pmel gp1OO 457–466 | 62 |
| | ITDQVPFSV (SEQ. ID NO.:378) | Pmel gp 100 209–217 | 62 |
| | KTWGQYWQV (SEQ. ID NO.:379) | Pmel gp 100 154–162 | 62 |
| | TITDQVPFSV (SEQ. ID NO.:380) | Pmel gp 100 208–217 | 62 |
| | AFHILVAREL (SEQ. ID NO.:381) | HIV-Inef 190–198 | 63 |
| | YLNKJQNSL (SEQ. ID NO.:382) | P. falciparum CSP 334–342 | 64 |
| | MMRKLAILSV (SEQ. ID NO.:383) | P. falciparum CSP 1–10 | 64 |
| | KAGEFYNQMM (SEQ. ID NO.:384) | Influenza BNP 85–94 | 65 |
| | NIAEGLRAL (SEQ. ID NO.:385) | EBNA-1 480–488 | 66 |
| | NLRRGTALA (SEQ. ID NO.:386) | EBNA-1 519–527 | 66 |
| | ALAIPQCRL (SEQ. ID NO.:387) | EBNA-1 525–533 | 66 |
| | VLKDATKDL (SEQ. ID NO.:388) | EBNA-1 575–582 | 66 |
| | FMVFLQTHI (SEQ. ID NO.:389) | EBNA-1 562–570 | 66 |
| | HLIVDTDSL (SEQ. ID NO.:390) | EBNA-2 15–23 | 66 |
| | SLGNPSLSV (SEQ. ID NO.391) | EBNA-2 22–30 | 66 |
| | PLASAMRML (SEQ. ID NO.392) | EBNA-2 126–134 | 66 |
| | RMLWMANYI (SEQ. ID NO.393) | EBNA-2 132–140 | 66 |
| | MLWMANYIV (SEQ. ID NO.394) | EBNA-2133–141 | 66 |
| | RPQGPQTA (SEQ. ID NO.395) | EBNA-2 151–159 | 66 |
| | PLRPTAPTTI (SEQ. ID NO.396) | EBNA-2 171–179 | 66 |
| | PLPPAThTV (SEQ. ID NO.397) | EBNA-2 205–213 | 66 |
| | RMHLPVLHV (SEQ. ID NO.398) | EBNA-2 246–254 | 66 |
| | PMPLPPSQL (SEQ. ID NO.399) | EBNA-2 287–295 | 66 |
| | QLPPPAAPA (SEQ. ID NO.:400) | EBNA-2 294–302 | 66 |

TABLE II-continued

HLA Class I Motifs

| HLA-A1 | Position (Antigen) | Source | Ref. |
|---|---|---|---|
| SMPELSPVL (SEQ. ID NO.:401) | EBNA-2 381–389 | | 66 |
| DLDESWDY1 (SEQ. ID NO.:402) | EBNA-2 453–461 | | 66 |
| PLPGVLWPVV (SEQ. ID NO.:403) | BZLF1 43–51 | | 66 |
| SLEECDSEL (SEQ. ID NO.:404) | BZLF1 167–175 | | 66 |
| EIKRYKNRV (SEQ. ID NO.:405) | BZLFI 176–184 | | 66 |
| QLLQFIYREV (SEQ. ID NO.:406) | BZLF1 195–203 | | 66 |
| LLQHYREVA (SEQ. ID NO.:407) | BZLFI 196–204 | | 66 |
| LLKQMCPSL (SEQ. ID NO.:408) | BZLF1 217–225 | | 66 |
| SIIPRTPDV (SEQ. ID NO.:409) | BZLFI 229–237 | | 66 |
| AIMDKNIIL (SEQ. ID NO.:410) | Influenza A NS1 122–130 | | 67 |
| IMDKNLILKA (SEQ. ID NO.411) | Influenza A NS1 123–132 | | 67 |
| LLALLSCLTV (SEQ. ID NO.:412) | HCV MP 63–72 | | 69 |
| ILHTPGCV (SEQ. ID NO.:413) | HCVMP 105–112 | | 69 |
| QLRRIIIDLLV (SEQ. ID NO.:414) | HCV env E 66–75 | | 69 |
| DLCGSVFLV (SEQ. ID NO.:415) | HCV env E 88–96 | | 69 |
| SMVGNWAKV (SEQ. ID NO.:416) | HCV env E 172–180 | | 69 |
| HLHQNIVDV (SEQ. ID NO.:417) | HCV NSI 308–316 | | 69 |
| FLLLADARV (SEQ. ID NO.:418) | HCV NSI 340–348 | | 69 |
| GLRDLAVAVEPVV (SEQ. ID NO.:419) | HCV NS2 234–246 | | 69 |
| SLLAPGAKQNV (SEQ. ID NO.:420) | HCV NS1 18–28 | | 69 |
| LLAPGAiKQNV (SEQ. ID NO.:421) | HCV NS1 19–28 | | 69 |
| FLLSLGIIIL (SEQ. ID NO.:422) | HBV pol 575–583 | | 70 |
| SLYADSPSV (SEQ. ID NO.:423) | HBV pol 816–824 | | 70 |
| GLSRYVARL (SEQ. ID NO.:424) | HIBV POL 455–463 | | 70 |
| KIFGSLAFL (SEQ. ID NO.:425) | HER-2 369–377 | | 71 |
| ELVSEFSRM (SEQ. ID NO.:426) | HER-2 971–979 | | 71 |
| KLTPLCVTL (SEQ. ID NO.:427) | HIV-I gp 160 120–128 | | 72 |
| SLLNATDIAV (SEQ. ID NO.:428) | HIV-I GP 160 814–823 | | 72 |
| VLYRYG5FSV (SEQ. ID NO.:429) | Pmel gp100 476–485 | | 62 |
| YIGEVLVSV (SEQ. ID NO.:430) | Non-filament forming class I myosin family (HA-2)** | | 73 |
| LLFNILGGWV (SEQ. ID NO.:431) | HCV NS4 192–201 | | 74 |
| LLVPFVQWFW (SEQ. ID NO.:432) | HBV env 338–347 | | 74 |
| ALMPLYACI (SEQ. ID NO.:433) | HBV pol 642–650 | | 74 |
| YLVAYQATV (SEQ. ID NO.:434) | HCV NS3 579–587 | | 74 |
| TLGIVCPIC (SEQ. ID NO.:435) | HIPV 16 E7 86–94 | | 74 |
| YLLPRRGPRL (SEQ. ID NO.:436) | HCV core protein 34–43 | | 74 |
| LLPIFFGLWV (SEQ. ID NO.:437) | HBV env 378–387 | | 74 |
| YMDDVVLGA (SEQ. ID NO.:438) | HBV Pol 53 8–546 | | 74 |
| GTLGIVCPI (SEQ. ID NO.:439) | HPV16 E7 85–93 | | 74 |
| LLALLSCLTI (SEQ. ID NO.:440) | HCY MP 63–72 | | 74 |
| MLDLQPETf (SEQ. ID NO.:441) | HPV 16 E7 12–20 | | 74 |
| SLMAFTAAV (SEQ. ID NO.:442) | HCV N54 174–182 | | 75 |
| C1NGVCWTV (SEQ. ID NO.:443) | HCV NS3 67–75 | | 75 |
| VIVINILLQYVV (SEQ. ID NO.:444) | Glutamic acid decarboxylase 114–123 | | 76 |
| ILTVILGVL (SEQ. ID NO.:445) | Melan A/Mart- 32–40 | | 77 |
| FLWGPRALV (SEQ. ID NO.:446) | MAGE-3 271–279 | | 78 |
| LLCPAGHAV (SEQ. ID NO.:447) | HCV NS3 163–171 | | 54 |
| ILD5FDPLV (SEQ. ID NO.:448) | HCV NSS 239–247 | | 54 |
| LLLCLIFLL (SEQ. ID NO.:449) | HBV env 250–258 | | 79 |
| LIDYQGMLPV (SEQ. ID NO.:450) | HBV env 260–269 | | 79 |
| SIVSPFIPLL (SEQ.ID NO.:451) | HBV env 370–379 | | 79 |
| FLLTRILTI (SEQ. ID NO.:452) | HBV env 183–191 | | 80 |
| HLGNVKYLV (SEQ. ID NO.:453) | P. faciparum TRAP 3–11 | | 81 |
| GIAGGLALL (SEQ. ID NO.:454) | P. faciparum TRAP 500–508 | | 81 |
| ILAGYGAGV (SEQ. ID NO.:455) | HCV NS 54A 23 6–244 | | 82 |
| GLQDCTMLV (SEQ. ID NO.:456) | HCV NS5 714–722 | | 82 |
| TGAPVTYSTY (SEQ. ID NO.:457) | HCV NS3 281–290 | | 83 |
| VIYQYMDDLV (SEQ. ID NO.:458) | HIV-1RT 179–187 | | 84 |
| VLPDVFIRCV (SEQ. ID NO.:459) | N-acetylglucosaminyl-transferase V Gnt-V intron | | 85 |
| VLPDVFIRC (SEQ. ID NO.:460) | N-acetylglucosaminyl-transferase V Gnt-V intron | | 85 |
| AVGIGIAVV (SEQ. ID NO.:461) | Human CD9 | | 86 |
| LVVLGLLAV (SEQ. ID NO.:462) | Human glutamyl-transferase | | 86 |
| ALGLGLLPV (SEQ. ID NO.:463) | Human G protein coupled receptor 164–172 | | 86 |
| GIGIGVLAA (SEQ. ID NO.:281) | HSV-I gp C 480–488 | | 86 |
| GAGIGVAVL (SEQ. ID NO.:464) | HSV-2 gp C 446–454 | | 86 |
| JAGIGILAI (SEQ. ID NO.:465) | Pseudorabies gpGIN 455–463 | | 86 |
| LIVIGILIL (SEQ. ID NO.:466) | Adenovirus 3 E3 9kD 30–38 | | 86 |
| LAGIGLIAA (SEQ. ID NO.:467) | S. Lincolnensis ImrA | | 86 |
| VDGIGILTI (SEQ. ID NO.:468) | Yeast ysa-1 77–85 | | 86 |
| GAGIGVLTA (SEQ. ID NO.:469) | B. polymyxa, 149–157 βcndox-ylanase | | 86 |

TABLE II-continued

HLA Class I Motifs

| HLA-A1 | Position (Antigen) | Source | Ref. |
|---|---|---|---|
| | AAGIGIIQI (SEQ. ID NO.:470) | E. coli methionine 590–598 synthase | 86 |
| | QAGIGILLA (SEQ. ID NO.:471) | E. coli hypothetical protein 4–12 | 86 |
| | KARDPHSGHFV (SEQ. ID NO.:472) | CDK4wl 22.32 | 87 |
| | KACDPI-ISGIIFV (SEQ. ID NO.:473) | CDK4-R24C 22–32 | 87 |
| | ACDPFISGHFV (SEQ. ID NO.:474) | GDK4-R24C 23–32 | 87 |
| | SLYNTVATL (SEQ. ID NO.:475) | HIV-I gag p 17 77–85 | 99 |
| | ELVSEFSRV (SEQ. ID NO.:476) | HER-2, m > V 971–979 substituted | 89 |
| | RGPGRAFVTI (SEQ. ID NO.:477) | HIV-I gp 160 315–329 | 90 |
| | HMWNFISGI (SEQ. ID NO.:478) | HCV NS4A 149–157 | 91 |
| | NLVPMVATVQ (SEQ. ID NO.:479) | HCMV pp65 495–504 | 92 |
| | GLHCYEQLV (SEQ. ID NO, :480) | HPV 6b E7 21–30 | 93 |
| | PLKQIJFQIV (SEQ. ID NO.:481) | HPV 6b E7 47–55 | 93 |
| | LLDFVRfMGV (SEQ. ID NO.:482) | EBNA-6 284–293 | 95 |
| | ATMEKNIML (SEQ. ID NO.:483) | Influenza Alaska NS 1 122–130 | 67 |
| | YLKTIQNSL (SEQ. ID NO.:484) | P. falciparum cp36 CSP | 96 |
| | YLNKIQNSL (SEQ. ID NO.:485) | P. falciparum cp39 CSP | 96 |
| | YMLDLQPE1T (SEQ. ID NO.:486) | HPV 16 E7 11–20* | 97 |
| | LLMGTLGIV (SEQ. ID NO.:487) | HPV16 E7 82–90** | 97 |
| | TLGIVCPI (SEQ. ID NO.:488) | HPV 16 E7 86-93 | 97 |
| | TLTSCNTSV (SEQ. ID NO.:489) | HIV-1 gp120 197–205 | 98 |
| | KLPQLCTEL (SEQ. ID NO.:490) | HPV 16 E6 18–26 | 97 |
| | THIDITLEG (SEQ. ID NO.:491) | HPV16 E6 29–37 | 97 |
| | LGIVCPICS (SEQ. ID NO.:492) | HPV16 E7 87–95 | 97 |
| | VILGVLLLI (SEQ. ID NO.:493) | Melan A/Mart-1 35–43 | 68 |
| | ALMDKSLHV (SEQ. ID NO.:494) | Melan A/Mart-1 56–64 | 68 |
| | GILTVILGV (SEQ. ID NO.:495) | Melan A/Mart-1 31–39 | 68 |
| T cell epitopes | M1NAYLDKL (SEQ. ID NO.:496) | P. Falciparum STARP 523–531 | 81 |
| | AAGIGILTV (SEQ. ID NO.:497) | Melan A/Mart- 127–35 | 100 |
| | FLPSDFFPSV (SEQ. ID NO, :498) | HBV cAg 18–27 | 51 |
| Motif unknown T cell epitopes | SVRDRLARL (SEQ. ID NO.:499) | EBNA-3 464–472 | 101 |
| T cell epitopes | AAGIGILTV (SEQ. ID NO.:497) | Melan A/Mart-1 27–35 | 100 |
| | FAYDGKDYI (SEQ. ID NO.:500) | Human MHC I-ot 140–148 | 99 |
| T cell epitopes | AAGIGILTV (SEQ. ID NO.:497) | Melan A/Mart-1 27–35 | 100 |
| | FLPSDFFPSV (SEQ. ID NO.:498) | HBV cAg 18–27 | 51 |
| Motif unknown T cell epitopes | AAGIGILTV (SEQ. ID NO.:497) | Meland A/Mart-1 27–35 | 100 |
| | FLPSDFFPSV (SEQ. ID NO.:498) | HBV cAg 18–27 | 51 |
| | AAGIGILTV | Melan A/Mart-1 27–35 | 100 |
| | ALLAVGATK (SEQ. ID NO.:501) | Pmell7 gp 100 17–25 | 107 |
| T cell epitopes | RLRDLLLIVTR (SEQ. ID NO.:502) | HIV-1 gp41 768–778 | 108 |
| | QVPLRPMTYK (SEQ. ID NO.:503) | HIV-1 nef 73–82 | 109 |
| | TVYYGVPVWK (SEQ. ID NO.:504) | HIV-1 gp120-36–45 | 110 |
| | RLRPGGKKK (SEQ. ID NO.:505) | HIV-1 gagp 17 20–29 | 110 |
| | ILRGSVAHK (SEQ. ID NO, :506) | Influenza NP 265–273 | 21 |
| | RLRAEAGVK (SEQ. ID NO.:507) | EBNA-3 603–611 | 111 |
| | RLRDLLLIVTR (SEQ. ID NO.:502) | HIV-1 gp41 770–780 | 112 |
| | VYYGVPVWK (SEQ. ID NO.:508) | HIV-I GP 120 38–46 | 113 |
| | RVCEKMALY (SEQ. ID NO.:509) | HCV N55 575–583 | 114 |
| Motif unknown T cell epitope | KIFSEVTLK (SEQ. ID NO.:510) | Unknown; muta melanoma peptide ted (p I 83L) 175–183 | Wolfel et al., pers. Comm. |
| T cell epitope | YVNVNMGLK* (SEQ. ID NO.:511) | HBV cAg 88–96 | 116 |
| T cell epitopes | IVTDFSVIK (SEQ. ID NO.:512) | EBNA-4 416–424 | 115, 117 |
| | ELNEALELK (SEQ. ID NO.:513) | P53 343–351 | 115 |
| | VPLRPMTYK (SEQ. ID NO.:514) | HIV-1 NEF 74–82 | 115 |
| | AIFQSSMTK (SEQ. ID NO.:515) | HIV-1 gag p24 325–333 | 115 |
| | QVPLRPMTXTK (SEQ. ID NO.:516) | HIV-1 nef 73–82 | 118 |
| | TTNYTIFKHCV (SEQ. ID NO.:517) | NSI 238–246 | 114 |
| | AAVDLSHFLKEK (SEQ. ID NO.:518) | HIV-1 nef 83–94 | 120 |
| | ACQGVGGPGGHK (SEQ. ID NO, :519) | HIV-1 II 1B p24 349–359 | 122 |
| HLA-A24 | SYLDSGIHF* (SEQ. TD NO.:520) | β-catenin, mutated (proto-onocogen) 29–37 | 123 |
| T cell epitopes | RYLKDQQLLHIV (SEQ. ID NO.:521) | GP 41 583–591 | 124 |
| | AYGLDFYIL (SEQ. ID NO.:522) | P15 melanoma Ag 10–18 | 125 |
| | AFLPWHIRLFL (SEQ. ID NO.:523) | Tyrosinase 206–215 | 126 |
| | AFLPWIHRLF (SEQ. ID NO.:524) | Tyrosinase 206–214 | 126 |
| | RYSIFFDY (SEQ. ID NO.:525) | Ebna-3 246–253 | 101 |
| T cell epitope | ETINEEAAEW (SEQ. ID NO.:526) | HIV-1 gag p24 203–212 | 127 |
| T cell epitopes | STLPETTVVRRHBV (SEQ. ID NO, :527) | cAg 141–151 | 129 |
| | MSLQRQFLR (SEQ. ID NO.:528) | ORF 3P-gp75 294–321 (bp) | 130 |
| | LLPGGRPYR (SEQ. ID NO.:528) | TRP (tyrosinase rel.) 197–205 | 131 |
| T cell epitope | IVGLNKIVRHIV (SEQ. ID NO.:530) | gag p24 267-267–275 | 132, 133 |
| | AAGIGILTV (SEQ. ID NO.:531) | Melan A/Mart- 127 35 | 100 |

Table III sets forth additional antigens useful in the invention that are available from the Ludwig Cancer Institute. The Table refers to patents in which the identified antigens can be found and as such are incorporated herein by reference. TRA refers to the tumor-related antigen and the LUD No. refers to the Ludwig Institute number.

TABLE III

| TRA | LUD No. | Patent No. | Date Patent Issued | Peptide (Antigen) | HLA |
|---|---|---|---|---|---|
| MAGE-4 | 5293 | 5,405,940 | 11 April 1995 | EVDPASNTY (SEQ. ID NO.:532) | HLA-A1 |
| MAGE-41 | 5293 | 5,405,940 | 11 April 1995 | EVDPTSNTY (SEQ ID NO:533) | HLA-A I |
| MAGE-5 | 5293 | 5,405,940 | 11 April 1995 | EADPTSNTY (SEQ ID NO:534) | HLA-A I |
| MAGE-51 | 5293 | 5,405,940 | 11 April 1995 | EADPTSNTY (SEQ ID NO:534) | HLA-A I |
| MAGE-6 | 5294 | 5,405,940 | 11 April 1995 | EVDPIGHVY (SEQ ID NO:535) | HLA-A1 |
|  | 5299.2 | 5,487,974 | 30 January 1996 | MLLAVLYCLL (SEQ ID NO:536) | HLA-A2 |
|  | 5360 | 5,530,096 | 25 June 1996 | MLLAVLYCL (SEQ ID NO:537) | HLA-B44 |
| Tyrosinase | 5360.1 | 5,519,117 | 21 May 1996 | SEIWRDIDFA (SEQ ID NO:538) SEIWRDIDF (SEQ ID NO:539) | HLA-B44 |
| Tyrosinase | 5431 | 5,774,316 | 28 April 1998 | XEIWRDIDF (SEQ ID NO:540) | HLA-B44 |
| MAGE-2 | 5340 | 5,554,724 | 10 September 1996 | STLVEVTLGEV (SEQ ID NO:541) LVEVTLGEV (SEQ ID NO:542) VIFSKASEYL (SEQ ID NO:543) IIVLAIIA1 (SEQ ID NO:544) KIWEELSMLEV (SEQ ID NO:545) LIETSYVKV (SEQ ID NO:546) | HLA-A2 |
|  | 5327 | 5,585,461 | 17 December 1996 | FLWGPRALV (SEQ ID NO: 547) TLVEVTLGEV (SEQ ID NO:548) ALVETSYVKV (SEQ ID NO:549) | HLA-A2 |
| MAGE-3 | 5344 | 5,554,506 | 10 September 1996 | KIWEELSVL (SEQ ID NO:550) | HLA-A2 |
| MAGE-3 | 5393 | 5,405,940 | 11 April 1995 | EVDPIGHLY (SEQ ID NO:551) | HLA-A1 |
| MAGE | 5293 | 5,405,940 | 11 April 1995 | EXDX5Y (SEQ. ID NO.:552) (but not EADPTGHSY) (SEQ. ID NO.:553) E (A/V) D X5 Y (SEQ. ID NO.:554) E (A/V) D P X4 Y (SEQ. ID NO.:555) E (A/V) D P (I/A/T) X3 Y (SEQ. ID NO.:556) E (A/V) D P (I/A/T) (G/S) X2 Y (SEQ. ID NO.:557) E (A/V) D P (I/A/T) (G/S) (H/N) X Y E (A/V) DP (I/A/T) (G/S) (H/N) (L/T/V) Y (SEQ. 11) NO.:559) | HLA-A1 |
| MAGE-1 | 5361 | 5,558.995 | 24 September 1996 | ELHSAYGEPRKLLTQD (SEQ ID NO:560) EHSAYGEPRKLL (SEQ ID NO:561) SAYGEPRKL (SEQ ID NO:562) | HLA-C Clone 10 |
| MAGE-1 | 5253.4 | TBA | TBA | EADPTGHSY (SEQ ID NO:563) | HLA-A I |
| BAGE | 5310.1 | TBA | TBA | MAARAVFLALSAQLLQARLMKE (SEQ ID NO:564) MAARAVFLALSAQLLQ (SEQ ID NO:565) | HLA-C Clone 10 HLA-C Clone 10 |

TABLE III-continued

| TRA | LUD No. | Patent No. | Date Patent Issued | Peptide (Antigen) | HLA |
|---|---|---|---|---|---|
| GAGE | 5323.2 | 5,648,226 | 15 July 1997 | AARAVFLAL (SEQ ID NO:566) YRPRPRRY (SEQ. ID NO.:567) | HLA-C Clone 10 HLA-CW6 |

Preferred peptide antigens are those of tumor associated antigens (TAA) and chronic infections. Particularly preferred peptide antigens are derived from tyrosinose, gp100 or Melan A for the treatment of melanoma.

The peptide antigens of this invention are readily prepared using standard peptide synthesis means known in the art. Generally they can be prepared commercially by one of numerous companies that do chemical synthesis. An example is American Peptides, Inc., where the distributor is CLINALFA AG (Laufelfingen, Switzerland). The antigens are prepared in accordance with GMP standards. Purity is assessed by analytical HPLC. The product is characterized by amino-acid analysis and tested for sterility and the absence of pyrogens.

In delivering an appropriate antigen, e.g., a polypeptide, to the animal's system it may be delivered directly as the polypeptide, or it may be delivered indirectly, e.g., using a DNA construct or vector, or a recombinant virus that codes for the desired antigen. Any vector driving expression in a professional antigen presenting cell is suitable for this purpose. In the indirect delivery, the antigen is expressed in the cell, to be presented by the MHC Class I on the surface of the cell to stimulate the CTL response.

In a preferred embodiment of the invention an encoded antigen can be delivered in the form of a naked plasmid expression vector. Particularly useful constructs are disclosed in U.S. patent application Ser. No. 09/561,572 entitled EXPRESSION VECTORS ENCODING EPITOPES OF TARGET-ASSOCIATED ANTIGENS which is incorporated herein by reference in its entirety. The feasibility of and general procedures related to the use of naked DNA for immunization are described in U.S. Pat. No. 5,589,466, entitled "INDUCTION OF A PROTECTIVE IMMUNE RESPONSE IN A MAMMAL BY INJECTING A DNA SEQUENCE" and U.S. Pat. No. 5,679,647, entitled "METHODS AND DEVICES FOR IMMUNIZING A HOST AGAINST TUMOR-ASSOCIATED ANTIGENS THROUGH ADMINISTRATIONS OF NAKED POLYNUCLEOTIDES WHICH ENCODE TUMOR-ASSOCIATED ANTIGENIC PEPTIDES" which are herein incorporated by reference in their entirety. However the former teaches only intramuscular or intradermal injection while the latter teaches only administration to skin or mucosa. Administration directly to the lymphatic system is greatly more efficient (see examples 6–9, below). Single bolus injection into lymph node required only 0.1% of the dose required in order to obtain a similar level of CTL response by intramuscular (i.m.) injection. It is therefore feasible to establish a protective response against systemic viral infection with a single bolus delivered i.ln., but not with a dose nearing the practical limit delivered i.m. Even repeated bolus injections i.m. failed to establish a protective response against a peripheral virus infection or transplanted tumor whereas lower doses administered i.m. were completely effective.

In another embodiment of the invention an encoded antigen can be delivered in the form of a viral vector. A wide array of viruses with modified genomes adapted to express interposed reading frames but often no, or at least a reduced number of, viral proteins are known in the art, including without limitation, retroviruses including lentiviruses, adenoviruses, parvoviruses including adeno-associated virus, herpesviruses, and poxviruses including vaccinia virus. Such viral vectors facilitate delivery of the nucleic acid component into the cell allowing for expression. A subset of these vectors, such as retroviruses and parvoviruses, also promotes integration of their nucleic acid component into the host genome, whereas others do not.

Bacteria can also serve as vectors, analogously to viruses, i.e. they can be used to deliver a nucleic acid molecule capable of causing expression of an antigen. For example, a strain of *Listeria monocytogenes* has been devised that effects its own lysis upon entering the cytosol of macrophages (its normal target), thereby releasing plasmid from which antigen was subsequently expressed (Dietrich, G. et al. *Biotechnology* 16:181–185, 1998 which is herein incorporated by reference in their entirety). *Shigela flexneri* and *Escherichia coli* have been similarly used (Sizemore, D. R. et al. *Science* 270:299–302, 1995, and Courvalin, P. et al. *Life Sci.* 318:1207–1212, 1995, respectively, which are herein incorporated by reference in their entirety).

The use of microbial vectors for nucleic acid delivery can be complicated by the immune reactions the vectors themselves provoke. When prolonged or repeated administration is required, antibody elicited by the earlier treatment can prevent useful quantities of the vector from ever reaching its intended host. However, by direct administration into, for example, a lymph node, the combination of proximity to host cells and the much reduced effective dose makes it possible to administer a dose capable of evading or overwhelming an existing antibody titer.

The word vector has been used, here and elsewhere, in reference to several modalities and variously modified (e.g. expression vector, viral vector, delivery vector, etc.). The underlying principle here is that a nucleic acid capable of causing expression of an antigen ultimately arrives in an APC, rather than the antigen itself. Unless modified, explicitly or by local context, wherever the term vector is used herein, it is intended to encompass all such possibilities.

These foregoing techniques are distinct from the approach of modifying the microbial genome (including extrachromosomal DNA) so that the antigen is produced as a component of the microbe (virus, bacteria, fungi, protazoan, etc., etc.), which is then itself administered as the immunogen. Obviously, the genomic modification would most likely involve the use some reagent falling within the above definition of vector. Again, the distinction is whether the vaccine includes the already synthesized antigen, or a nucleic acid capable of causing an APC to express the antigen in vivo. This strategy constitutes a further embodiment of the invention. For rhetorical clarity we have discussed these approaches as if they were mutually exclusive, but in fact combinations are possible, e.g., a virus vector as above that also incorporates a target epitope into a capsid or envelope protein.

Similarly, antigen presenting cells can also be manipulated in vitro and then themselves used as the active component of a vaccine. Antigen expression can be conferred by delivering nucleic acid encoded antigen using any of the transduction techniques known in the art, including without limitation electroporation, viral or bacterial transduction, lipid-mediated transduction, and biolistic bombardment. Alternatively the APCs may simply be pulsed with antigen. As with any of the other embodiments of this invention an antigen can be an approximately 8–10 amino acid peptide representing a single epitope, a complete protein, a polypeptide encompassing one or more epitopes (including epitopes originally derived from multiple proteins) or other forms of antigen described above.

Antigens may be used alone or may be delivered in combination with other antigens or with other compounds such as cytokines that are known to enhance immune stimulation of CTL responses, such as, GM-CSF, IL-12, IL-2, TNF, IFN, IL-18, IL-3, IL-4, IL-8, IL-9, IL-13, IL-10, IL-14, IL-15, G-SCF, IFN alpha, IFN beta, IFN gamma, TGF alpha, TGF beta, and the like. The cytokines are known in the art and are readily available in the literature or commercially. Many animal and human tumors have been shown to produce cytokines such as IL-4, IL-10, TGF-B that are potent modulators of the immune response and that protect tumors from immune-mediated destruction. The production of IL-4, IL-10 or TGF-B by the tumors may achieve this protective effect by suppressing the induction of cellular immunity, including the elaboration of CTL responses. Alternatively, cytokines that support CTL responses can be exogenously added to help in the balance between induction of anti-tumor cell mediated and non-tumor-destructive humoral responses. Several such exogenous cytokines show utility in experimental mouse vaccination models which are known to enhance CTL responses, including GM-CSF, IFN and IL-2. An effective exogenous cytokine that may be used is GM-CSF. GM-CSF is reported to enhance the expression of the so called "co-stimulatory" molecules, such as B7-1 or B7-2 on antigen presenting cells (APC), which are important players in the symphony of interactions that occur during stimulation of CTL by APC. Moreover, GM-CSF is known to induce activation of APC and to facilitate growth and differentiation of APC, thereby making these important CTL stimulating cells available both in greater numbers and potency.

Delivery of the Antigen

This invention is based in part on the observation that a CTL response is not sustained using standard vaccine techniques. While not wanting to be bound by any particular theory, it is thought that T cells do not have a functional memory that is long-lived. Antibody-mediated B-cell memory, on the other hand, appears to have a long-lived effector memory. Thus, delivering an antigen that produces a CTL response must be done over time to keep the patient's immune system appropriately stimulated to attack the target cells. While it has been suggested that antigens and adjuvants can be prepared as biodegradable microspheres or liposomes, none of these preparations have thus far provided a CTL response that is useful for attacking cancer cells or pathogens on a long term basis. The delivery must be sustained over the desired period of time at a level sufficient to maintain the antigen level to obtain the desired response and that it must be delivered from a reservoir having fluid antigen composition that is introduced so that it reaches the animal's lymphatic system.

Ultimately antigen must find its way into the lymphatic system in order to efficiently stimulate CTL. However, delivery of antigen according to the invention can involve infusion into various compartments of the body, including but not limited to subcutaneous, intravenous, intraperitoneal and intralymphatic, the latter being preferred. Each of these various points of infusion results in antigen uptake into the lymphatic system. The relative amounts of antigen needed to induce a beneficial CTL response varies according to the different sites of infusion. In general, direct infusion of antigen into the lymph system is deemed to be the most efficient means of inducing a CTL response, but that the material difference between the various routes is not necessarily relevant in terms of the quantity of antigen needed, or, in terms of the operating parameters of the invention. The pump systems of the invention are capable of delivering material quantities of antigen in a range that makes the invention suitable for inducing CTL response through delivery to all compartments of the body. CTL stimulation based on delivery of antigen via various routes will be variable, based on the properties of different antigens, which will reflect factors that influence antigen behavior in the body and its rate of equilibration to (or longevity in) the lymph, such an antigen stability in the body fluid, solubility of antigen in body fluid, binding affinity for HLA and potency as a stimulator of CTL.

It is most efficient, and therefore, preferred, that the introduction is done as directly as possible to the lymphatic system to avoid the destruction of the antigen by metabolism in the body. When introduction of a fluid antigen composition occurs subcutaneously, larger quantities of antigen are needed to assure enough antigen reaches the lymphatic system. Such subcutaneous injection is contemplated by this invention if it can be justified by factors such as cost, stability of the antigen, how quickly the antigen gets to the lymph system, how well it equilibrates with the lymph, and other factors that the attending doctor or specialist will recognize. Subcutaneous delivery will generally require 100 to 1000 times more antigen than direct delivery to the lymph system. It is preferable, therefore, that the antigen composition is introduced through a device for local administration to the lymphatic system, e.g. the spleen, a lymph node, or a lymph vessel. The device for local administration may be positioned outside the patient or implanted into the patient. In either case, the device will have a reservoir to hold the fluid antigen-containing composition, a pump to transfer the composition, and a transmission channel leading from the reservoir to be directed to the preferred region of administration in the patient's body. In either case it is preferably portable.

For the device positioned outside the patient's body (the external device), there are numerous devices used for delivering insulin to diabetic patients that are useful in this invention. Generally these are comprised of a reservoir for holding the antigen composition (instead of insulin), a programmable pump to pump the composition out of the reservoir, a transmission channel or line for transmitting the composition, and a means to introduce the composition into the animal's body to ultimately reach the lymphatic system.

The pump employed may be a roller/peristaltic pump, a syringe pump, a piston/valve pump, a gas pressure pump, or the like that has a power source (generally a battery for portability) that is programmable to deliver the desired level of antigen composition to the patient's body and the lymphatic system. A further discussion of the operation of these pumps may be found "Insulin Pump Therapy" by E. Austenst and T. Stahl, Walter de Gruyter, Berlin, New York (1990), at Chapter 3. A list of pumps available at that time that are useful for this invention are given in Table IV.

More recent versions of these pumps are available from the manufacturers shown.

TABLE IV

| Name | Manufacturer/distributor | Weight (g) | Size (mm) |
|---|---|---|---|
| Nordisk Infusor | Nordisk | 180 | 100 × 60 × 20 |
| Betatron I | CPI/Lilly | 197 | 99 × 66 × 20 |
| RW 90 P/RW 91 P/RW 92 | Dahedi/EA Satorius Instruments | 110 | 109 × 42 × 22 |
| MRS 4-Infuser | Disetronic | 100 | 75 × 53 × 19 |
| B-D 1000 | Becton-Dickinson | 131 7 | 8 × 57 × 20 |
| Nordisk Infusor MK 11 | Nordisk | 180 | 113 × 65 × 22 |
| MRS 3-Infuser | Disetronic | 100 | 75 × 53 × 18 |
| A S8 MP | Autosyringe/Travenol | 161 | 102 × 64 × 19 |
| Betatron 11 | CPULilly | 197 | 99 × 66 × 20 |
| Minimed 504 | Pacesetter/Haselmeyer | 106 | 86 × 21 × 51 |
| Minimed 404 S* | Pacesetter | 106 | 86 × 21 × 51 |
| MRS I/H-Tron | Disetronic/Hoechst | 100 | 75 × 53 × 18 |

*not yet commercially available

Particularly useful pumps are the Disetronic H-Tron V 100 Insulin Pump from Disetronic Medical Systems, Burgdorf, Switzerland and the Minimed 507 Insulin Pump from MiniMed Inc., 12744 San Fernando Road, Sylmar, Calif. 91342. The MiniMed is particularly useful in that it allows programming a bolus without looking at the pump through a series of audio tones (settable in either 0.5 or 1.0 unit increments) and allows programming a bolus for delivery over an extended period of time—from 30 minutes to 4 hours. It provides up to 12 basal rates (or profiles) that can be programmed per 24 hours from 0.0–25 units/hour in 0.1 unit increments. The device allows for the temporary increase or decrease of a set basal rate from 30 minutes to 24 hours in 30 minute increments, Other features relating to safety, time display, memory, etc. are available from the manufacturer.

The reservoir for the antigen composition should be large enough for delivery of the desired amount of antigen over time and is easily refillable or replaceable without requiring the user to reinsert the means for introducing the antigen composition to the lymph system.

In preparing the antigen compositions of this invention, a composition (preferably aqueous) is prepared to be compatible with the lymph system and is physiologically acceptable to the animal being treated. In preparing the antigen compositions useful in this invention one considers the physicochemical properties of the antigen such as the isoelectric point, molecular weight, glycosylation or other post-translational modification, and overall amino acid composition. These properties along with any known behavior of the drug in different solutions (e.g. different buffers, cofactors, etc.) as well as its in vivo behavior will help guide the choice of formulation components. One parameter that impacts all the major degradation pathways is the solution pH. Thus, the initial formulations also assess the pH dependence of the degradation reactions and the mechanism for degradation can often be determined from the pH dependence to determine the stability of the protein in each solution. Rapid screening methods usually involve the use of accelerated stability at elevated temperatures (e.g. 40° C.) using techniques known in the art.

In general the antigen compositions useful in this invention will be prepared suitable for parenteral injection, in very small quantities. As such a composition must be free of contamination and have a pH compatible with the lymph system. However, because very small quantities of the antigenic composition will be delivered it need not be the same pH as blood or lymph, and it need not be aqueous-based. For antigens that are less soluble a suitable cosolvent or surfactant may be used, such as dimethyl sulfoxide (DMSO) or PLURONIC brand surfactants. The pH range that is compatible is from about 6.7–7.3 and can be prepared using water for injection to meet USP specifications (see Remington: The Science and Practice of Pharmacy, Nineteenth Edition; Chapters 86–88). Generally, a standard saline solution that is buffered with a physiologically acceptable weak acid and its base conjugate, e.g., a phosphate or citrate buffering system, will be the basis of the antigen composition. In some cases, a small amount of an antioxidant may be useful to stabilize the composition and prevent oxidation. Factors to consider in preparing the antigen compositions may be found in the 1994 American Chemical Society book entitled "Formulation and Delivery of Proteins and Peptides" (Acs Symposium Series, No. 567) by Jeffery L. Cleland and Robert Langer (Editor)).

For nucleic acid encoded antigens similar considerations apply, although the variety of physico-chemical properties encountered with polypeptides is absent, so that acceptable formulations will have nearly universal applicability. As seen in examples 6–10, plasmid DNA in standard phosphate buffered saline (PBS) is an acceptable and effective formulation. In some embodiments of the invention, DNA is administered continuously or intermittently at short intervals, from a reservoir worn on, or implanted in, the patient's body. It is preferable that the DNA be maintained in a soluble, stable form at or near body temperature over a period of time measured minimally in days. In such applications where the formulated nucleic acid will be delivered from a reservoir over a period several days or longer, the stability of the nucleic acid at room or body temperature for that period of time, as well as its continued sterility, take on increased importance. The addition of bacteriostatic agents (e.g. benzyl or ethyl alcohol) and chelating agents (e.g. EDTA) is useful toward these ends. Formulations containing about 1–10% ethyl alcohol, 0–1% benzyl alcohol, 0.25–0.5 mM EDTA and a citrate-phosphate buffer of pH 7.4–7.8 generally perform well. Such formulations are also appropriate for bolus injections.

Generally the amount of the antigen in the antigen composition will vary from patient to patient and from antigen to antigen, depending on such factors as the activity of the antigen in inducing a response and the flow rate of the lymph through the patient's system. In general the antigen composition may be delivered at a rate of from about 1 to about 500 microliters/hour or about 24 to about 12000 microliters/day. The concentration of the antigen is such that about 0.1 micrograms to about 10,000 micrograms of the antigen will be delivered during 24 hours. The flow rate is based on the knowledge that each minute approximately about 100 to about 1000 microliters of lymph fluid flows through an adult inguinal lymph node. The objective is to maximize local concentration of vaccine formulation in the lymph system. A certain amount of empirical investigation on patients will be necessary to determine the most efficacious level of infusion for a given vaccine preparation in humans.

To introduce the antigen composition into the lymphatic system of the patient the composition is preferably directed to a lymph vessel, lymph node, the spleen, or other appropriate portion of the lymph system. Preferably, the composition is directed to a lymph node such as an inguinal or axillary node by inserting a catheter or needle to the node and maintaining the catheter or needle throughout the delivery. Suitable needles or catheters are available made of metal or plastic (e.g. polyurethane, polyvinyl chloride [PVC], TEFLON, polyethylene, and the like). In inserting the catheter or needle into the inguinal node for example, the inguinal node is punctured under ultrasonographic control using a Vialon™ Insyte-W™ cannula and catheter of 24G3/4 (Becton Dickinson, USA) which is fixed using Tegadenn transparent dressing Tegaderm™ 1624, 3M, St. Paul, Minn. 55144, USA). This procedure is generally done by an experienced radiologist. The location of the catheter tip inside the inguinal lymph node is confirmed by injection of a minimal volume of saline, which immediately and visibly increases the size of the lymph node. The latter procedure allows confirmation that the tip is inside the node and can be performed to ensure that the tip does not slip out of the lymph node can be repeated on various days after implantation of the catheter. In case the tip did in fact slip out of location inside the lymph node, a new catheter can be implanted.

In another embodiment, the antigen is delivered to the lymphatic system through an article of manufacture that is implanted in the animal, preferably at or near a site of a lymphatic organ. The article will include a pump that can deliver the antigen at a controlled rate over a pre-determined period of time and is suitable for use in the host. Several devices are known in the art for the delivery of agents (such as drugs) in humans or animals and these can be used or adapted for use in the present invention.

The implantable device will be similar to the external device discussed above in that it comprises a reservoir of a physiologically-acceptable, aqueous, antigen-containing composition that is capable of inducing a CTL response in an animal, a pump positioned in association with the reservoir to deliver the composition at a defined rate, a transmission channel to discharge the composition from the reservoir, and optionally a delivery line connected to the transmission channel, which delivery line is of a size suitable for positioning in the animal and for delivery of the composition in a manner that reaches the lymphatic system of the animal.

Preferably the pump in the implantable device is an osmotic pump of the type used in the ALZET® model device or the DUROS™ model device pioneered by Alza Corporation, Palo Alto, Calif. or in a device made by Pharmetrix and exemplified in U.S. Pat. No. 4,838,862. The osmotic pump utilizes the osmotic effect using a membrane permeable to water but impermeable to a solute. Osmotic pressure built up in a device is used to deliver a composition at a controlled rate over time. A review by Giancarlo Santus and Richard Baker of "Osmotic Drug Delivery: A Review of the Patent Literature" in the Journal of Controlled Release 35 (1995) 1–21, provides useful guidelines for the type of osmotic pumps that are useful in this invention. The osmotic pump forces the composition through a discharge orifice to discharge the composition, Optionally a delivery line connects to the discharge orifice to position the line suitably for delivery to the lymphatic system of the animal. Patents that describe devices useful in this invention include the following U.S. patents: (A) U.S. Pat. No. 3,604,417 assigned to American Cyanamid; (B) U.S. Pat. Nos. 4,838,862; 4,898, 582; 5,135,498; 5,169,390; and 5,257,987 all assigned to Pharmetrix, (C) U.S. Pat. Nos. 4,340,048; 4,474,575; 4,552, 651; 4,619,652; 4,753,651; 3,732,865; 3,760,804; 3,760, 805; 3,929,132; 3,995,632; 4,034,756; 4,350,271; 4,455, 145; 5,017,381; 5,023,088; 5,030,216; 5,034,229; 5,037, 420; 5,057,318; 5,059,423; 5,110,596; 5,110,597; 5,135, 523; 5,137,727; 5,174,999; 5,209,746; 5,221,278; 5,223, 265; 3,760,984; 3,987,790; 3,995,631; 4,203,440; 4,286, 067; 4,300,558; 4,304,232; 4,340,054; 4,367,741; 4,450, 198; 4,855,141; 4,865,598; 4,865,845; 4,872,873; 4,929, 233; 4,963,141; 4,976,966, all assigned to Alza Corp. Each of the foregoing patents are incorporated herein by reference.

A basic osmotic pump device incorporates a housing containing a chamber for storing the antigen containing composition to be delivered, separated from a compartment containing an osmotic salt material by a barrier that is moveable under pressure such as a piston or a flexible impermeable membrane. The compartment containing the osmotic salt is separated from osmotic fluid by a semipermeable membrane. In some embodiments, a fluid barrier, such as a foil sheet, isolates the osmotic salt chamber from the osmotic fluid, keeping the pump inactivated until removal of the barrier immediately prior to use. Other osmotic pump devices use body fluid as the osmotic fluid. In these devices a semipermeable membrane separates the osmotic salt compartment from body fluids, and the pump is activated once inserted into the body under exposure to body fluids. In either case, volumetric expansion of the osmotic salt compartment drives the expulsion of the stored antigen from the compartment and into the surrounding environment of the body. These pumps have been highly successful at achieving steady-state pumping and delivery of agents. The pumps are of a small size that can be inserted into a patient, with flexible consideration as to location. This is important in the case of CTL vaccines, since the inventor has determined that efficient induction of CTL responses is contingent on the antigen or antigen expression system being delivered into the lymphatic system, in order to ultimately achieve antigen delivery into a lymphatic organ such as the spleen. Antigen delivered into a lymph node is 100–1000 times more efficient at inducing CTL responses compared with conventional subcutaneous delivery. A modification to the osmotic pump incorporates a microcatheter attachment (i.e., the optional delivery line) at its discharge end, such that when the pump is implanted proximal to a lymphatic organ, such as a lymph node, the catheter can be inserted into the organ to facilitate delivery of the vaccine directly into the lymphatic system.

Prior to the administration of the antigen using any of the above vehicles, methods may be used to assist in the determination of the optimum location for the antigen delivery. For example, when using the osmotic pump, radiography may be used to image a patient's lymphatic flow, to determine where relatively high lymphatic drainage occurs, in order to decide upon an insertion position for the osmotic pump that maximizes delivery into the lymphatic system. Since each patient has unique lymphatic drainage profiles, imaging would be conducted for each individual prior to insertion of osmotic pump for delivery of antigen. When using direct cannulation of the lymphatic vessel, such as in the use of osmotic or insulin pumps to deliver antigen, ultrasound can be used to position the needle directly into the lymphatic vessel and to monitor its positioning over the period of treatment.

The following non-limiting examples are illustrative of the present invention.

EXAMPLES

Materials and Methods For Examples 1–5

Mice: The generation of T cell receptor transgenic mice (TCR+ mice) in which approx. 90% of the CD8+ T cells express a TCR recognizing the immunodominant LCMV-glycoprotein epitope (gp-peptide aa33-41, p33:K.AVYNFATC-SEQ ID NO:569) presented on H-$2D^b$, has been described in detail. All experimental mice were between 8 and 12 weeks of age and bred and held under strict pathogen free conditions at the Institut Für Labortierkunde at the University of Zurich.

Viruses: LCMV (Armstrong strain) was originally obtained from Dr. M. B. A. Oldstone, Scripps Clinics and Research Foundation, LaJolla, San Diego, Calif. Seed virus was grown on BHK cells and plaqued on MC57 cells using an immunological focus assay, as described previously.

Osmotic pump: ALZA model #1007b.

In vivo protection assays for specific CTL activity: The in vivo assay for the detection of CTL activity by challenge infections with LCMV has been described in detail previously (Oehen et al. 1991). Briefly, mice are intravenously challenged with $2\times10^3$ pfu of LCMV (Armstrong), After 4 days the titer of LCMV is determined using the above mentioned immunological focus assay.

Primary ex vivo cytotoxicity against LCMV-gp: Mice were injected intravenously with 10 μg of p33. After 36 hours spleen single cell suspensions were coincubated for 5 h with $^{51}$Cr-labeled syngeneic EL-4 (H-$2^b$) target cells, that were either pulsed with p33 or left unpulsed. Specific lysis was calculated as [(experimental $^{51}$Cr release–spontaneous $^{51}$Cr release)/(total $^{51}$Cr release–spontaneous $^{51}$Cr release)× 100%].

LCMV induced foot pad swelling reaction: Mice were infected with LCMV (Armstrong) by intradermal injection into the hind footpad (5000 pfu in 30:1), Footpad thickness was measured daily with a spring loaded caliper. Footpad swelling is calculated as (measured thickness-thickness before injection)/(thickness before injection).

Example 1
Continuous Release of Peptide Antigen Using Osmotic Pump Induces Potent CTL Response in C5BL/6 Mice C57BL/6 mice were either intravenously injected with a single dose of 50 μg p33 (including 500 ng GM-CSF) (circles) or were implanted with a micro-osmotic pump releasing a mixture of 50 μg of p33 and 500 ng GM-CSF over a time period of 7 days (triangles), or were left naive (data not shown). After 7 days mice were sacrificed to prepare single cell suspensions from the spleen. Spleen cells were restimulated in vitro for 5 days by p33 pulsed in the presence of low amounts of IL-2. Specific cytotoxicity was measured using $^{51}$Cr-labeled EL-4 target cells pulsed with p33. Specific lysis of EL-4 target cells without p33 was less than 16% for all effectors. The results are shown in FIG. 1.

Example 2
Continuous Release of Antigen Induces CTL Immunity Against Virus in C57BL/6 Mice C57BL/6 mice were either intravenously injected with a single dose of 50 μg p33 (including 500 ng GM-CSF. Pharmingen) or were implanted with a microsomotic pump releasing a mixture of 50 μg of p33 and 500 ng GM-CSF over a time period of 7 days, or were left naive. After 7 days specific CTL activity was assessed in vivo using anti-viral protection assays. C57BL/6 mice were intravenously challenged with LCMV Armstrong strain ($2\times10^3$ p.f.u.). After 4 days mice were sacrificed and LCMV titers were determined in spleens using an immunological focus assay. Mice implanted with osmotic pump showed significantly lower virus titers indicating active CTL immunity against the virus (Table V).

TABLE V

| C57BL/6 Mice | Virus Titer (loglo) |
| --- | --- |
| Single injection | 4.2 |
| Single injection | 4.6 |
| Single injection | 4.0 |
| Pump delivered | 2.2 |
| Pump delivered | 1.8 |
| Pump delivered | 2.0 |
| Unprimed | 4.8 |
| Unprimed | 3.8 |
| Unprimed | 4.4 |

Figure 2B:
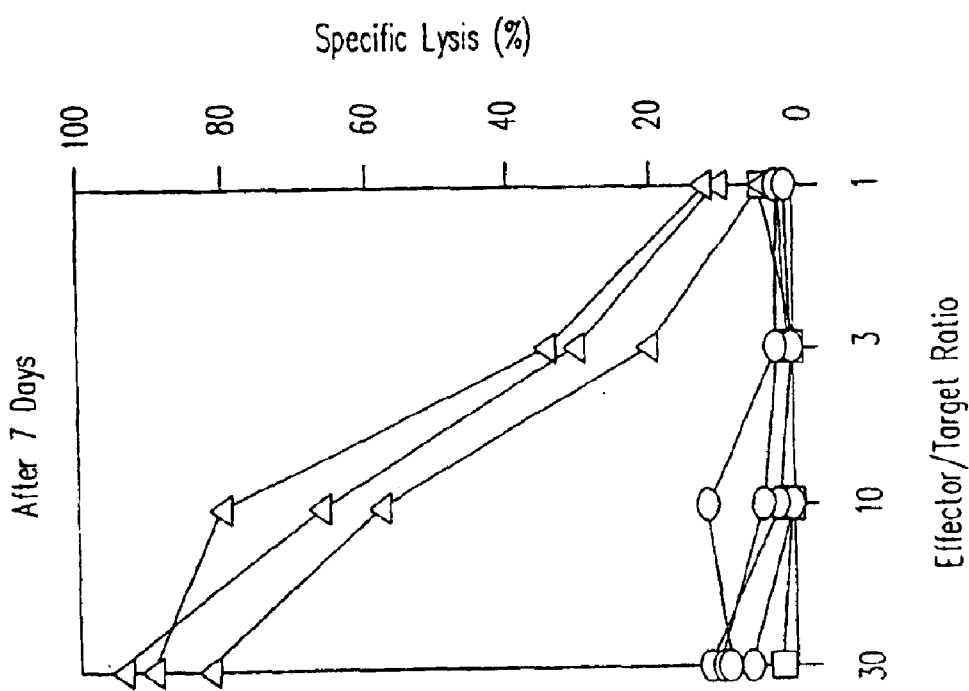
FIG. 2(A and B) are graphs showing the lysis of target cells by CTL versus the effector/target ratio when antigen is delivered as a single dose (circles), when antigen is delivered by a continuous pump (triangles) and negative control (squares) at (A) 36 hours and (B) 7 days.
FIG. 2C is a graph showing the footpad swelling versus time when antigen is delivered as a single dose (circles) and when antigen is delivered by a continuous pump (triangles).
Figure 2A:
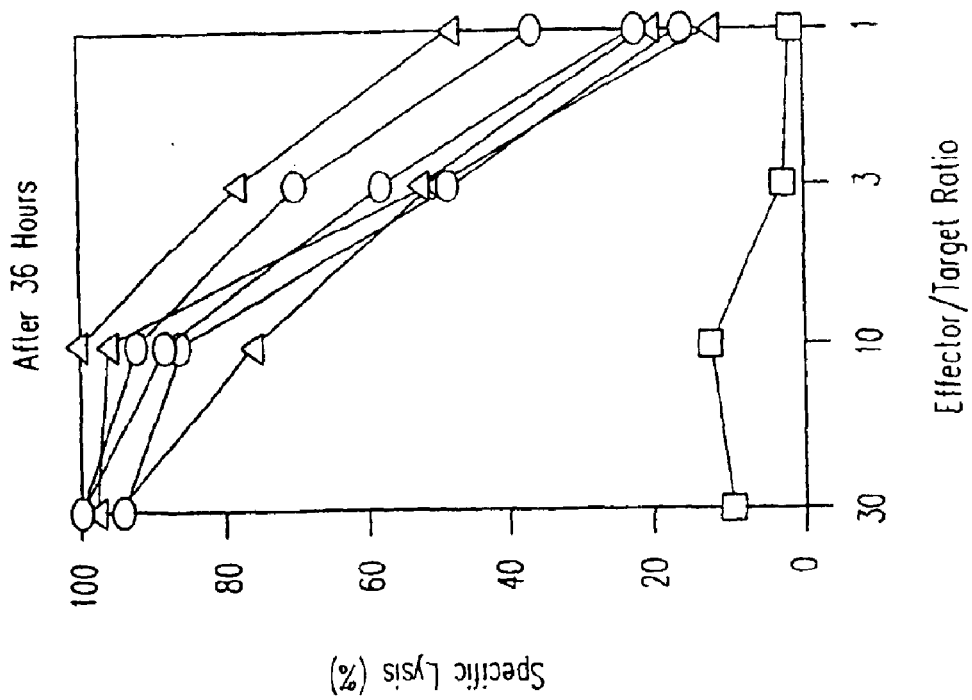

Example 3
Continuous Release of Antigen Maintains Potent CTL Effectors in TCR Transgenic Mice TCR transgenic mice were either intravenously injected with a single dose of 50 μg p33 (circles) or were implanted with a microsomotic pump releasing a mixture of 50 μg of p33 (triangles), or left naïve (squares). After 36 hours mice were sacrificed to prepare single cell suspensions from the spleen which were assayed ex vivo for p33-specific cytotoxicity using $^{51}$Cr-labeled EL-4 target cells pulsed with p33. Similarly mice were either intravenously injected with a single dose of 50 μg p33 (circles) or were implanted with a micro-osmotic pump releasing a mixture of 50 μg of p33 over a time period of 7 days (triangles), or were left naïve (squares). After 7 days mice were sacrificed to prepare single cell suspensions from the spleen to assay ex vivo p33-specific cytotoxicity using $^{51}$Cr-labeled EL-4 target cells pulsed with p33. Specific lysis of EL-4 target cells without p33 was less than 18% for all effectors. The results are shown in FIGS. 2A and 2B.

Figure 2C:
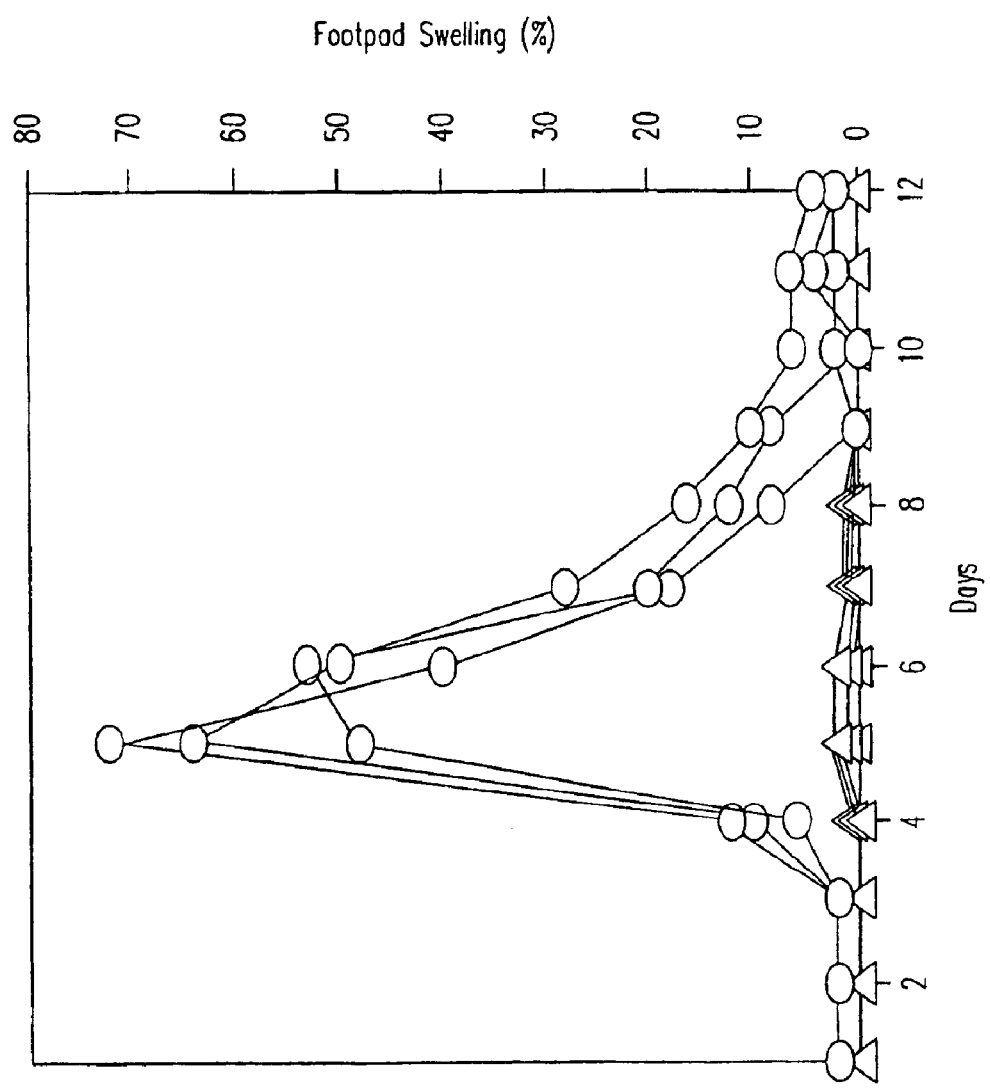

Continuous Release of Antigen Maintains Protective CTL Response Against Virus Infection After 7 days TCR transgenic mice were challenged by intradermal LCMV injection into their hind foot pads ($2\times10^3$ pfu in 30 μ). The absence of a foot pad swelling reaction, as observed in mice with an implanted pump (triangles), indicates that at the time point of injection there was active CTL immunity inhibiting local replication of the virus in the foot pad. In contrast, foot pad swelling, as observed in mice injected with the peptide as a single bolus (circles) and naive control mice (data not shown), indicated that LCMV successfully replicated in the foot pad in the absence of protective CTL. The results are shown in FIG. 2C.

Figure 3:
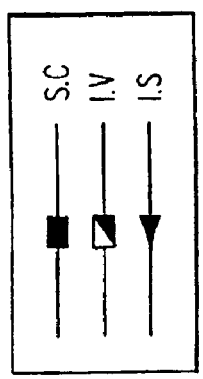
FIG. 3 is a graph showing the lysis of target cells by CTL versus the dose of the peptide antigen when the antigen is delivered subcutaneously, intravenously and intrasplenically.
Figure 3:
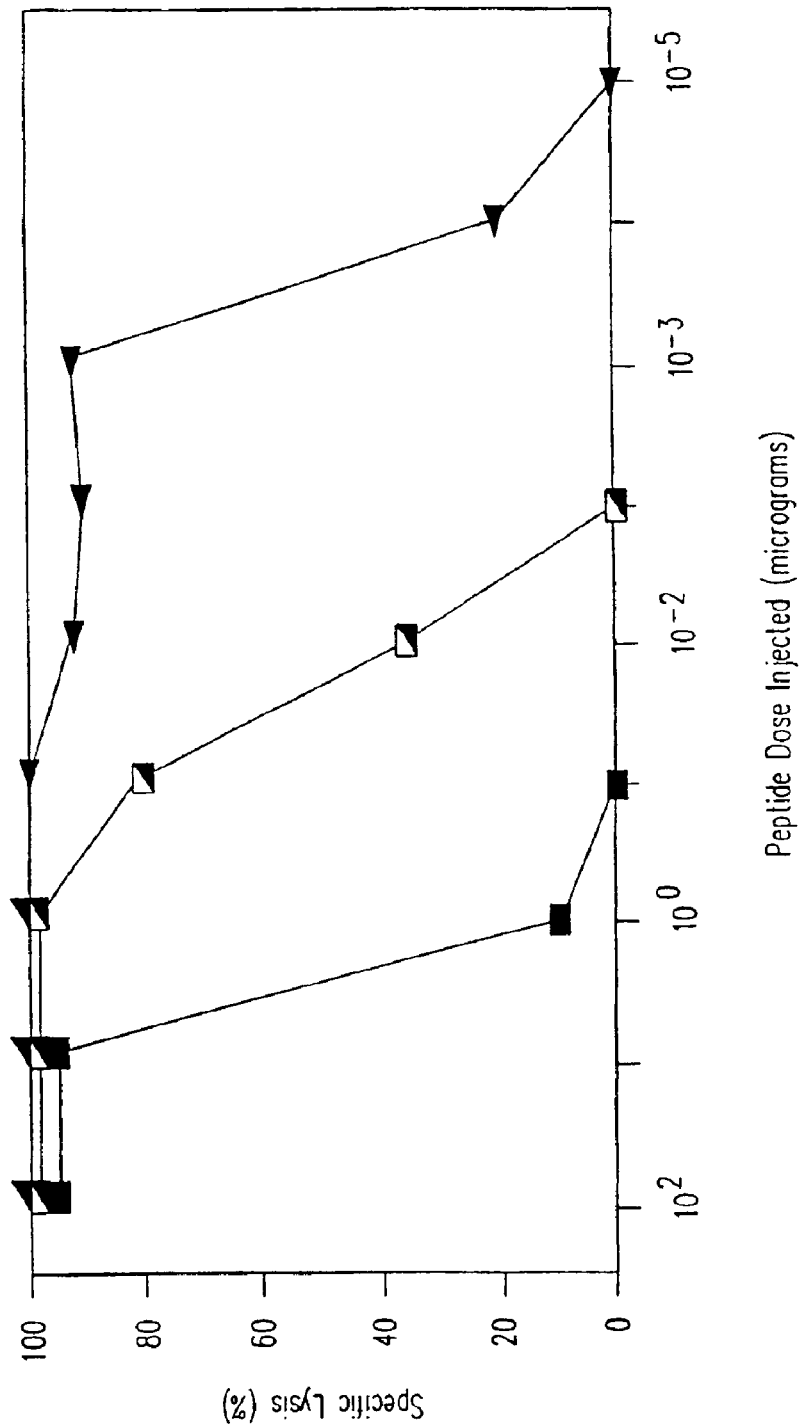

Example 4
Direct Delivery of Antigen into Lymphatic Organ Dramatically Increases Efficiency of CTL Induction TCR transgenic mice were injected with graded doses of gp-peptide p33 either subcutaneously (S.C.), intravenously (I.V.) or directly into the spleen (I.S.) via a small abdominal incision. The efficiency of CTL induction was assessed by measuring gp-specific CTL activity 24 hours after injection. CTL activity is known to peak one day after injection of peptide. Mice were sacrificed to prepare single cell suspensions from draining lymph nodes or from spleen to assay ex vivo p33-specific cytotoxicity using $^{51}$Cr-labeled EL-4 target cells pulsed with p33. Specific lysis of EL-4 target cells without p33 was less than 12% for all effectors. The results are shown in FIG. 3.

Figure 4:
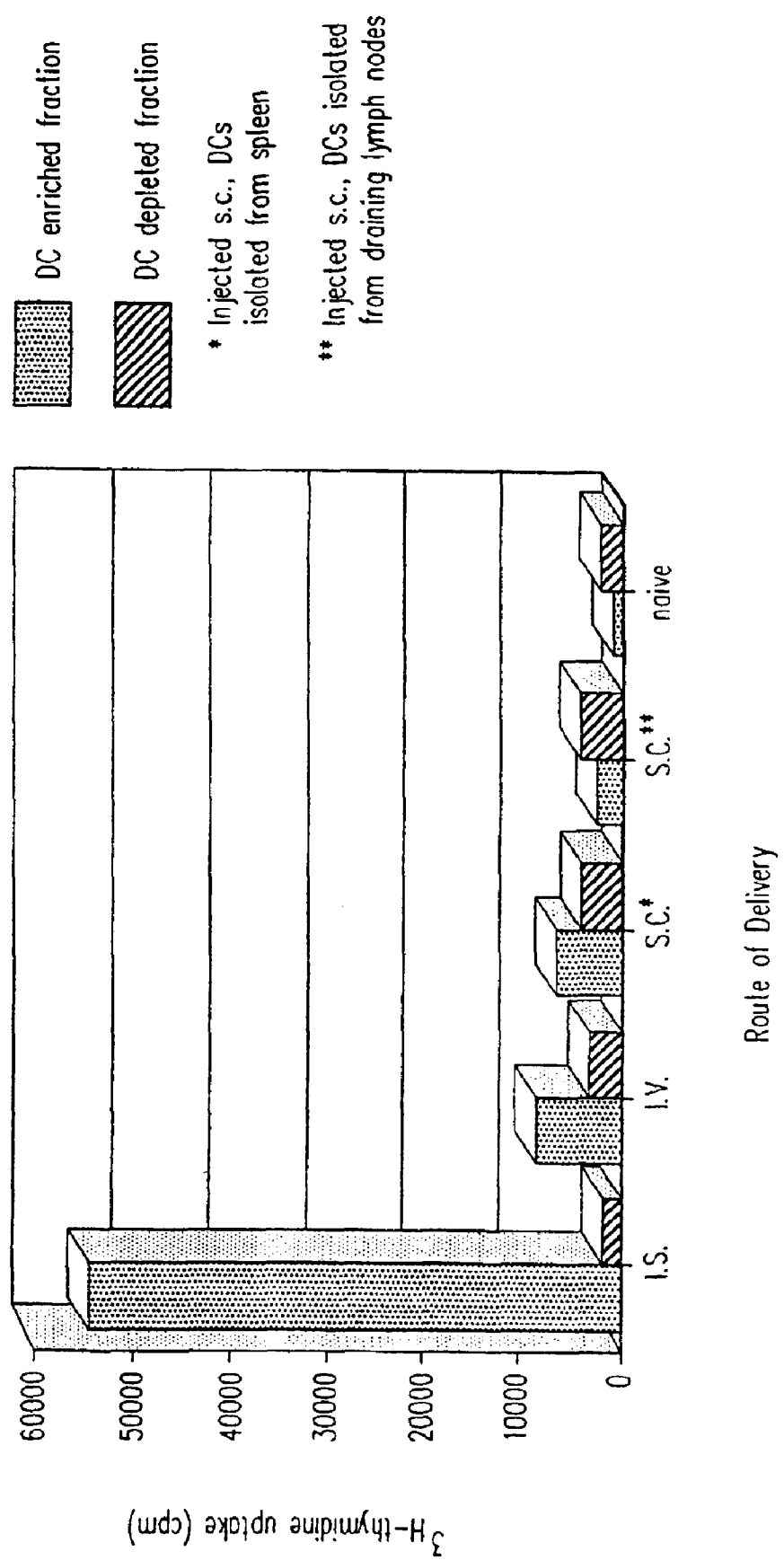
FIG. 4 is a bar graph showing tritiated thymidine uptake in CTL cells induced by antigen introduced intravenously, intrasplenically and subcutaneously.

Example 5
Dendritic Cells Purified from Mice Receiving Intrasplenic Injection of Peptide Potently Stimulate CTL The effect of directing peptide delivery into lymphatic system was assessed. Peptide p33 was injected either i.v., s.c. or directly into the spleen of wild-type C57BL/6 mice. After 2 hours, DCs were isolated from the spleen of animals injected either i.s. or i.v., and additionally from the regional draining lymph nodes of animals injected s.c. Cells isolated from these tissues were sorted for DCs using magnetic beads coupled with a monoclonal antibody recognizing the integrin-alpha chain, a marker specific for DCs in spleen and lymph nodes. The positively and the negatively sorted cell fractions were compared regarding their capacity to in vitro stimulate naive CD8+ T cells from TCR transgenic mice specific for LCMV-gp. Only when peptide had been directly injected into the spleen, the DC containing cell fraction stimulated CTL to proliferate, as measured by $^3$H-thymidine uptake. This indicated that CTL induction after direct injection of peptide into lymphatic organs reflected efficient loading of DCs with peptide. In contrast, the fraction depleted for DC did not induce proliferation and DCs isolated from lymphoid organs of i.v. and s.c injected mice were not effective stimulators. The results are shown in FIG. 4.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Figure 6:
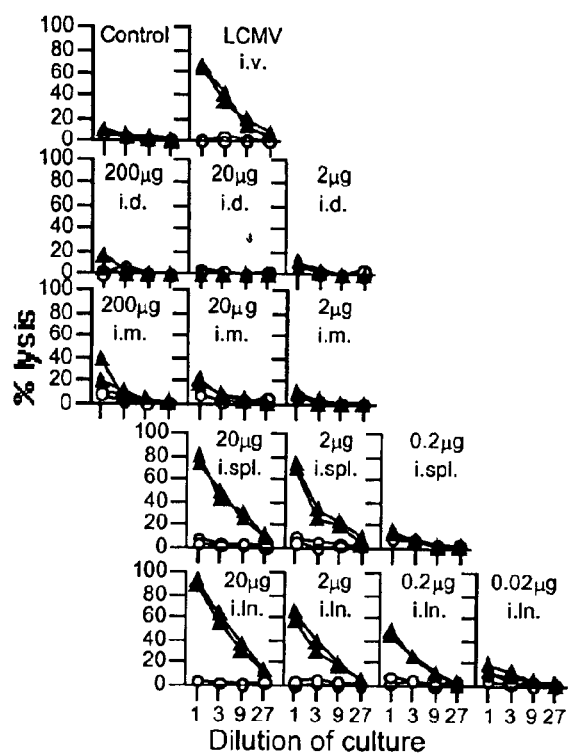
FIG. 6. Comparison of anti-peptide CTL responses following immunization with various doses of DNA by different routes of injection.

Example 6
Induction of CTL Response with Naked DNA is Most Efficient by Intra-Lymph Node Immunization In order to quantitatively compare the CD8+ CTL responses induced by different routes of immunization we used a plasmid DNA vaccine (pEGFPL33A) containing a well-characterized immunodominant CTL epitope from the LCMV-glycoprotein (G) (gp33; amino acids 33–41) (Oehen, S., et al. *Immunology* 99, 163–169 2000), as this system allows a comprehensive assessment of antiviral CTL responses. Groups of 2 C57BL/6 mice were immunized once with titrated doses (200–0.02 μg) of pEGFPL33A DNA or of control plasmid pEGFP-N3, administered i.m. (intramuscular), i.d. (intradermal), i.spl. (intrasplenic), or i.ln. (intra-lymph node). Positive control mice received 500 pfu LCMV i.v. (intravenous). Ten days after immunization spleen cells were isolated and gp33-specific CTL activity was determined after secondary in vitro restimulation. As shown in FIG. 6, i.m. or i.d. immunization induced weakly detectable CTL responses only when high doses of pEGFPL33A DNA (200 μg) were administered. In contrast, potent gp33-specific CTL responses were elicited by immunization with only 2 μg pEGFPL33A DNA i.spl. and with as little as 0.2 μg pEGFPL33A DNA given i.ln. (FIG. 6; symbols represent individual mice and one of three similar experiments is shown). Immunization with the control pEGFP-N3 DNA did not elicit any detectable gp33-specific CTL responses (data not shown).

Figure 7:
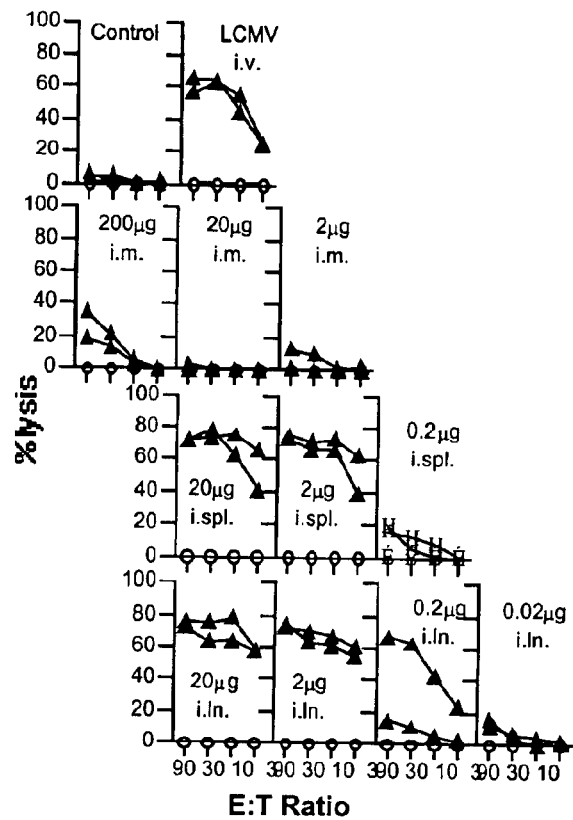
FIG. 7. Comparison of anamnestic antiviral CTL responses following immunization with various doses of DNA by different routes of injection.

Example 7
Intra-lymph Node Immunization is the Most Efficient way to Induce Antiviral Anamnestic CTL Responses Similar thresholds for CTL detection were observed when a different readout system was used. Groups of 2 C57BL/6 mice were immunized once with titrated doses of pEFGPL33A DNA (0.2–200 μg) and positive control mice received 500 pfu LCMV i.v., as above. Ten days later they were challenged with 5×10$^4$ pfu LCMV i.v. Four days after challenge spleen cells were isolated and ex vivo CTL activity was assayed. This time point is too early to detect any primary CTL response to LCMV infection in naive mice (FIG. 7, Controls), but it allows the detection of anamnestic CTL responses in mice which have been previously immunized (FIG. 7, LCMV). As before, mice immunized with 200 μg intramuscularly showed only weak anamnestic CTL responses following LCMV challenge, which were not detectable when lower immunizing doses of DNA were used (FIG. 7). Those immunized by the i.spl. route showed strong anamnestic CTL responses which titered out at an immunizing dose of 2 μg pEFGPL33A DNA, while the i.ln. route of immunization was again more efficient with anamnestic CTL responses detectable when only 0.2 μg pEFGPL33A DNA was administered (FIG. 7).

These results from examples 6 and 7 clearly demonstrate that administration of plasmid DNA directly into lymphoid tissues is 100- to 1000-fold more efficient than intradermal or intramuscular routes for the induction of CTL responses. In addition, they show that the intra-lymph node route is around 10-fold more efficient than the intrasplenic route.

Example 8
Naked DNA Elicits Superior Protection Against Systemic and Peripheral Virus Infection by Intra-lymph Node Compared to Intramuscular Immunization To examine whether the enhanced CTL responses elicited following i.ln. immunization with plasmid DNA were able to qualitatively influence antiviral immunity, we used challenge infections with LCMV or with recombinant vaccinia virus expressing the LCMV-G (Vacc-G2) as models of systemic and peripheral virus infection, respectively. When systemic antiviral immunity was assessed by challenging the immunized mice (groups of 3 C57BL/6 mice) with a high dose of LCMV i.v. (500 pfu), mice which had been immunized once with 200 μg pEGFPL33A DNA i.m. showed only partial and incomplete protection against systemic LCMV challenge, while those which had received 20 μg of pEFGPL33A DNA by the i.spl. or i.ln. routes were completely protected (FIG. 8A).

Eradication of Vacc-G2 infection from peripheral organs such as ovaries, is dependent upon the presence of high levels of recently activated effector CD8$^+$ T cells (Kündig, T. M. et al. *Proc. Natl. Acad. Sci. USA* 93, 9716–9723, 1996; Bachmann, M. F., et al. *Proc. Natl. Acad. Sci. USA* 94, 640–645, 1997). Groups of 3 C57BL/6 mice were immunized four times at 6 day intervals with pEFGPL33A DNA administered either i.m. (100 μg per immunization) or i.ln. (10 μg per immunization). Five days after the last immunization they were challenged with 5×10$^6$ pfu Vacc-G2 i.p. and vaccinia titers in ovaries were assessed after a further 5 days. Repeated i.m. immunization with pEFGPL33A DNA had no influence on the growth of Vacc-G2 in peripheral tissues (FIG. 8B). In contrast, mice which were repetitively immunized with pEFGPL33A DNA by the i.ln. route were completely protected against peripheral infection with Vacc-G2 (FIG. 8B).

These results illustrate that although repeated i.m. immunization with naked DNA induced detectable CTL responses, these were never of sufficient magnitude to offer protection against virus infection. In contrast, immunization with 10-fold lower amounts of DNA directly into lymphoid organs elicited quantitatively and qualitatively stronger CTL responses, which gave complete protection against systemic or peripheral virus challenge.

Example 9
Intra-lymph Node DNA Immunization Elicits Anti-tumor Immunity

Figure 9:
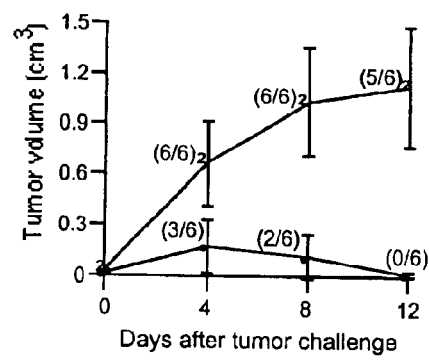
FIG. 9. Growth of transplanted gp33 expressing tumor in mice immunized by i.ln. injection of gp33 epitope-expressing, or control, plasmid.

To examine whether the potent CTL responses elicited following i.ln. immunization were able to confer protection against peripheral tumors, groups of 6 C57BL/6mice were immunized three times at 6-day intervals with 10 µg of pEFGPL33A DNA or control pEGFP-N3 DNA. Five days after the last immunization small pieces of solid tumors expressing the gp33 epitope (EL4-33) were transplanted s.c. into both flanks and tumor growth was measured every 3–4 d. Although the EL4-33 tumors grew well in mice that had been repetitively immunized with control pEGFP-N3 DNA (FIG. 9), mice which were immunized with pEFGPL33A DNA i.ln. rapidly eradicated the peripheral EL4-33 tumors (FIG. 9).

Figure 10:
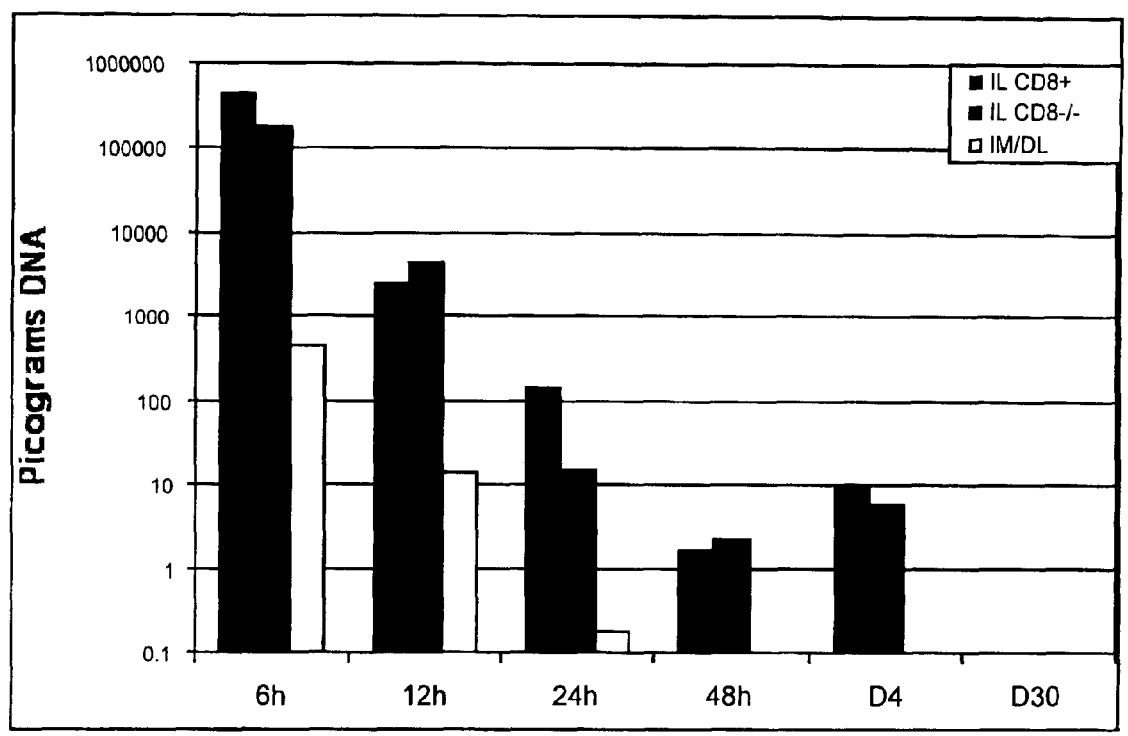
FIG. 10. Amount of plasmid DNA detected by real-time PCR in injected or draining lymph nodes at various times after i.ln. of i.m. injection, respectively.

Example 10
Differences in Lymph Node DNA Content Mirrors Differences in CTL Response Following Intra-Lymph Node and Intramuscular Injection pEFGPL33A DNA was injected i.ln. or i.m. and plasmid content of the injected or draining lymph node was assessed by real time PCR after 6, 12, 24, 48 hours, and 4 and 30 days. At 6, 12, and 24 hours the plasmid DNA content of the injected lymph nodes was approximately three orders of magnitude greater than that of the draining lymph nodes following i.m. injection. No plasmid DNA was detectable in the draining lymph node at subsequent time points (FIG. 10). This is consonant with the three orders of magnitude greater dose needed using i.m. as compared to i.ln. injections to achieve a similar levels of CTL activity. $CD8^{-/-}$ knockout mice, which do not develop a CTL response to this epitope, were also injected i.ln. showing clearance of DNA from the lymph node is not due to CD8+ CTL killing of cells in the lymph node. This observation also supports the conclusion that i.ln. administration will not provoke immunopathological damage to the lymph node.

Example 11
Stability of Plasmid in Different Formulations

DNA is a relatively stable molecule in the kind of formulations of interest to test and thus little loss of material would be noted if the total amount of DNA were to be measured. Instead, the ratio of supercoiled to open-circle DNA was measured. Since a single nick anywhere in either strand of the DNA molecule will allow a supercoiled plasmid to relax to an open circle conformation this is an exquisitely sensitive indication of damage to the DNA backbone. Plasmid was formulated, placed in vials in triplicate and incubated at 37° C. After 1, 3 and 7 days aliquots were removed, subjected to anion exchange HPLC, and the peak areas corresponding to supercoiled and open-circle DNA compared (see FIG. 11). Nine formulations were tested:

1. 10% Ethanol, 0.25 mM EDTA, Citrate Phosphate pH 7.6
2. 10% Ethanol, 0.25 mM EDTA,CitratePhosphate pH 7.4
3. 1% Ethanol, 0.5 mM EDTA, Citrate Phosphate pH 7.4
4. 1% Ethanol, 0.5 mM EDTA, 1X PBS pH 7.4
5. 0.5% Benzyl Alcohol, 0.25 mM EDTA, Citrate Phosphate pH 7.6
6. 1% Benzyl Alcohol, 1% Ethanol, 0.5 mM EDTA, Citrate Phosphate pH 7.6
7. 1% Benzyl Alcohol, 1% Ethanol, 0.5 mM EDTA, 0.1M TRIS pH 7.4
8. 1% Benzyl Alcohol, 1% Ethanol, 0.5mM EDTA, 0.1MTRIS pH 8.2
9. 1% Benzyl Alcohol, 1xPBS pH 8.2

Citrate Phosphate Buffer pH. 7.4 was made by mixing 9.15 parts (by volume) of 0.1M citric acid with 90.85 parts of 0.2M Sodium Phosphate Dibasic. Citrate Phosphate Buffer pH. 7.6 was made by mixing 6.35 parts (by volume) of 0.1M citric acid with 93.65 parts of 0.2M Sodium Phosphate Dibasic. These solutions were then added to the other components to create a 2x buffer which was mixed with a equal volume of DNA in water. Thus the final concentrations of citrate and phosphate in the above buffers was on the order of 3 mM and 90 mM, respectively.

Formulations 1–3 and 6 gave superior results (see FIG. 11).

Example 12
Stability of Formulated Plasmid in Operating MINIMED 407C Infusion Pumps Using a modification (final concentrations of 0.1 M sodium phosphate dibasic and 0.05 M citric acid; pH 7.6±0.2) of formulation 6 above, aliquots of 80, 160, and 320 µg DNA/ml were prepared and loaded in triplicate into MINIMED 3.0 reservoir syringes. A 200 µl sample was dispensed and the reservoir syringes were inserted into MINIMED 407C infusion pumps and assembled with SILHOUETTE infusion sets fitted with 3.1 mm catheters. The pump assemblies, set to dispense 10 µl/hour and with the catheters inserted into collection vials, were placed in 37° C. incubators. At 4 and 8 days the catheters were briefly detached and 200 µl bolus samples dispensed directly from the reservoir. The concentration of supercoiled DNA was determined for each sample by anion exchange HPLC and the use of a standard curve constructed with known concentrations of DNA. Plotting the resultant concentrations versus time allows one to derive a slope indicating the rate of loss of supercoiled DNA. The average (of the triplicate samples) rates of loss were −0.056±1.88, 0.24±1.01, and 0.048±0.49 µg DNA/day for the 80, 160, and 320 µg DNA/ml samples, respectively. None of these differ significantly from zero.

Example 13
Administration of a DNA Plasmid Formulation of a Therapeutic Vaccine for Melanoma to Humans SYNCHROTOPE TA2M, a melanoma vaccine encoding HLA-A2-restricted tyrosinase epitopes was formulated in 1% Benzyl alcohol, 1% ethyl alcohol, 0.5 mM EDTA, citrate-phosphate, pH 7.6. Aliquots of 80, 160, and 320 µg DNA/ml were prepared for loading into MINIMED 407C infusion pumps. The catheter of a SILHOUETTE infusion set is placed into an inguinal lymph node visualized by ultrasound imaging. The assembly of pump and infusion set was originally designed for the delivery of insulin to diabetics and the usual 17 mm catheter has been substituted with a 31 mm catheter for this application. The infusion set is kept patent for 4 days (approximately 96 hours) with an infusion rate of about 25 µl/hour resulting in a total infused volume of approximately 2.4 ml. Thus the total administered dose per infusion will be approximately 200, 400, and 800 µg, respectively, for the three concentrations described above. Following an infusion subjects will be given a 10 day rest period before starting a subsequent infusion. Given the continued residency of plasmid DNA in the lymph node after administration (as in example 10) and the usual kinetics of CTL response following disappearance of antigen, this schedule will be sufficient to maintain the immunologic CTL response.

What is claimed is:

1. A method of inducing a CTL response in a mammal, which method comprises:
   delivering a liquid comprising an antigen directly to a lymph node or lymph vessel of the mammal at a level sufficient to induce an antigen-specific CTL response in the mammal; and
   maintaining the antigen in the mammal's lymphatic system over time sufficient to induce the CTL response.

2. The method of claim 1, wherein the antigen is delivered directly to a lymph node.

3. The method of claim 1, wherein the antigen comprises a protein or peptide.

4. The method of claim 1, wherein the antigen is delivered in a single bolus.

5. The method of claim 1, wherein the antigen is provided as a component of a microorganism.

6. The method of claim 1, wherein the antigen is delivered in the form of a nucleic acid encoding the antigen.

7. The method of claim 6, wherein said nucleic acid is plasmid DNA in a formulation comprising about 1–10% ethyl alcohol, 0–1% benzyl alcohol, 0.25–0.5 mM EDTA and a citrate-phosphate buffer of pH 7.4–7.8, comprising about 3–50 mM citrate and about 90–200 mM phosphate.

8. A method of inducing a CTL response in a mammal, which method comprises:
   delivering a liquid comprising an antigen in a continuous, repeated, or sustained manner directly to a lymph node or lymph vessel of the mammal at a level sufficient to induce an antigen-specific CTL response in the mammal; and
   maintaining the antigen in the mammal's lymphatic system over time sufficient to induce the CTL response.

9. The method of claim 8, wherein induction of cytotoxic T lymphocytes is obtainable independent of immunopotentiator.

10. The method of claim 9, wherein the antigen is delivered with a cytokine.

11. The method of claim 9, wherein the antigen is delivered in the form of a nucleic acid encoding the antigen.

12. The method of claim 8, wherein the antigen is provided as a component of a microorganism cell, and wherein said microorganism cell comprises a recombinant nucleic acid encoding or promoting expression of said antigen.

13. The method of claim 8, wherein the CTL response comprises an immunological CTL response.

14. The method of claim 8, further comprising obtaining a sustained CTL response in the mammal and detecting a CTL response in the mammal.

15. The method of claim 1, wherein said delivering step further comprises delivering said liquid directly to the lymph node or lymph vessel of the mammal from a device external to the mammal.

16. The method of claim 8, wherein said delivering step further comprises delivering said liquid directly to the lymph node or lymph vessel of the mammal from a device external to the mammal.

17. The method of claim 1, wherein the antigen is delivered continuously over a period of time.

18. The method of claim 1, wherein the antigen is selected from the group consisting of a peptide, a polypeptide, a polyepitope amino acid sequence, and a protein.

19. The method of claim 1, wherein the antigen is a component or lysate of a microorganism or mammalian cell.

20. The method of claim 1, wherein the antigen is provided as a vector carrying and/or conferring expression of the antigen.

21. The method of claim 20, wherein the vector is selected from the group consisting of a bacterium, a virus, a protozoan, and a professional antigen-presenting cell.

22. The method of claim 21, wherein the vector is a dendritic cell.

23. The method of claim 8, wherein the antigen is selected from the group consisting of a peptide, a polypeptide, a polyepitope amino acid sequence, and a protein.

24. The method of claim 8, wherein the antigen is a component or lysate of a microorganism or mammalian cell.

25. The method of claim 8, wherein the antigen is provided as a vector carrying and/or conferring expression of the antigen.

26. The method of claim 25, wherein the vector is selected from the group consisting of a bacterium, a virus, a protozoan, and a professional antigen-presenting cell.

27. The method of claim 26, wherein the vector is a dendritic cell.

28. The method of claim 8, wherein the antigen is provided as a component of a microorganism.

29. The method of claim 1, further comprising the step of selecting a patient in need of treatment for a disease condition, wherein the CTL response is specific to an antigen associated with said condition.

30. The method of claim 1, wherein the antigen is a disease-matched antigen.

31. The method of claim 8, further comprising the step of selecting a patient in need of treatment for a disease condition, wherein the CTL response is specific to an antigen associated with said condition.

32. The method of claim 8, wherein the antigen is a disease-matched antigen.

* * * * *